US011554210B2

(12) United States Patent
Shor et al.

(10) Patent No.: US 11,554,210 B2
(45) Date of Patent: Jan. 17, 2023

(54) DEVICE FOR SUBCUTANEOUS DELIVERY OF FLUID MEDICAMENT

(71) Applicant: NeuroDerm, Ltd., Rehovot (IL)

(72) Inventors: Eran Shor, Arugot (IL); Tsabar Mor, Adi (IL); Tamir Ben David, Tel Aviv (IL); Nir Lilach, Kfar Yehoshua (IL); Rami Grossfeld, Haifa (IL); Shai Alfandari, Ramat Hashofet (IL); Ram Nadler, Haifa (IL); Dmitry Golom, Haifa (IL); Daniel Shaki, Herzliya (IL); Yoav Tikochinsky, Tel Aviv (IL); Serdar Ozsumer, Milan (IT)

(73) Assignee: NeuroDerm, Ltd., Rehovot (IL)

(*) Notice: Subject to any disclaimer, the term of this patent is extended or adjusted under 35 U.S.C. 154(b) by 393 days.

(21) Appl. No.: 16/685,364

(22) Filed: Nov. 15, 2019

(65) Prior Publication Data

US 2020/0093984 A1    Mar. 26, 2020

Related U.S. Application Data

(63) Continuation of application No. 16/351,061, filed on Mar. 12, 2019, now Pat. No. 10,603,430, which is a
(Continued)

(51) Int. Cl.
*A61M 5/142*    (2006.01)
*A61M 5/145*    (2006.01)
(Continued)

(52) U.S. Cl.
CPC ........ *A61M 5/14248* (2013.01); *A61J 1/2003* (2015.05); *A61J 1/2013* (2015.05);
(Continued)

(58) Field of Classification Search
CPC ......... A61M 2005/14268; A61M 2005/14573; A61M 5/1456; A61M 5/14566;
(Continued)

(56) References Cited

U.S. PATENT DOCUMENTS 3,938,018 A    2/1976    Dahl
4,684,869 A    8/1987    Kobayashi et al.
(Continued)

FOREIGN PATENT DOCUMENTS

CN    204337287 U    5/2015
CN    205181787 U    4/2016
(Continued)

OTHER PUBLICATIONS

Extended European Search Report, issued for EP Application No. 20175559.2-1122, dated Aug. 12, 2020 (8 pages).
(Continued)

*Primary Examiner* — James D Ponton
(74) *Attorney, Agent, or Firm* — Goodwin Procter LLP

(57) ABSTRACT

An improved device delivers a fluid medicament to the subcutaneous tissue of a user. The device is better suited for patients with Parkinson's Disease and other central nervous system disorders, than conventional infusion devices. The device can include a reusable part including a drive component (e.g., motor) and control electronics and a disposable part including a medicament reservoir. Medicament can be evacuated from the medicament reservoir by a plunger assembly that includes a plunger attached to a lead screw that is rotated by a nut, all within the disposable part. The device can be fluidically coupled with the tissue via a flexible cannula. Various embodiments relate to an improved cannula insertion mechanism that delivers the cannula under a force applied by a spring. Various embodiments relate to
(Continued)

improved filling of the device, for example, using a vial adapter and an automated filling station.

26 Claims, 64 Drawing Sheets

Related U.S. Application Data continuation of application No. 16/027,804, filed on Jul. 5, 2018, now abandoned.

(60) Provisional application No. 62/576,362, filed on Oct. 24, 2017, provisional application No. 62/529,784, filed on Jul. 7, 2017.

(51) Int. Cl.

| | | |
|---|---|---|
| *A61M 5/315* | (2006.01) | |
| *A61M 5/172* | (2006.01) | |
| *A61M 5/178* | (2006.01) | |
| *A61M 5/34* | (2006.01) | |
| *A61J 1/20* | (2006.01) | |
| *A61M 5/14* | (2006.01) | |
| *H03H 9/05* | (2006.01) | |
| *H03H 9/54* | (2006.01) | |
| *H03H 9/64* | (2006.01) | |
| *A61M 5/31* | (2006.01) | |
| *A61M 5/158* | (2006.01) | |

(52) U.S. Cl.
CPC ........ *A61M 5/1407* (2013.01); *A61M 5/1413* (2013.01); *A61M 5/1456* (2013.01); *A61M 5/14216* (2013.01); *A61M 5/1723* (2013.01); *A61M 5/1782* (2013.01); *A61M 5/31528* (2013.01); *A61M 5/345* (2013.01); *H03H 9/0509* (2013.01); *H03H 9/0585* (2013.01); *H03H 9/54* (2013.01); *H03H 9/64* (2013.01); *A61M 2005/14252* (2013.01); *A61M 2005/14268* (2013.01); *A61M 2005/14506* (2013.01); *A61M 2005/14573* (2013.01); *A61M 2005/1586* (2013.01); *A61M 2005/1726* (2013.01); *A61M 2005/3125* (2013.01); *A61M 2202/0468* (2013.01); *A61M 2205/13* (2013.01); *A61M 2205/33* (2013.01); *A61M 2205/50* (2013.01); *A61M 2205/8206* (2013.01); *A61M 2210/04* (2013.01)

(58) Field of Classification Search
CPC ............ A61M 5/14248; A61M 5/1407; A61M 5/1413; A61M 5/14216; A61M 5/1723; A61M 5/1782; A61M 5/31528; A61M 5/345; A61M 2005/14252; A61M 2005/14506; A61M 2005/1586; A61M 2005/1726; A61M 2005/3125; A61M 2202/0468; A61M 2205/13; A61M 2205/33; A61M 2205/50; A61M 2205/8206; A61M 2210/04; A61J 1/2003; A61J 1/2013; H03H 9/0509; H03H 9/0585; H03H 9/54; H03H 9/64
See application file for complete search history.

(56) References Cited

U.S. PATENT DOCUMENTS

| | | |
|---|---|---|
| 4,873,677 A | 10/1989 | Sakamoto et al. |
| 5,070,293 A | 12/1991 | Ishii et al. |
| 5,455,466 A | 10/1995 | Parks et al. |
| 5,600,225 A | 2/1997 | Goto |
| 5,680,028 A | 10/1997 | McEachern |
| 5,733,313 A | 3/1998 | Barreras, Sr. et al. |
| 5,929,598 A | 7/1999 | Nakama et al. |
| 6,040,680 A | 3/2000 | Toya et al. |
| 6,118,249 A | 9/2000 | Brockmann et al. |
| 6,184,651 B1 | 2/2001 | Fernandez et al. |
| 6,447,487 B1 | 9/2002 | Cane' |
| 6,607,509 B2 | 8/2003 | Bobroff et al. |
| 6,607,543 B2 | 8/2003 | Purcell et al. |
| 6,633,155 B1 | 10/2003 | Liang |
| 6,650,088 B1 | 11/2003 | Webb et al. |
| 6,685,675 B1 | 2/2004 | Hadvary et al. |
| 6,740,059 B2 | 5/2004 | Flaherty |
| 6,997,907 B2 | 2/2006 | Safabash et al. |
| 7,375,492 B2 | 5/2008 | Calhoon et al. |
| 7,471,062 B2 | 12/2008 | Bruning |
| 7,514,899 B2 | 4/2009 | Deng-Peng |
| 7,569,050 B2 | 8/2009 | Moberg et al. |
| 7,726,955 B2 | 6/2010 | Ryser et al. |
| 7,825,625 B2 | 11/2010 | Posamentier |
| 7,887,511 B2 | 2/2011 | Mernoe et al. |
| 8,002,752 B2 | 8/2011 | Yodfat et al. |
| 8,120,317 B2 | 2/2012 | Sip |
| 8,164,222 B2 | 4/2012 | Baarman |
| 8,167,841 B2 | 5/2012 | Teisen-Simony et al. |
| 8,231,577 B2 | 7/2012 | Carter et al. |
| 8,287,495 B2 | 10/2012 | Michaud et al. |
| 8,292,849 B2 | 10/2012 | Bobroff et al. |
| 8,294,300 B2 | 10/2012 | Cook et al. |
| 8,298,172 B2 | 10/2012 | Nielsen et al. |
| 8,303,549 B2 | 11/2012 | Mejlhede et al. |
| 8,323,250 B2 | 12/2012 | Chong et al. |
| 8,339,096 B2 | 12/2012 | Osada |
| 8,382,700 B2 | 2/2013 | Straessler et al. |
| 8,395,353 B2 | 3/2013 | Wang et al. |
| 8,409,143 B2 | 4/2013 | Lanigan et al. |
| 8,500,692 B2 | 8/2013 | Yodfat et al. |
| 8,610,398 B2 | 12/2013 | Lee et al. |
| 8,628,500 B2 | 1/2014 | Yodfat et al. |
| 8,632,499 B2 | 1/2014 | Grant et al. |
| 8,641,672 B2 | 2/2014 | Yodfat et al. |
| 8,728,034 B2 | 5/2014 | Yodfat et al. |
| 8,816,638 B2 | 8/2014 | Vorenkamp et al. |
| 8,821,442 B2 | 9/2014 | Haar |
| 8,845,587 B2 | 9/2014 | Lanigan et al. |
| 8,849,459 B2 | 9/2014 | Ramey et al. |
| 8,855,554 B2 | 10/2014 | Cook et al. |
| 8,858,500 B2 | 10/2014 | Hanson et al. |
| 8,882,701 B2 | 11/2014 | DeBelser et al. |
| 8,882,710 B2 | 11/2014 | Chong et al. |
| 8,888,744 B2 | 11/2014 | Yodfat et al. |
| 8,900,189 B2 | 12/2014 | Yodfat et al. |
| 8,920,374 B2 | 12/2014 | Bokelman et al. |
| 8,947,042 B2 | 2/2015 | Kirby et al. |
| 8,957,674 B2 | 2/2015 | Genoud et al. |
| 8,961,467 B2 | 2/2015 | Lanigan et al. |
| 8,986,250 B2 | 3/2015 | Beebe et al. |
| 9,059,599 B2 | 6/2015 | Won et al. |
| 9,114,208 B2 | 8/2015 | Smith et al. |
| 9,119,917 B2 | 9/2015 | Blomquist |
| 9,138,564 B2 | 9/2015 | Morrissey et al. |
| 9,166,438 B2 | 10/2015 | Sultenfuss et al. |
| 9,173,997 B2 | 11/2015 | Gross et al. |
| 9,205,189 B2 | 12/2015 | Graf et al. |
| 9,211,377 B2 | 12/2015 | DiPerna et al. |
| 9,220,835 B2 | 12/2015 | Cane' |
| 9,222,470 B2 | 12/2015 | Genoud et al. |
| 9,236,756 B2 | 1/2016 | Jenwatanavet et al. |
| 9,282,366 B2 | 3/2016 | Nielsen |
| 9,300,151 B2 | 3/2016 | Chen et al. |
| 9,300,162 B2 | 3/2016 | Lai et al. |
| 9,301,259 B2 | 3/2016 | Tuli |
| 9,302,285 B2 | 4/2016 | Marbet et al. |
| 9,308,318 B2 | 4/2016 | Lanigan et al. |
| 9,319,086 B2 | 4/2016 | Wong |
| 9,333,367 B2 | 5/2016 | Chen |
| 9,385,557 B2 | 7/2016 | Causey et al. |
| 9,415,163 B2 | 8/2016 | Ricotti et al. |
| 9,438,067 B2 | 9/2016 | Na et al. |
| 9,444,284 B2 | 9/2016 | Schuessler |

(56) References Cited

U.S. PATENT DOCUMENTS

| | | |
|---|---|---|
| 9,446,188 B2 | 9/2016 | Grant et al. |
| 9,457,140 B2 | 10/2016 | Barron et al. |
| 9,463,271 B2 | 10/2016 | Cane' |
| 9,494,147 B2 | 11/2016 | Chong et al. |
| 9,502,913 B2 | 11/2016 | Castillo et al. |
| 9,507,969 B2 | 11/2016 | Chu |
| 9,564,940 B2 | 2/2017 | Park et al. |
| 9,566,448 B2 | 2/2017 | Forsell |
| 9,572,924 B2 | 2/2017 | Yodfat et al. |
| 9,592,336 B2 | 3/2017 | Nielsen et al. |
| 9,597,522 B2 | 3/2017 | Meskens |
| 9,608,475 B1 | 3/2017 | Karanikos et al. |
| 9,610,402 B2 | 4/2017 | Yavorsky et al. |
| 9,610,455 B2 | 4/2017 | Forsell |
| 9,627,913 B2 | 4/2017 | Maugars |
| 9,635,152 B2 | 4/2017 | Ma et al. |
| 9,662,271 B2 | 5/2017 | Holt et al. |
| 9,662,438 B2 | 5/2017 | Kamen et al. |
| 9,662,621 B2 | 5/2017 | Beyer et al. |
| 9,667,077 B2 | 5/2017 | Kim et al. |
| 9,680,966 B2 | 6/2017 | Bush et al. |
| 9,722,455 B2 | 8/2017 | Saari et al. |
| 9,778,691 B2 | 10/2017 | Sedlmair |
| 9,793,744 B2 | 10/2017 | Zhang et al. |
| 9,812,892 B2 | 11/2017 | Miller et al. |
| 9,837,847 B2 | 12/2017 | Waldschmidt |
| 9,843,214 B2 | 12/2017 | Peek et al. |
| 9,879,668 B2 | 1/2018 | Yavorsky et al. |
| 9,987,422 B2 | 6/2018 | Vazquez et al. |
| 9,993,595 B2 | 6/2018 | Michaud et al. |
| 9,999,722 B2 | 6/2018 | Yodfat et al. |
| 10,016,559 B2 | 7/2018 | DeBelser et al. |
| 10,130,755 B2 | 11/2018 | Anderson et al. |
| 2003/0048254 A1 | 3/2003 | Huang |
| 2005/0238507 A1 | 10/2005 | Dilanni et al. |
| 2006/0041276 A1* | 2/2006 | Chan ............. A61M 5/14276 607/3 |
| 2006/0161218 A1 | 7/2006 | Danilov |
| 2006/0253086 A1* | 11/2006 | Moberg ............ A61M 5/1456 604/272 |
| 2007/0073235 A1* | 3/2007 | Estes ............. A61M 5/14244 604/151 |
| 2008/0215030 A1 | 9/2008 | Ritsher |
| 2008/0306445 A1 | 12/2008 | Burren et al. |
| 2009/0062652 A1 | 3/2009 | Shin et al. |
| 2009/0075704 A1 | 3/2009 | Wang |
| 2009/0093793 A1 | 4/2009 | Gross et al. |
| 2009/0121676 A1 | 5/2009 | Wu et al. |
| 2010/0130931 A1* | 5/2010 | Yodfat ............. F04B 43/1269 604/151 |
| 2010/0292651 A1 | 11/2010 | Yodfat et al. |
| 2011/0060280 A1 | 3/2011 | Caffey et al. |
| 2011/0137255 A1 | 6/2011 | Nielsen et al. |
| 2011/0213329 A1 | 9/2011 | Yodfat et al. |
| 2011/0230891 A1 | 9/2011 | Deck et al. |
| 2011/0270188 A1 | 11/2011 | Caffey et al. |
| 2012/0022453 A1 | 1/2012 | Yodfat et al. |
| 2012/0078222 A1 | 3/2012 | Smith et al. |
| 2012/0109062 A1 | 5/2012 | Lanigan |
| 2012/0143133 A1* | 6/2012 | Congnome ....... A61M 5/14244 604/131 |
| 2012/0184907 A1* | 7/2012 | Smith ............. A61M 5/14248 604/152 |
| 2012/0299966 A1 | 11/2012 | Kim et al. |
| 2013/0253430 A1 | 9/2013 | Kouyoumjian et al. |
| 2013/0317436 A1 | 11/2013 | Ning et al. |
| 2014/0010727 A1 | 1/2014 | Jugl et al. |
| 2014/0058353 A1 | 2/2014 | Politis et al. |
| 2014/0074062 A1 | 3/2014 | Caffey et al. |
| 2014/0088192 A1 | 3/2014 | Heller et al. |
| 2014/0142508 A1 | 5/2014 | Dilanni et al. |
| 2014/0148784 A1 | 5/2014 | Anderson et al. |
| 2014/0163523 A1 | 6/2014 | Constantineau et al. |
| 2014/0174223 A1 | 6/2014 | Gross et al. |
| 2014/0194815 A1 | 7/2014 | Kouyoumjian et al. |
| 2014/0194821 A1 | 7/2014 | Albrecht et al. |
| 2014/0207104 A1 | 7/2014 | Vouillamoz et al. |
| 2014/0298447 A1 | 10/2014 | Chu |
| 2014/0308995 A1 | 10/2014 | Wu |
| 2014/0368163 A1 | 12/2014 | Ho |
| 2015/0008875 A1 | 1/2015 | Huang et al. |
| 2015/0038907 A1 | 2/2015 | Rotem |
| 2015/0112264 A1 | 4/2015 | Kamen et al. |
| 2015/0115881 A1 | 4/2015 | Park et al. |
| 2015/0119798 A1 | 4/2015 | Gross et al. |
| 2015/0151041 A1 | 6/2015 | Yodfat et al. |
| 2015/0174326 A1 | 6/2015 | Bokelman et al. |
| 2015/0184648 A1 | 7/2015 | Dhami |
| 2015/0217046 A1* | 8/2015 | Heller ............... A61P 25/16 514/486 |
| 2015/0224253 A1 | 8/2015 | Cabiri |
| 2015/0306307 A1 | 10/2015 | Cole et al. |
| 2015/0306313 A1 | 10/2015 | Baykal |
| 2015/0326058 A1 | 11/2015 | Chu |
| 2015/0352276 A1 | 12/2015 | Yodfat et al. |
| 2016/0045715 A1 | 2/2016 | Galgano et al. |
| 2016/0067403 A1 | 3/2016 | Moberg et al. |
| 2016/0072334 A1 | 3/2016 | Wu |
| 2016/0082181 A1 | 3/2016 | Lanigan et al. |
| 2016/0082182 A1 | 3/2016 | Gregory et al. |
| 2016/0089491 A1 | 3/2016 | Smith |
| 2016/0106927 A1 | 4/2016 | Moeller et al. |
| 2016/0118838 A1 | 4/2016 | Ou |
| 2016/0184512 A1 | 6/2016 | Marbet et al. |
| 2016/0220755 A1 | 8/2016 | Lanigan et al. |
| 2016/0220798 A1 | 8/2016 | Netzel et al. |
| 2016/0235913 A1 | 8/2016 | Smith et al. |
| 2016/0250422 A1 | 9/2016 | Koch et al. |
| 2016/0256353 A1* | 9/2016 | Bar-El ............... A61J 1/1406 |
| 2016/0296695 A1 | 10/2016 | Hassman et al. |
| 2016/0322849 A1 | 11/2016 | Yeh et al. |
| 2016/0325041 A1 | 11/2016 | Hoeholt et al. |
| 2016/0331901 A1 | 11/2016 | Grubbe et al. |
| 2016/0346465 A1 | 12/2016 | Qi et al. |
| 2016/0374049 A1 | 12/2016 | Ha et al. |
| 2016/0380464 A1 | 12/2016 | Chin et al. |
| 2017/0007779 A1 | 1/2017 | Grant et al. |
| 2017/0012457 A1 | 1/2017 | Huang et al. |
| 2017/0028171 A1 | 2/2017 | Ishida |
| 2017/0043090 A1 | 2/2017 | Mueller-Pathle |
| 2017/0056582 A1 | 3/2017 | Niklaus |
| 2017/0117738 A1 | 4/2017 | Yeoh et al. |
| 2017/0155270 A1 | 6/2017 | Wang |
| 2017/0163070 A1 | 6/2017 | Lawrenson et al. |
| 2017/0187221 A1 | 6/2017 | Konanur et al. |
| 2017/0189625 A1 | 7/2017 | Cirillo et al. |
| 2017/0207659 A1 | 7/2017 | Mofidi et al. |
| 2017/0302097 A1 | 10/2017 | Kim et al. |
| 2017/0302324 A1 | 10/2017 | Stanimirovic et al. |
| 2017/0331329 A1 | 11/2017 | Kim et al. |
| 2017/0357337 A1 | 12/2017 | Chou |
| 2018/0161243 A1 | 6/2018 | Ariagno et al. |
| 2018/0193555 A1 | 7/2018 | Michaud et al. |
| 2018/0353695 A1 | 12/2018 | Helmer |

FOREIGN PATENT DOCUMENTS

| | | |
|---|---|---|
| EP | 2125077 A2 | 12/2009 |
| EP | 2353628 A2 | 8/2011 |
| EP | 2255773 B1 | 1/2012 |
| EP | 2753380 A1 | 7/2014 |
| EP | 2579917 B1 | 10/2016 |
| JP | 2010526633 A | 8/2010 |
| JP | 2014519900 A | 8/2014 |
| JP | 2015509431 A | 3/2015 |
| JP | 2017-517296 A | 6/2017 |
| WO | WO-1995016490 A1 | 6/1995 |
| WO | WO-2004077550 A1 | 9/2004 |
| WO | WO-2007092624 A3 | 12/2007 |
| WO | WO-2008078318 A2 | 7/2008 |
| WO | WO-2008101589 A3 | 11/2008 |
| WO | WO-2008139458 A2 | 11/2008 |
| WO | WO-2009016638 A1 | 2/2009 |

(56) References Cited

FOREIGN PATENT DOCUMENTS

| WO | WO-2009065419 A1 | 5/2009 |
|----|------------------|--------|
| WO | WO-2009065801 A1 | 5/2009 |
| WO | WO-2009/125398 A3 | 2/2010 |
| WO | WO-2010038182 A3 | 6/2010 |
| WO | WO-2010/076792 A1 | 7/2010 |
| WO | WO-2011154928 A1 | 12/2011 |
| WO | WO-2012160156 A2 | 11/2012 |
| WO | WO-2013034159 A1 | 3/2013 |
| WO | WO-2013132414 A1 | 9/2013 |
| WO | WO-2013134246 A1 | 9/2013 |
| WO | WO-2013134614 A2 | 9/2013 |
| WO | WO-2013172530 A1 | 11/2013 |
| WO | WO-2014029433 A1 | 2/2014 |
| WO | WO-201396789 A8 | 7/2014 |
| WO | WO-2015164651 A1 | 10/2015 |
| WO | WO-2015-196172 A3 | 4/2016 |
| WO | WO-2016/100055 A1 | 6/2016 |
| WO | WO-2017-007968 A1 | 1/2017 |
| WO | WO-2017109799 A1 | 6/2017 |
| WO | WO-2017131734 A1 | 8/2017 |

OTHER PUBLICATIONS

International Search Report and Written Opinion dated Dec. 13, 2018 issued for PCT/IB2018/054962.

* cited by examiner

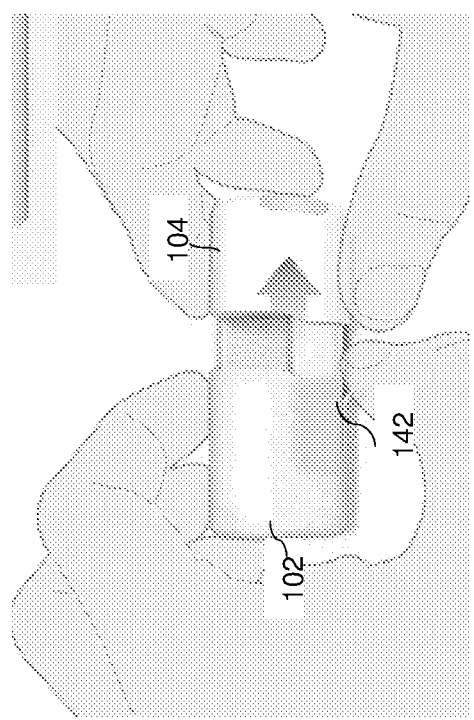
FIG. 8A
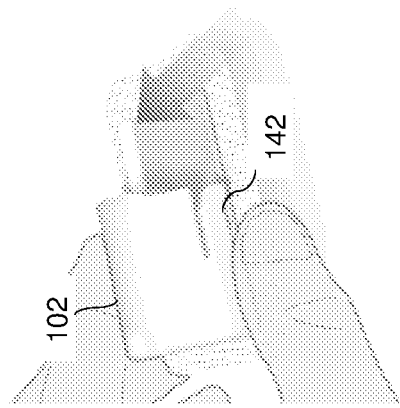
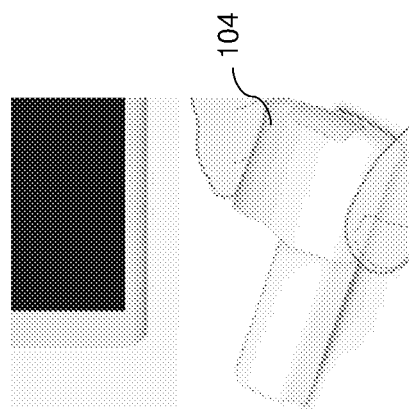
FIG. 8B

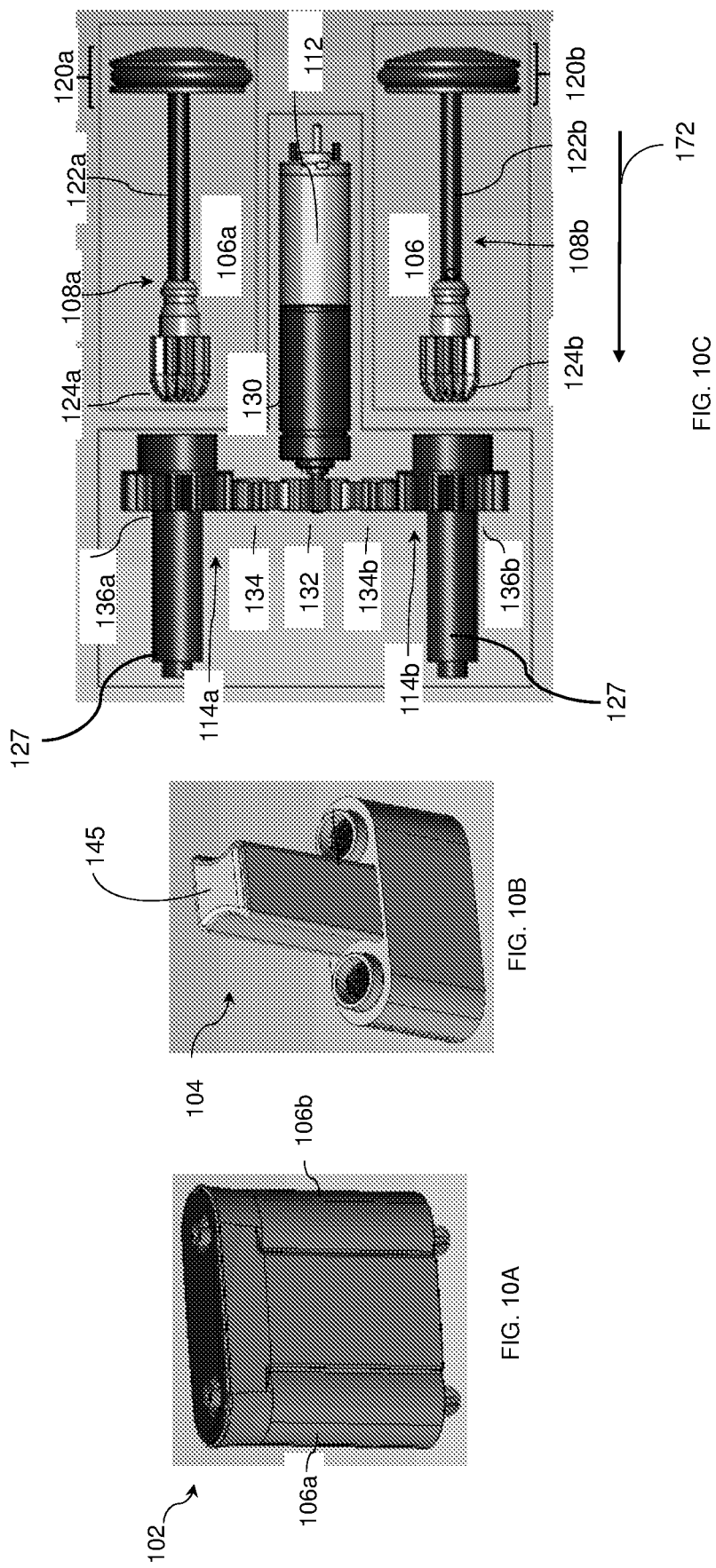

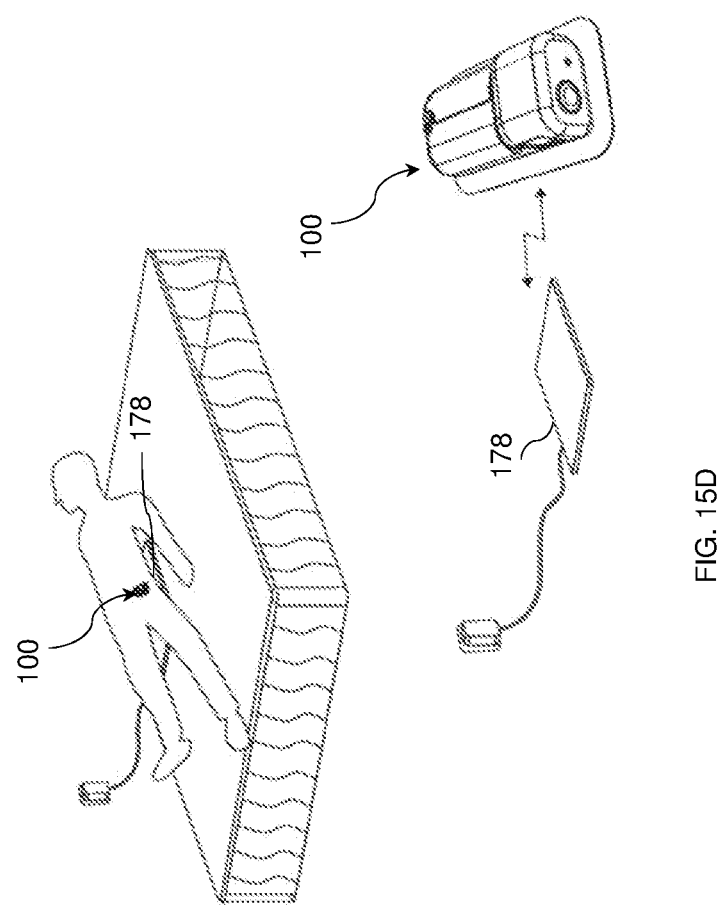

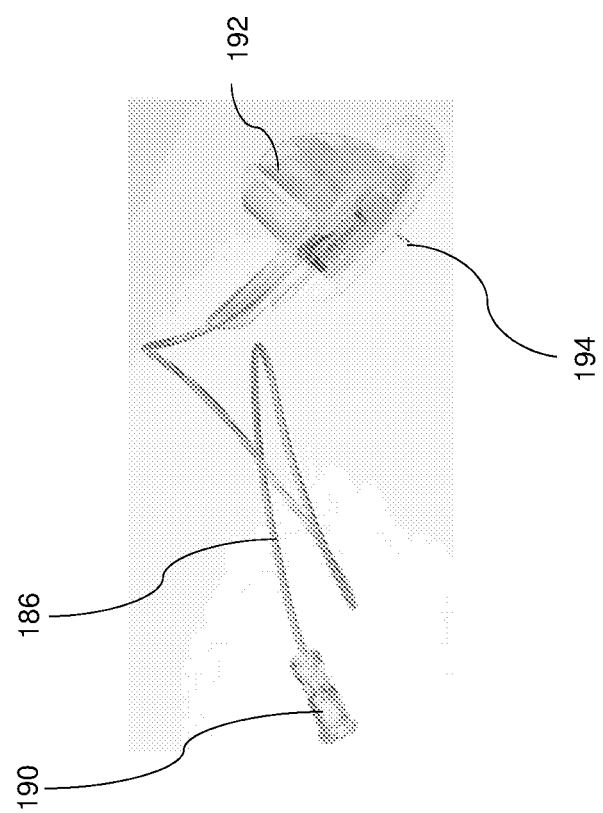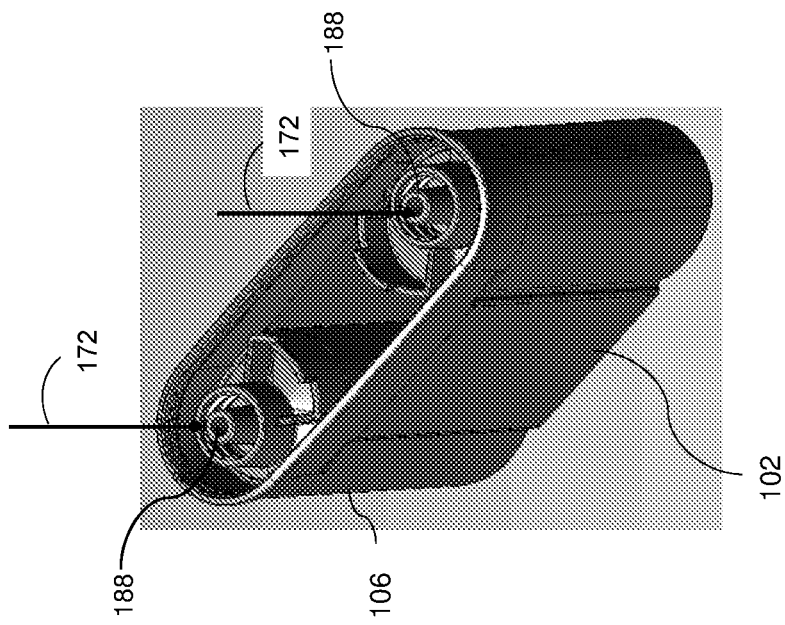
FIG. 16

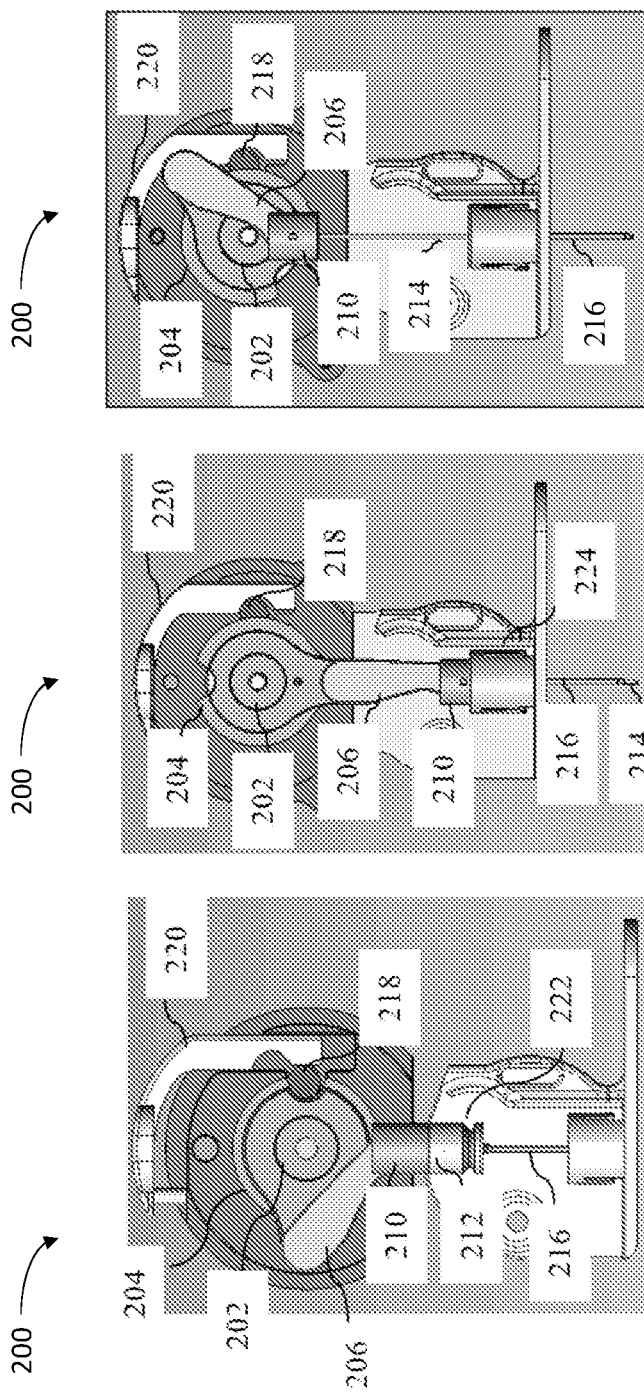

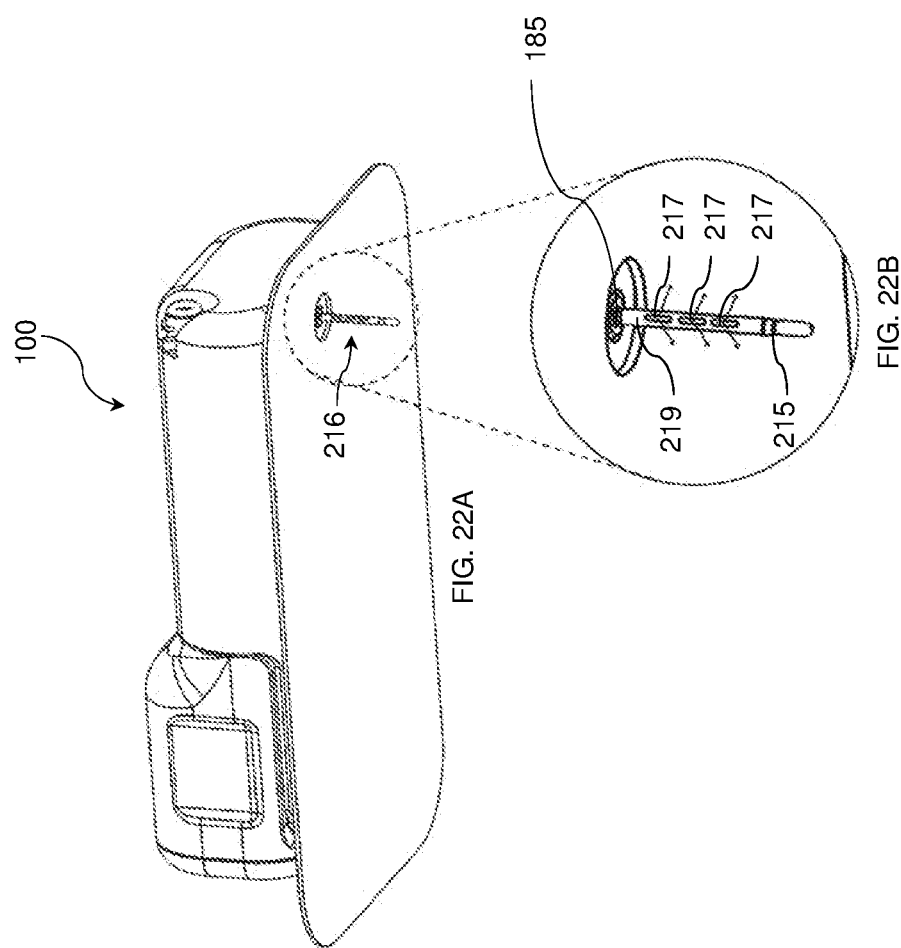

Before Cannula Delivery

First Delivery Stage

Second Delivery Stage

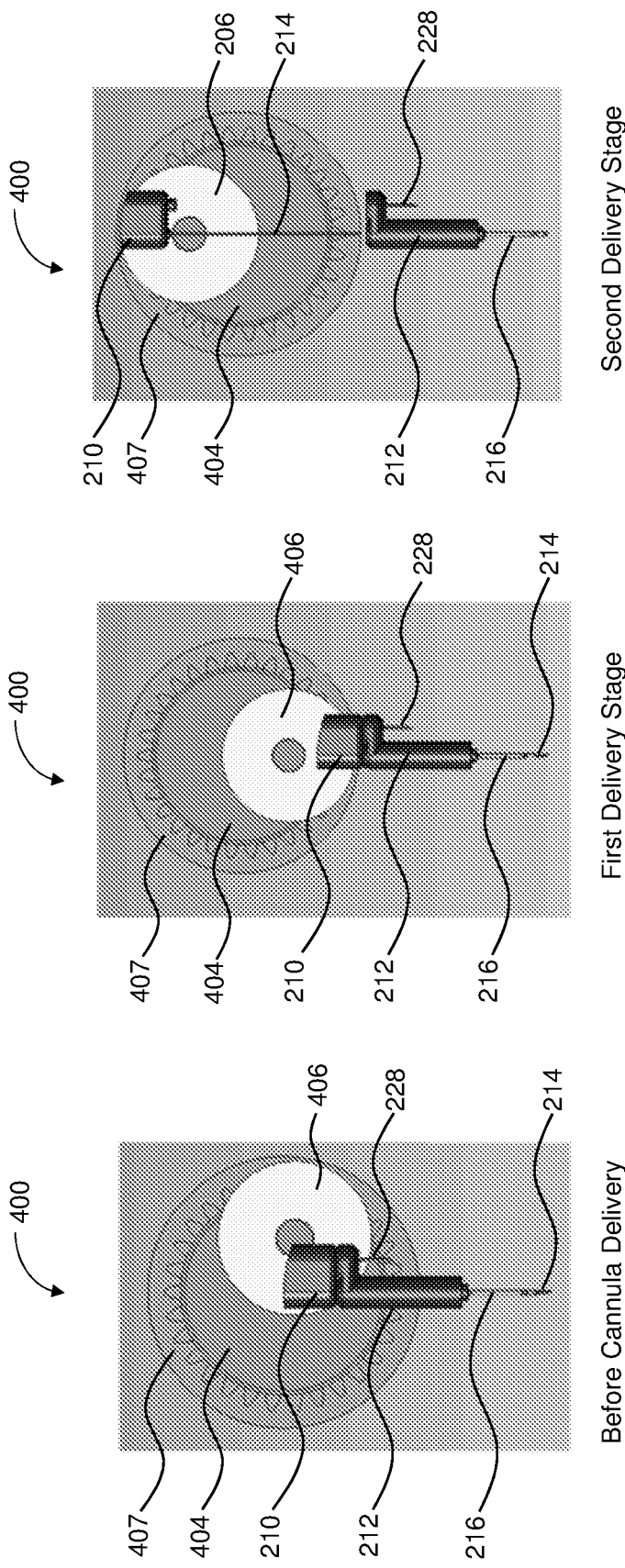

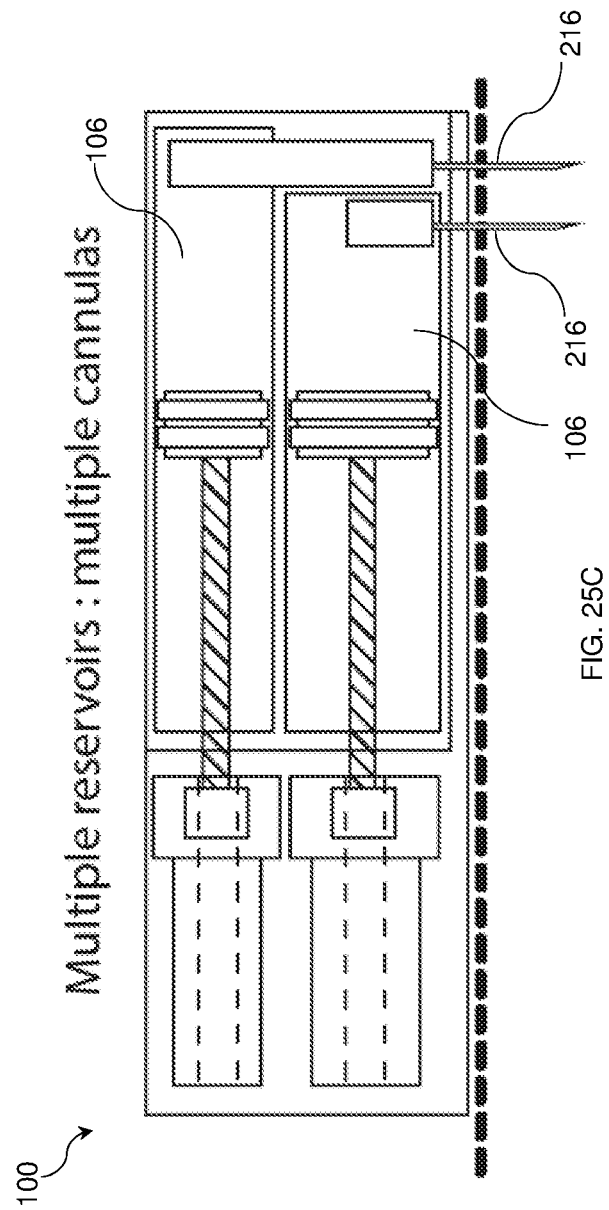

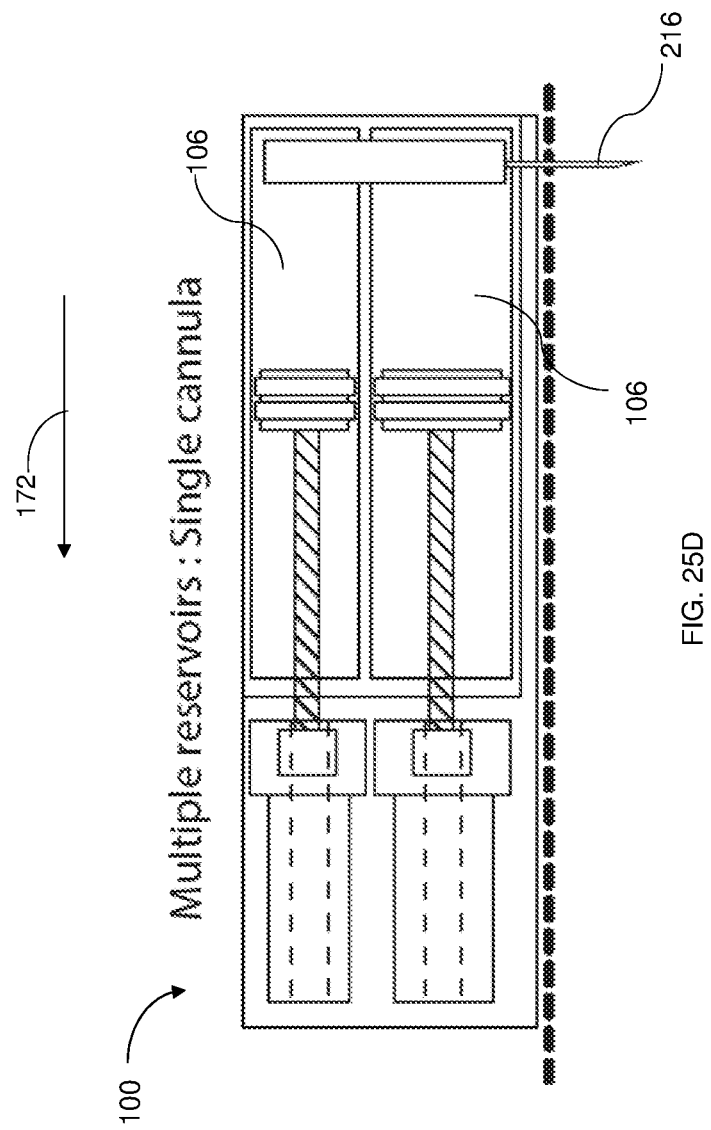

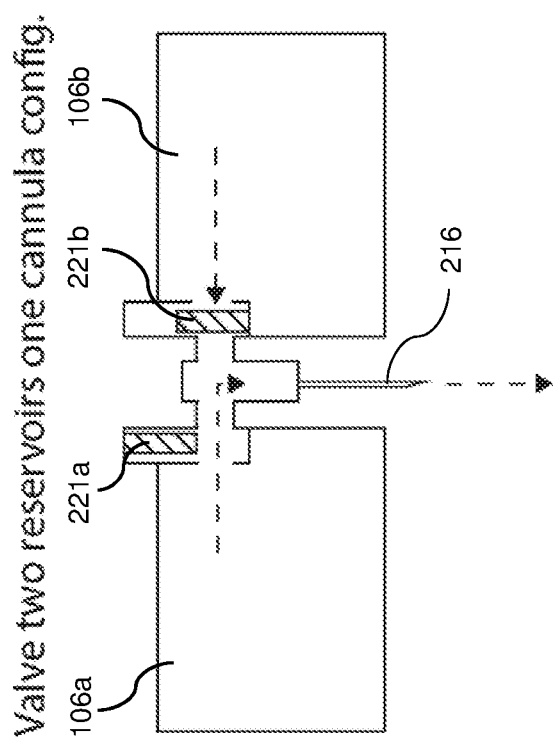

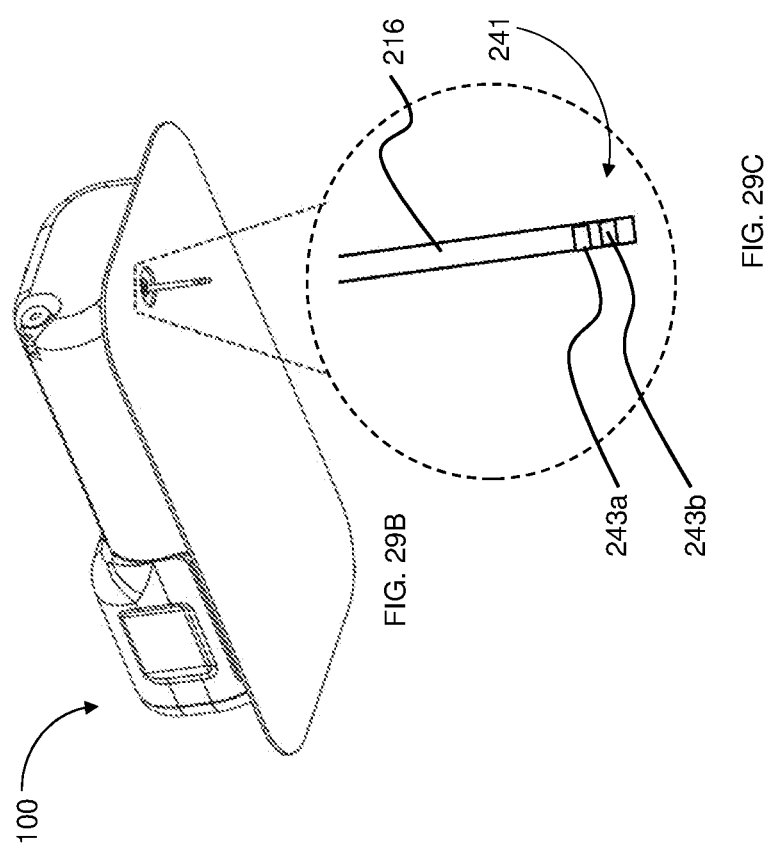

| Parameter | Min. Value | Nominal Value | Max. Value | (Units) |
|---|---|---|---|---|
| 1. Delivery Rate | 20 | 220 | 850 | ml/hr |
| 2. Reservoir Capacity | 2 | 4.5 | 12 | ml |
| 3. Fluid Pressure | -0.5 | 1.5 | 4 | bar |
| 4. Fluid Temperature | 4 | 25 | 40 | Celsius |
| 5. Force Required to Insert Vial onto Fill Needle | 4 | 10 | 40 | N |
| 6. Device Length | 40 | 60 | 90 | mm |
| 7. Device Width | 20 | 45 | 60 | mm |
| 8. Device Height | 15 | 25 | 40 | mm |
| 9. Device Weight | 25 | 120 | 160 | grams |
| 10. Motor Power Capacity | 0.5 | 1.3 | 2 | W |
| 11. Time Of "On Period" – Medicament Delivery | 0.15 | 0.75 | 0.9 | sec |
| 12. Time Of "Off Period" – Medicament Delivery | 0.5 | 13 | 27 | min |
| 13. Filling Rate | 0.1 | 1 | 3 | ml/min |
| 14. Total Delivery Time | 4 | 24 | 48 | hr |
| 15. Micro Step Volume | 2 | 5 | 12 | mm3 |
| 16. Time For Day/Night Rate Change | 20:00 | 22:00 | 04:00 | hr |
| 17. Number of Delivery Profiles | 1 | 5 | 8 | N/A |

FIG. 33

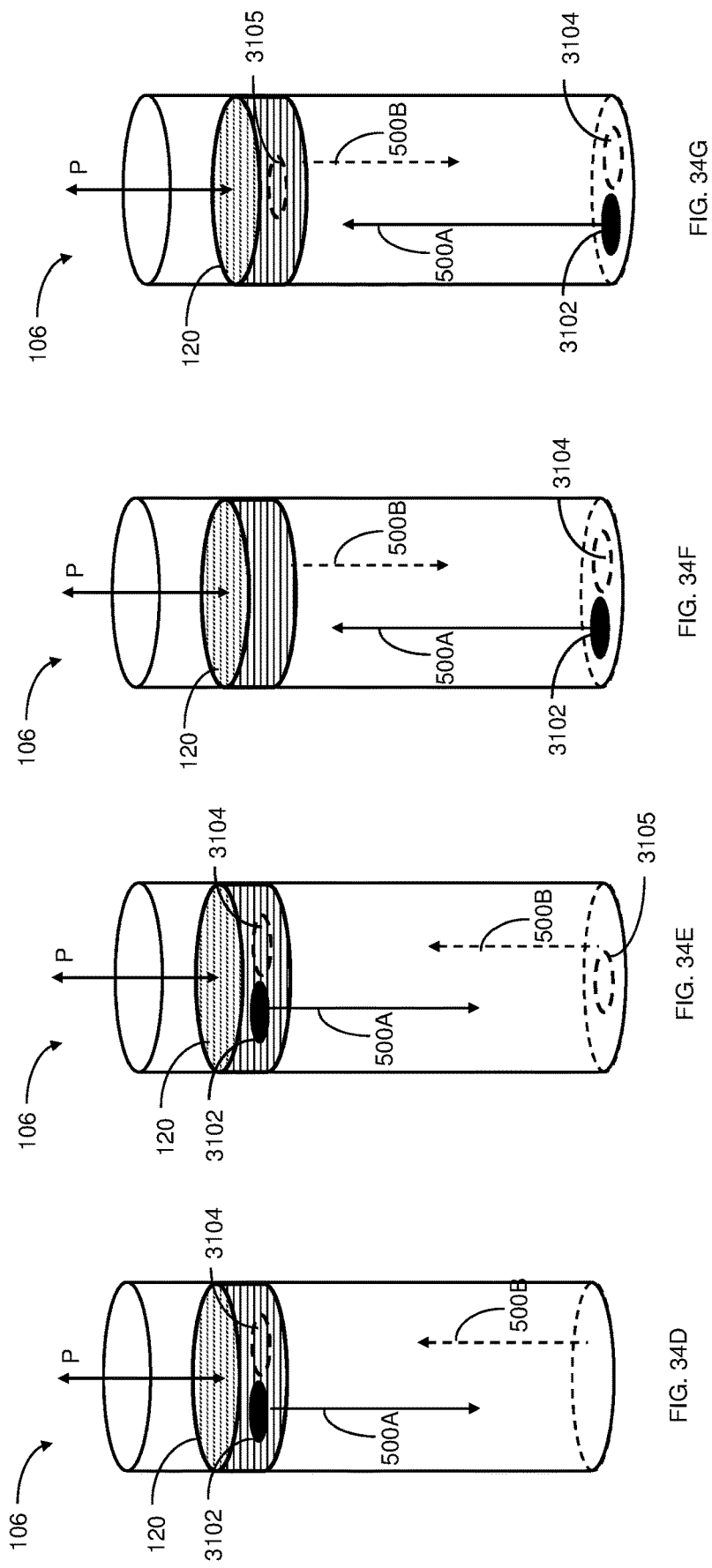

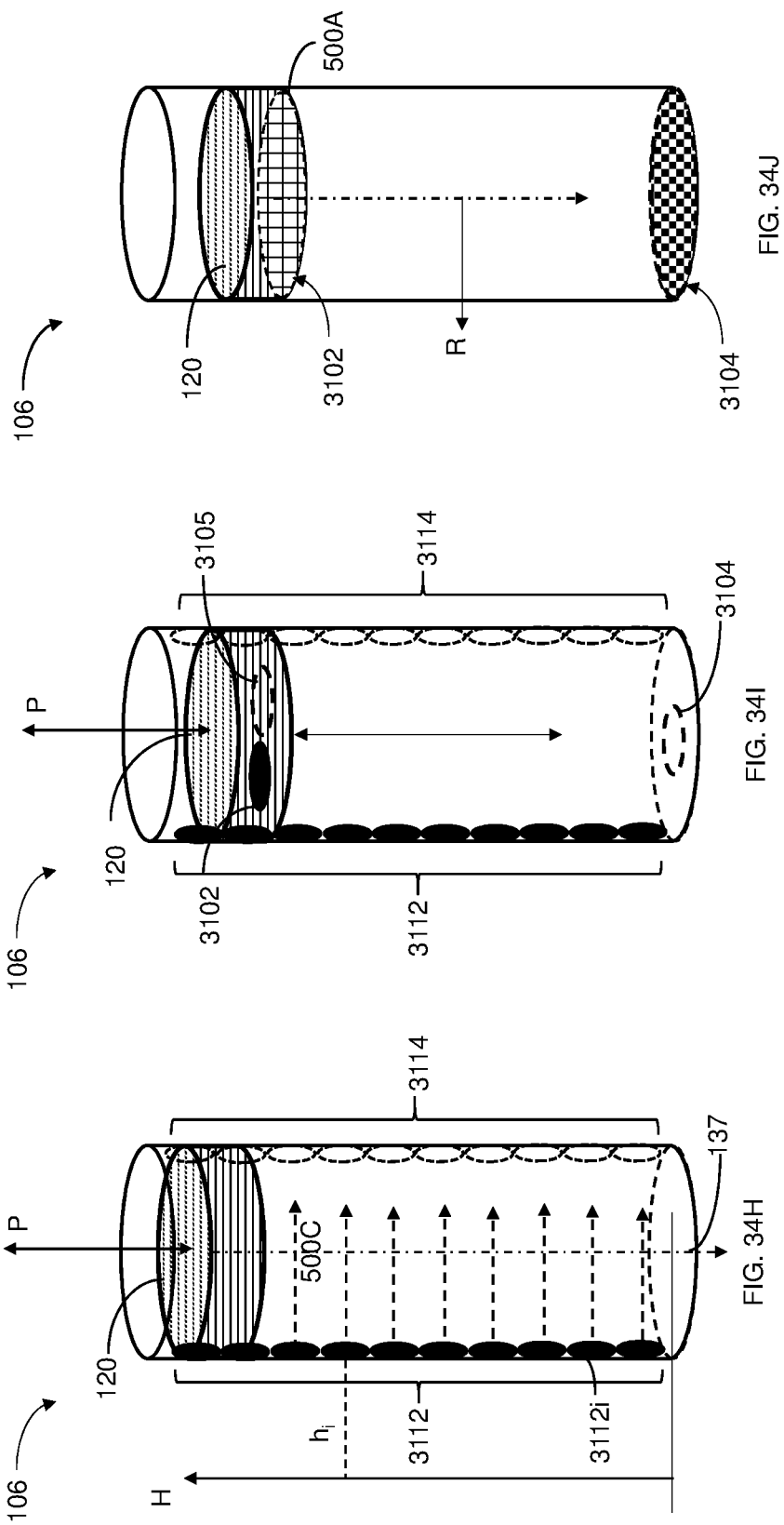

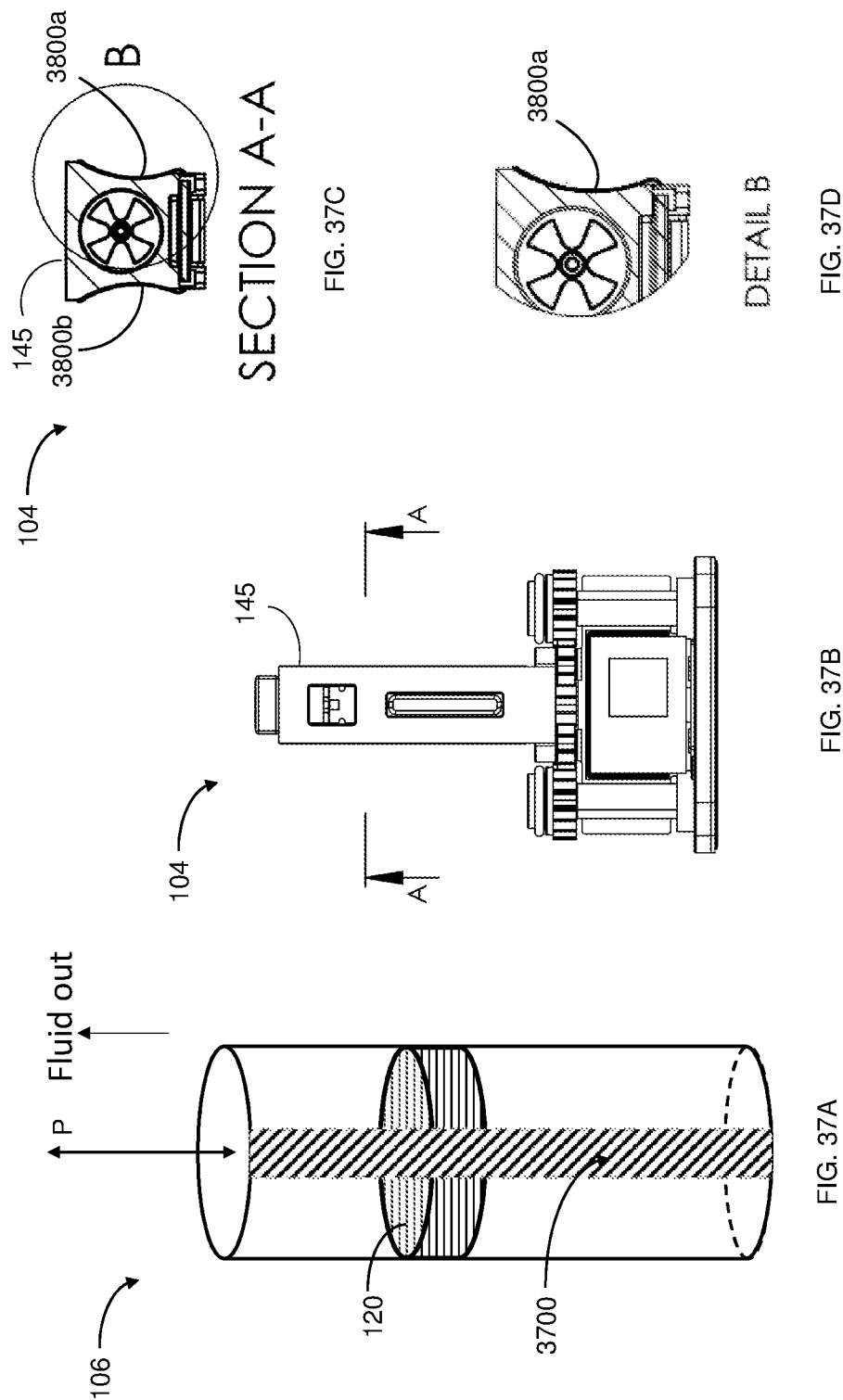

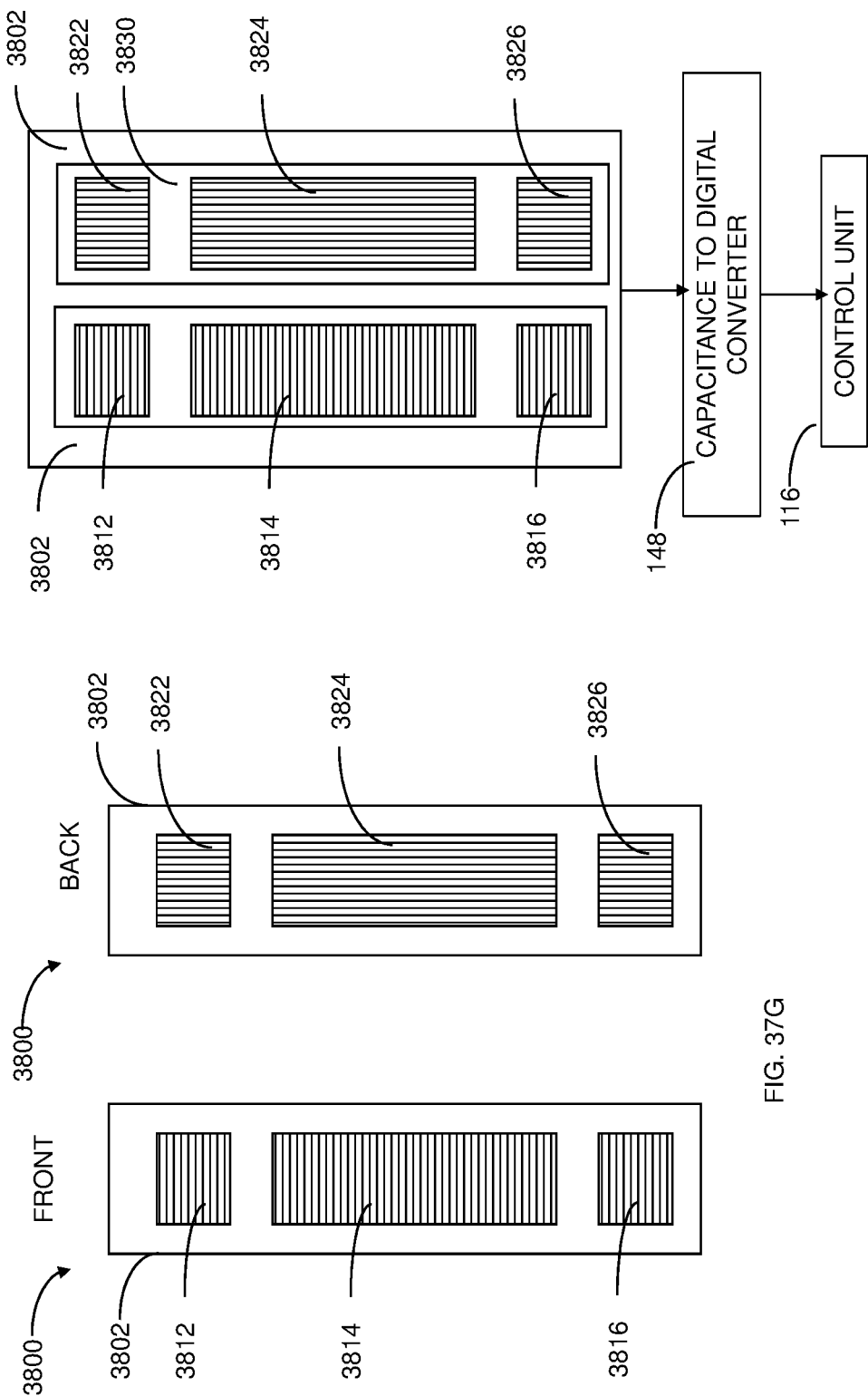

DEVICE FOR SUBCUTANEOUS DELIVERY OF FLUID MEDICAMENT

CROSS-REFERENCE TO RELATED APPLICATIONS

This application is a continuation of and claims the benefit of priority to U.S. patent application Ser. No. 16/351,061 entitled "Device for Subcutaneous Delivery of Fluid Medicament," filed on Mar. 12, 2019, which is a continuation of and claims the benefit of priority to U.S. application Ser. No. 16/027,804, entitled "Device for Subcutaneous Delivery of Fluid Medicament," filed on Jul. 5, 2018, which claims the benefit of priority to U.S. Provisional Patent Application No. 62/576,362 entitled "Device for Subcutaneous Delivery of Fluid Medicament," filed on Oct. 24, 2017 and to U.S. Provisional Patent Application No. 62/529,784 entitled "Delivery Device for a Fluid Medicament," filed on Jul. 7, 2017, the contents of all of which are incorporated herein by reference in their entireties.

TECHNICAL FIELD

The invention relates generally to systems and methods for medicament delivery and, more particularly, to a fluid medicament delivery device, and methods of using the same.

BACKGROUND

Delivery of medicaments, nutrients, or other liquid substances into the subcutaneous tissue of a patient is known to be an effective treatment technique for various medical conditions. Subcutaneous liquid administration may result in a more effective delivery of a substance into the circulatory system than other administration techniques (e.g., digestive tract, respiratory tract, etc.).

Subcutaneous delivery is often performed with an infusion pump. An infusion pump is typically a portable device carried by the patient that contains a medicament reservoir and drive components for delivering the medicament into the patient. Infusion pumps can deliver medicament in a more precise and controlled manner than can be accomplished with manual delivery by a patient or medical personnel. Infusion pumps are generally one of two types. The first type includes a standalone pump unit worn by a patient at a location remote from the delivery site (e.g., on a belt). The standalone pump unit pumps medicament from the reservoir through tubing to an infusion set attached to the patient's skin and accessing the subcutaneous tissue (e.g., via a flexible cannula). The second type is generally referred to as a "patch pump" and incorporates the medicament reservoir, drive components, and cannula all in a single unit adhered to the patient's skin. In some situations, infusion pumps deliver a continuous flow of medicament into a patient (sometimes called a basal dose). Infusion pumps can also deliver intermittent doses, in some cases controlled by the patient (sometimes called a bolus dose).

Given that subcutaneous medicament administration is typically performed with liquid substances, most infusion pump development has been for the treatment of medical conditions for which a liquid formulation medicament is therapeutically viable. The most prominent example is the use of infusion pumps for the subcutaneous delivery of insulin to patients with diabetes.

The most common medicament for the treatment of Parkinson's Disease is the drug levodopa, which is often administered in combination with the drug carbidopa. To date, therapeutic formulations of levodopa/carbidopa have only been available in solid or powder form and are typically administered with an oral pill or an inhaler product.

Recently, the Applicant has developed the first ever liquid formulation of levodopa/carbidopa having a therapeutic concentration appropriate for delivery to the subcutaneous tissue (described in greater detail in U.S. Patent Application Publication Nos. 2013/0253056 and 2014/0051755, which are incorporated by reference herein in their entireties). This discovery makes it practical, for the first time, to develop an infusion pump device for use by patients with Parkinson's Disease and other CNS disorders.

Individuals with Parkinson's Disease and other CNS disorders exhibit different symptoms than individuals with diabetes. In addition, the drug dosage volumes are different for different conditions. Thus, currently available infusion pumps designed for the treatment of diabetes or other conditions are often inappropriate and ineffective for the treatment of Parkinson's Disease. Accordingly, a need exists for a new drug delivery device appropriate for use by individuals with Parkinson's Disease or other CNS disorders.

SUMMARY

Accordingly, the present disclosure describes an improved medicament delivery devices, appropriate for delivering liquid medicaments to patients with Parkinson's Disease and other CNS disorders, and methods of using the same. Although this disclosure will sometimes refer to the delivery devices as delivering liquid formulations of levodopa/carbidopa to patients with Parkinson's Disease, it will be understood that the devices can be used to deliver other fluids, as well (liquid and gas). In general, the devices can be used for the delivery of any fluid medicament for the treatment of any medical condition, as well as for the delivery of non-drug fluids, e.g., nutrients, vitamins, imaging agents, etc. In addition, although this disclosure will often describe the delivery devices as performing subcutaneous injections, in some embodiments the devices can perform other types of injections, e.g., intravenous, intra-arterial, intra-articular, intramuscular, etc.

More than 10 million people are living with Parkinson's Disease worldwide. Common symptoms of Parkinson's Disease include tremor, slowness of movement, muscle stiffness, balance problems, dizziness, and problems sleeping (fatigue). In some embodiments, the drug delivery devices described herein are designed to be easier to use than conventional devices for patients exhibiting some or all of these symptoms. As one example, many conventional devices require the patient to navigate a syringe needle into a relatively small septum opening and manually force medicament out of the syringe in order to fill the pump. In some embodiments, the device described herein uses a filling station and a vial adapter operable to receive a vial for filling the device, which requires less strength and/or dexterity than conventional approaches.

As another example, a conventional technique for inserting a cannula into the tissue (e.g., subcutaneous tissue) requires the patient to manually apply the insertion force. In some embodiments, the delivery device described herein uses at least one cannula insertion mechanism that drives one or more cannulas into the tissue with force exerted thereby. Such cannula insertion mechanism may include, for example, a mechanical displacement mechanism (e.g., a mechanical energy storage device such as, for example, a torsion spring), an electro-mechanical mechanism, a pneumatic mechanism, and/or an electromagnetic mechanism.

The cannula insertion mechanism may be adapted or configured to require significantly less force to be applied by the patient in order to ensure puncturing of the skin for allowing, for example, subcutaneous delivery of the drug. The amount of force to be required by the patient may, for example, range from about 3 Newton to about 50 Newton. While the discussion herein may refer to subcutaneous delivery of a fluid medicament, it is noted that this should by no means be construed in a limiting manner. In some cases, the fluid medicament may for example be delivered to other layers of the user's skin tissue and/or directly into the user's blood vessels.

In some examples, the device may comprise a plurality of cannulas (e.g., two cannulas, three cannulas or more) for delivering fluid medicament into the tissue. Optionally, the plurality of cannulas, when in an extended position, can engage the tissue simultaneously. The tip of the cannulas may be spaced at a given minimum distance apart from each other to reduce the likelihood of generating or alleviating skin-related conditions such as nodules, abscesses, hematomas and/or the like.

In some embodiments, the device may be operable to allow selectively delivering, via the plurality of cannulas, fluid medicament to the patient. For example, the cannulas may be employed in succession for delivering, via a selected cannula, a desired quantity of the fluid medicament within a certain time period. In cases where the device comprises only two cannulas, they may be used alternatingly.

In another example, the plurality of cannulas may be grouped into two or more sets of selectable cannulas, allowing employment of the two or more cannula sets in succession or in parallel for delivering a desired quantity of the fluid medicament to the patient within a given time period. If the plurality of cannulas comprises only two sets, then these two sets may be employed alternatingly. In case the plurality of cannulas are operably grouped into three or more sets of cannulas, the sets may be employed successively or in parallel, each set for a given time period. The time period for employing one set of cannulas may be the same as or differ from the employment time period of another set of cannulas.

In some embodiments, the device may have bolus and basal fluid medicament delivery capabilities. The device may be operable to allow for manual, semi-automatic and fully-automated control of bolus and basal delivery of the fluid medicament such as, for example, carbidopa and/or levodopa and/or levodopa prodrugs (e.g., levodopa-amide, levodopa phosphate, carbidopa phosphate) and/or apomorphine.

As yet another example, in some embodiments the delivery device includes a reusable part including a motor and control electronics and a disposable part including a medicament reservoir. While the general concept of having a reusable part and a disposable part is known, in conventional devices the attachment between the two parts can involve complicated mechanical schemes that can require significant strength and/or dexterity to engage and disengage. In some embodiments, the reusable part and disposable part of the device described herein are attached with attachment schemes that are comparatively simple to engage and disengage, for example, in a single-step procedure by employing, for example, magnetic and/or snap connections. In addition, in some embodiments, the disposable part includes a linear actuator such as, for example, a rotation-to-linear displacement mechanism. The linear actuator may comprise, for example, a nut for rotating a lead screw to drive a plunger through the medicament reservoir. In some instances, the nut can engage directly with a structure in the disposable part (e.g., a gear) to enable the attachment of the two parts. These example features and other features for improved medicament delivery devices are described in detail below.

It is noted that merely to simplify the discussion that follows, embodiments and examples may refer to driving "a plunger". However, this should by no means be construed in a limiting manner. Accordingly, the device may in some embodiments be operable to drive a seal member through the medicament reservoir. In some examples, a seal member may be operably coupled with a plunger. Optionally, a seal member may be integrally formed with a plunger. Optionally, a distal end of a plunger may terminate in a seal member.

In some embodiments, the device is operable to selectively drive a plunger in a first direction to force fluid out of the reservoir for, e.g., subcutaneous delivery of the fluid medicament, and in an opposite direction to generate a suction force that draws fluid medicament back into the reservoir.

In some embodiments, a reservoir that is operable to contain fluid may be a selectively compressible (e.g., squeezable) and expandable reservoir. Compressing such reservoir may force fluid out of the reservoir for delivery to the user, and expanding such reservoir may generate a suction force drawing fluid back into the reservoir. Accordingly, the device may be adapted or configured to be "plunger-less." In other words, the device may free of a translating plunger and/or seal member.

In some embodiments, control of the device to selectively force fluid out of a reservoir or to generate a suction force to draw fluid back into the reservoir may, for example, depend on measured physiological or other parameter values. For example, the device may force fluid out of the reservoir for delivery to the user as long as one or more physiological parameter values meet a certain "delivery criterion". On the other hand, if the one or more physiological parameter values later meet a certain "suction criterion", the device may stop forcing fluid out of the reservoir and generate a suction force instead.

In one aspect, the invention relates to a device for delivering a fluid medicament to subcutaneous tissue of a user. The device can include (i) a reusable part that includes a drive component, and a control unit for controlling the drive component; and (ii) a disposable part attachable to the reusable part, the disposable part including a reservoir for containing the fluid medicament, a plunger for driving the fluid medicament out of the reservoir, a lead screw attached to the plunger, and a nut operable to displace the lead screw, such that when the reusable part and the disposable part are attached, the nut operably engages with the drive component, e.g., via a drive train that is coupled with the drive component.

In some embodiments of the above aspect, the reservoir can contain a fluid medicament including a liquid formulation of levodopa and/or carbidopa. The reusable part can further include a battery for powering the drive component (e.g., a motor assembly, which can include a motor and a planetary gear, a chain transmission, a belt transmission, a pneumatic transmission, a magnet-based transmission, and/or the like). In some cases, the drive train includes at least one gear (e.g., a drive gear, an idler gear, and a load gear in series). The nut can have a profile operable to engage with a mating profile of the load gear.

In some embodiments, the disposable part can further include an exterior surface operable to be adhered to a skin surface of the user. Micro dermal anchors can be attached to the exterior surface for adhering the device to the skin surface. In some cases, the exterior surface is adhered to the skin surface by a sub-pressure generated therebetween. The device can also include an adhesive layer adhered to the exterior surface, where a skin surface side of the adhesive layer includes continuous adhesive and an opposing device side of the adhesive layer includes discontinuous adhesive.

In some embodiments, the disposable part further includes a cannula fluidically coupled with the reservoir, such that, when the cannula operably engages with the patient's tissue, the cannula delivers the fluid medicament to the subcutaneous tissue of the user. The reusable part and the disposable part can be attached using a magnetic force and/or a snap connection. In some instances, when the reusable part and the disposable part are attached, the drive component and the reservoir are co-planar. In some cases, when the reusable part and the disposable part are attached, a longitudinal axis of the drive component is substantially parallel with a longitudinal axis of the reservoir. In some cases, when the reusable part and the disposable part are attached, the drive component and the reservoir overlap in a longitudinal direction by at least 50 percent.

In some embodiments, the disposable part can further include a second reservoir for containing additional fluid medicament, a second plunger for driving the additional fluid medicament out of the second reservoir, a second lead screw attached to the second plunger, and a second nut operable to displace the second lead screw, such that when the reusable part and the disposable part are attached, the second nut is coupled with the drive component. In some instances, the drive component simultaneously drives both of the first and second plungers. In other instances, the drive component separately drives each of the first and second plungers. The plunger can include a fluid-contacting surface made from an elastic material. In certain configurations, the reusable part forms a void for receiving the lead screw when the lead screw is retracted from the reservoir.

In some embodiments, the reusable part can further include a computing unit that monitors operation of the device. The reusable part can also include a control button to allow a user to select a mode of operation of the device (e.g., a priming mode, a delivery mode, and/or a pause mode). In some embodiments, the device can include a fluid sensor for sensing fluid medicament (e.g., for the detection of fluid and/or for measuring quantity and/or volume thereof) in the reservoir and/or a contact sensor for sensing contact between an exterior surface of the disposable part and a skin surface of the user. In some cases, the fluid sensor and/or contact sensor can for example include a capacitance sensor. The contact sensor can measure an electrical resistivity between at least two locations on the device. In some configurations, the fluid sensor is disposed along the reservoir and substantially parallel to the skin surface of the user. The fluid sensor and the contact sensor can be the same component.

In some embodiments, the device further includes a connection sensor (e.g., a hall effect sensor) for determining a connection between the reusable part and the disposable part. In some instances, the device further includes a physiological sensor for sensing at least one physiological characteristic of the user. Examples of the physiological sensor include (i) a temperature sensor for measuring a skin temperature of the user, (ii) a conductivity sensor for measuring a sweat level of the user, (iii) a movement sensor for measuring body motion of the user, (iv) a neural activity sensor, (v) an oxygen saturation level sensor, (vi) a blood analyte sensor (e.g., haemoglobin, cholesterol, glucose, etc.); (vii) a sound sensor for measuring bowel activity, (viii) an ECG sensor for detecting a heart rate of the user, and/or (ix) an EMG sensor for detecting a muscle spasm of the user. In some instances, the device further includes a functionality sensor for sensing at least one functional parameter of the device. Examples of the functionality sensor include a flow rate sensor, a pressure sensor, a DC current sensor, and/or a temperature sensor. In some embodiments, the fluid medicament can include levodopa.

In another aspect, the invention relates to a method for delivering a fluid medicament to subcutaneous tissue of a user. The method can include the steps of (a) providing a device including (i) a reusable part having a drive component, and a control unit for controlling the drive component; and (ii) a disposable part attachable to the reusable part, the disposable part including a reservoir for containing the fluid medicament, a plunger for driving the fluid medicament out of the reservoir, a lead screw attached to the plunger, and a nut operable to displace the lead screw, such that when the reusable part and the disposable part are attached, the nut is operably coupled with the drive component, e.g., via a drive train; (b) fluidically coupling the device to the subcutaneous tissue of the user; and (c) controlling the device such that the fluid medicament is delivered from the device to the subcutaneous tissue of the user.

In some embodiments of this aspect, the reservoir contains the fluid medicament that includes a liquid formulation of levodopa and/or carbidopa. The reusable part can include a battery and the method can further include powering the reusable part with the battery. The drive component can include a motor assembly (e.g., a motor and a planetary gear). The drive train can include at least one gear (e.g., a drive gear, an idler gear, and a load gear in series). In some instances, the nut has a profile operable to engage with a mating profile of the load gear.

In some embodiments, the fluidically coupling step includes adhering an exterior surface of the disposable part to a skin surface of the user. The adhering step can further include adhering micro dermal anchors attached to the exterior surface to the skin surface. The adhering step can also include generating a sub-pressure between the exterior surface and the skin surface. In some cases, the adhering step can include adhering an adhesive layer adhered to the exterior surface to the skin surface, where the skin surface side of the adhesive layer includes continuous adhesive and an opposing side of the adhesive layer include discontinuous adhesive.

In some embodiments, the fluidically coupling step includes inserting a cannula fluidically coupled with the reservoir into the subcutaneous tissue. In some cases, the method can include, before fluidically coupling the device to the subcutaneous tissue, attaching the reusable part and disposable part using, for example, a magnetic connection and/or a snap connection. The attaching step can include attaching the reusable part and disposable part such that the drive component and the reservoir are co-planar. In some instances, the reusable part and disposable part can be attached such that a longitudinal axis of the drive component is substantially parallel with a longitudinal axis of the reservoir and/or such that the drive component and the reservoir overlap in a longitudinal direction by at least 50 percent.

In some embodiments, the disposable part can further include a second reservoir for containing additional fluid medicament, a second plunger for driving additional fluid medicament out of the second reservoir, a second lead screw attached to the second plunger, and a second nut operable to displace the second lead screw, such that when the reusable part and the disposable part are attached, the second nut is coupled with the drive component. In some instances, the step of controlling the device such that the fluid medicament is delivered includes simultaneously driving both of the first and second plungers. In other instances, the step of controlling the device such that the fluid medicament is delivered includes separately driving both of the first and second plungers. In some cases, the plunger includes a fluid-contacting surface made from an elastic material. In some cases, the reusable part forms a void for receiving the lead screw when the lead screw is retracted from the reservoir.

In some embodiments, the reusable part further includes a computing unit operable to monitor operation of the device. The reusable part can include a control button to allow the user to select a mode of operation of the device (e.g., a priming mode, a delivery mode, and a pause mode). In some instances, the method can further include sensing fluid medicament in the reservoir using a fluid sensor and sensing contact between an exterior surface of the disposable part and a skin surface of the user using a contact sensor. The fluid sensor and the contact sensor can include a capacitance sensor. The method can include measuring an electrical resistivity between at least two locations on the device using the contact sensor. The fluid sensor can be disposed along the reservoir and substantially parallel to the skin surface of the user. In some cases, the fluid sensor and the contact sensor are the same component.

In some embodiments, the method can further include sensing a connection between the reusable part and the disposable part using a connection sensor (e.g., a hall effect sensor). In some instances, the method can further include sensing at least one physiological characteristic of the user using a physiological sensor. Examples of the physiological sensor include (i) a temperature sensor for measuring a skin temperature of the user, (ii) a conductivity sensor for measuring a sweat level of the user, (iii) a movement sensor for measuring body motion of the user, (iv) a neural activity sensor, (v) an oxygen saturation level sensor, (vi) a blood analyte sensor (e.g., hemoglobin, cholesterol, glucose, etc.); (vii) a sound sensor for measuring bowel activity, (viii) an ECG sensor for detecting a heart rate of the user, and/or (ix) an EMG sensor for detecting a muscle spasm of the user. In some instances, the method can further include sensing at least one functional parameter of the device using a functionality sensor. Examples of the functionality sensor include a flow rate sensor, a pressure sensor, a DC current sensor, and/or a temperature sensor. In some embodiments, the fluid medicament can include levodopa.

In another aspect, the invention relates to another device for delivering a fluid medicament to subcutaneous tissue of a user. The device can include a pump module having at least one reservoir for containing the fluid medicament; and a cannula insertion mechanism attachable to the pump module, the cannula insertion mechanism including an insertion needle, a cannula assembly including a flexible cannula connected to a rigid fluidic link and detachably coupled with the insertion needle such that, when the flexible cannula is located in the subcutaneous tissue, the cannula assembly fluidically couples the reservoir to the subcutaneous tissue via the rigid fluidic link.

In some embodiments of this aspect, the cannula insertion mechanism further includes a delivery mechanism including, for example, a spring (e.g., a torsion spring) coupled with the insertion needle, where release of the spring causes (i) delivery of the insertion needle and the cannula into the subcutaneous tissue and (ii) removal of the insertion needle from the subcutaneous tissue while leaving the cannula within the subcutaneous tissue. In some cases, the pump module further includes a plunger for driving the fluid medicament out of the reservoir, a drive component operable to drive the plunger in the reservoir, and a control unit for controlling the drive component. In some cases, the delivery mechanism and the insertion needle are removed from the pump module after the cannula is located in the subcutaneous tissue. The device can further include at least one additional cannula insertion mechanism adapted to insert at least one additional cannula into the subcutaneous tissue to fluidically couple the reservoir to the subcutaneous tissue. In some cases, the at least one reservoir can include more than one reservoir. The cannula insertion mechanism can also be operable to deliver more than one cannula into the subcutaneous tissue, such that at least one cannula couples each reservoir to the subcutaneous tissue. In some instances, the cannula insertion mechanism can include more than one cannula insertion mechanism, such that each reservoir has a corresponding cannula insertion mechanism operable to deliver at least one cannula into the subcutaneous tissue, such that at least one cannula couples each reservoir to the subcutaneous tissue. In some instances, each reservoir delivers the medicament to a different injection site on the user. In some cases, all of the reservoirs deliver the fluid medicament simultaneously. In some such cases, at least two of the reservoirs contain a different fluid medicament. In other cases, at least two reservoirs deliver the fluid medicament at a different time from each other. In some such cases, at least two of the reservoirs contain a different medicament.

In some embodiments, the device further includes a temperature control unit operable to control a temperature of the fluid medicament. For example, the temperature of the fluid medicament can be controlled to be within a temperature range of about 8-15 degrees Celsius, about 22-37 degrees Celsius, and/or about 32-42 degrees Celsius (among many other examples). The temperature control unit can be operable to heat and/or cool the fluid medicament contained within the reservoir. The temperature control unit can also be operable to heat and/or cool the fluid medicament, when the fluid medicament is within the cannula. The temperature control unit can include at least one of a heating element and a cooling element. The temperature control unit can include an apparatus for thermally isolating or insulating the fluid medicament from at least one of a body temperature of the user and an ambient temperature. In some instances, the temperature control unit includes a temperature sensor for sensing the temperature of the fluid medicament (e.g., at a tip of the cannula). In some cases, the temperature control unit employs thermoelectric techniques. In some embodiments, the device may be operable to adaptively delivery fluid, based on a measured physiological characteristic of the user such as, for example, the patient's body temperature. In some embodiments, the device may comprise an active heat pump assembly for removing heat, e.g., from the patient's skin, the reservoir(s), the disposable part, the reusable part, the fluid medicament, etc.

In some embodiments, the device further includes a skin property control unit. In some cases, the skin property control unit can apply ultrasonic vibration to an injection site. In certain instances, the cannula can form a delivery aperture in a side wall of the cannula. In some embodiments, the cannula can form a plurality of delivery apertures, each delivery aperture being formed at a different height along a side wall of the cannula. The cannula can be formed from stainless steel, silicon, carbon fiber, PTFE, and/or combinations thereof. The cannula can include a surface coating (e.g., an oily substrate, a pain killer medicament, etc.) that reduces a trauma associated with insertion of the cannula. In some embodiments, the device further includes a penetration depth control unit that controls a depth that the cannula is inserted into the subcutaneous tissue. In some embodiments, the device further includes a tissue detection unit that detects a type of subcutaneous tissue proximate the cannula (e.g., dermis, muscle, fat, blood vessel, air, water, and/or combinations thereof, etc.). In some embodiments, the fluid medicament can include levodopa.

In another aspect, the invention relates to another method for delivering a fluid medicament to subcutaneous tissue of a user. The method can include the steps of (a) providing a pump module including at least one reservoir for containing the fluid medicament; (b) attaching a cannula insertion mechanism to the pump module, the cannula insertion mechanism including an insertion needle, a cannula assembly including a flexible cannula connected to a rigid fluidic link and detachably coupled with the insertion needle; and (c) fluidically coupling the pump module to the subcutaneous tissue of the user such that, the cannula assembly fluidically couples the reservoir with the subcutaneous tissue via the rigid fluidic link.

In some embodiments of this aspect, the cannula insertion mechanism can further include a delivery mechanism including, for example, a spring (e.g., a torsion spring) coupled with the insertion needle and the method can further include releasing the spring causing (i) delivery of the insertion needle and the cannula into the subcutaneous tissue and (ii) removal of the insertion needle from the subcutaneous tissue while leaving the cannula within the subcutaneous tissue. In some cases, the pump module can further include a plunger for driving the fluid medicament out of the reservoir, a drive component operable to drive the plunger in the reservoir, and a control unit for controlling the drive component. The method can further include removing the delivery mechanism and the insertion needle from the pump module after the cannula is located in the subcutaneous tissue. In some cases, the method can further include attaching at least one additional cannula insertion mechanism to the pump module, the additional cannula insertion mechanism operable to insert at least one additional cannula into the subcutaneous tissue to fluidically couple the reservoir to the subcutaneous tissue. In some cases, the at least one reservoir can include more than one reservoir. In some instances, releasing the torsion spring causes delivery of more than one cannula into the subcutaneous tissue, such that at least one cannula couples each reservoir to the subcutaneous tissue. The method can further include attaching at least one additional cannula insertion mechanism to the pump module, such that each reservoir has a corresponding cannula insertion mechanism operable to deliver at least one cannula into the subcutaneous tissue, such that at least one cannula couples each reservoir to the subcutaneous tissue. In some instances, each reservoir can deliver fluid medicament to a different injection site on the user. In some cases, all of the reservoirs deliver the fluid medicament simultaneously. In some such cases, at least two of the reservoirs contain a different medicament. In some cases, at least two reservoirs deliver the fluid medicament at a different time from each other. In some such cases, at least two reservoirs contain a different fluid medicament.

In some embodiments, the method can further include controlling a temperature of the fluid medicament using a control unit (e.g., a heating element and/or a cooling element). For example, the temperature of the fluid medicament can be controlled to be within a temperature range of about 8 to about 15 degrees Celsius, from about 22 to about 37 degrees Celsius, and/or from about 32 to about 42 degrees Celsius (among many other examples). The temperature controlling step can include heating and/or cooling the fluid medicament contained within the reservoir. The temperature controlling step can also include heating and/or cooling the fluid medicament, when the fluid medicament is within the cannula. The temperature controlling step can also include thermally isolating the fluid medicament from at least one of a body temperature of the user and an ambient temperature. In some cases, the method includes sensing the temperature of the fluid medicament (e.g., at a tip of the cannula) using the temperature control unit. In some cases, the controlling the temperature step includes using thermoelectric techniques.

In some embodiments, the method further includes controlling a skin property of the user using a skin property control unit. The controlling the skin property step can include applying ultrasonic vibration to an injection site. In some instances, the cannula can form a delivery aperture in a side wall of the cannula. In some cases, the cannula forms a plurality of delivery apertures, each delivery aperture being formed at a different height along a side wall of the cannula. The cannula can be formed from stainless steel, silicon, carbon fiber, PTFE, and/or combinations thereof. The cannula can include a surface coating (e.g., an oily substrate, a pain killer medicament, etc.) that reduces a trauma associated with insertion of the cannula. In some instances, the method can further include controlling a depth that the cannula is inserted into the subcutaneous tissue using a penetration depth control unit. In some instances, the method can further include detecting a type of subcutaneous tissue proximate the cannula using a tissue detection unit (e.g., dermis, muscle, fat, blood vessel, air, water, and/or combinations thereof, etc.). In some embodiments, the fluid medicament can include levodopa.

In another aspect, the invention relates to a control unit for a device delivering a fluid medicament to a subcutaneous tissue of a user. The device can include a fluid medicament drive component, at least one patient sensor for detecting a medical condition status of the user, and a clock. The control unit can include a drive component module operable to control the drive component and deliver the fluid medicament based on signals received from both the patient sensor(s) and/or the clock.

In some embodiments of this aspect, the drive component includes a motor. The signals received from the patient sensor can include a sleep condition of the user, a food consumption measure for the user, and/or an exercise measure for the user. In some cases, the sleep condition of the user includes a sleep stage of the user, and the drive component module is operable to control the drive component and deliver the fluid medicament based on the sleep stage. The patient sensor for detecting the exercise measure for the user can include an ECG sensor and/or an accelerometer. The patient sensor for detecting the food consumption measure for the user can include a sound sensor. The signals received from the clock can include the time of day. In some instances, the drive component module is further operable to control a volume of fluid medicament delivered to an injection site during a particular time period. In some instances, the drive component module is further operable to deliver fluid medicament intermittently including at least one on period and at least one off period. The device can further include a pressure sensor operable to sense a pressure of the fluid medicament, and the drive component module can be further operable to control the drive component based on a signal received from the pressure sensor. In some embodiments, the fluid medicament can include levodopa.

In another aspect, the invention relates to a method of controlling a device delivering a fluid medicament to a subcutaneous tissue of a user. The device can include a fluid medicament drive component, at least one patient sensor for detecting a medical condition status of the user, and a clock. The method can include the steps of receiving a signal from the patient sensor(s), receiving a signal from the clock, and controlling the drive component to deliver the fluid medicament based the signals received from both the patient sensor(s) and the clock.

In some embodiments of this aspect, the drive component can include a motor. The signal received from the patient sensor can include a sleep condition of the user, a food consumption measure for the user, an exercise measure for the user, and/or a weight of the user. In some cases, the sleep condition of the user includes a sleep stage of the user, and the drive component module is operable to control the drive component and deliver the fluid medicament based on the sleep stage. The patient sensor for detecting the exercise measure for the user can include an ECG sensor and/or an accelerometer. The patient sensor for detecting the food consumption measure for the user can include a sound sensor. The signal received from the clock can include a time of day. In some instances, the method further includes controlling a volume of fluid medicament delivered to an injection site during a particular time period. The method can also include controlling the drive component to deliver fluid medicament intermittently including at least one on period and at least one off period. The method can also include sensing a pressure of the fluid medicament using a pressure sensor, where the controlling step can further include controlling the drive component based on a signal received from the pressure sensor. In some embodiments, the fluid medicament can include levodopa.

In another aspect, the invention relates to a charging/filling station for a device operable to deliver a fluid medicament to a subcutaneous tissue of a user. The charging/filling station can include a cradle for receiving the device, a charging unit operable to charge a rechargeable battery of the device, a display, and a communication module operable to instruct at least one of a control unit and a drive component of the device to initiate a filling operation of the device.

In some embodiments of this aspect, the device includes a medicament reservoir and the cradle is operable to hold the device within the reservoir, e.g., in a substantially vertical orientation. Optionally, the cradle may comprise a connection or proximity sensor configured to detect the operable positioning of the device in the cradle. Responsive to detecting the presence of the device in the cradle, the filling station may provide an output prompting the user to authorize starting a battery charging sequence. Alternatively, responsive to detecting the presence of the device in the cradle, the filling station may automatically initiate a battery charging sequence.

In some embodiments, vial adapters(s) (described below) may comprise a connection or proximity sensor which is configured to detect operable coupling of a vial to a vial adapter. Responsive to detecting operable coupling of a vial to the vial holder, and provided that the device is operably positioned in the cradle, the filling station may provide an output prompting the user to initiate a vial charging sequence. Alternatively, responsive to detecting the operable coupling of a vial to the vial adapter, the filling station may automatically initiate a vial filling charging sequence, provided that the device is operably positioned in the cradle.

The term "the device is operably positioned in the cradle" may, for instance, refer to an orientation of the device in the cradle as well as to the orientation of the device relative to world coordinates. For example, the device may be considered to be in "operable position" when in certain orientation relative to the earth's field of gravity, e.g., such that fluid medicament could flow, merely through gravity, from a vial into the device's reservoir(s).

In some cases, the charging unit charges the battery wirelessly. The display can include an LED display. The display can include a graphical user interface, which can enable a user to input an instruction to initiate the filling operation. In some cases, the display further includes a touchscreen. In some cases, the communication module can communicate with a computing device via a wired and/or a wireless communication network (not shown).

A used herein, a computing device may include, for example, a multifunction mobile communication device also known as a "smartphone", a personal computer, a laptop computer, a tablet computer, a server (which may relate to one or more servers or storage systems and/or or services associated with a business or corporate entity, including for example, a file hosting service, cloud storage service, online file storage provider, peer-to-peer file storage or hosting service and/or a cyberlocker), personal digital assistant, a workstation, a wearable device, a handheld computer, a notebook computer, a vehicular device, a stationary device and/or a home appliances control system.

The communication module may, for example, include I/O device drivers (not shown) and network interface drivers (not shown) for enabling the transmission and/or reception of data over a communication network for enabling external communication with the communication device. A device driver may for example, interface with a keypad or to a Universal Serial Bus (USB) port. A network interface driver may for example execute protocols for the Internet, or an Intranet, Wide Area Network (WAN), Local Area Network (LAN) employing, e.g., Wireless Local Area Network (WLAN), Metropolitan Area Network (MAN), Personal Area Network (PAN), extranet, 2G, 3G, 3.5G, 4G including for example Mobile WIMAX or Long Term Evolution (LTE) advanced, 5G, Bluetooth® (e.g., Bluetooth smart), ZigBee™, near-field communication (NFC) and/or any other current or future communication network, standard, and/or system.

The communication module can receive a medical condition status of the user, e.g., from the device and/or the cloud. In some instances, the display can display the medical condition status. The filling operation can include movement of a plunger through a medicament reservoir to generate a suction force to draw the fluid medicament from a vial into the medicament reservoir via a vial adapter. The communication module can be operable to instruct the device to initiate the filling operation when the device is within the cradle of the charging/filling station. In some embodiments, the fluid medicament can include levodopa.

In some embodiments, the device may be operable to allow a user to initiate drawing fluid from vial(s) into a medicament reservoir of the disposable part without necessarily requiring the employment of a filling station. For example, the device may include a user interface provided on the reusable and/or the disposable part, which allows the user to provide a command input causing the pump to rotate the drive component, which in turn may cause the displacement of the plunger and, therefore, the filling of the medicament reservoir.

In another aspect, the invention relates to a method of charging/filling a device operable to deliver a fluid medicament to a subcutaneous tissue of a user. The method can include the steps of receiving the device within a cradle, charging a rechargeable battery of the device with a charging unit, and instructing at least one of a control unit and a drive component of the device to initiate a filling operation of the device. The device's rechargeable battery and charging coil may be arranged within the housing of the reusable part at a desirable distance. For example, as far apart as practicably possible, e.g., to avoid damage to the battery by electromagnetic radiation that may be present in the coil's vicinity.

In some embodiments of this aspect, the method can further include holding the device within the cradle such that, when a fluid is contained in the medicament reservoir of the device, the fluid is subjected to the earth's gravity field to flow towards an outlet of the reservoir. In some instances, the charging step can include wirelessly charging the rechargeable battery. The device can include a display, which can include a graphical user interface and/or a touch screen. In some cases, the method can further include receiving an instruction to initiate the filling operation from a user interacting with the graphical user interface. The method can further include communicating information with a computing device via a wired and/or wireless network. In some cases, the method can include receiving a medical condition status of a user, e.g., from the device and/or the cloud. In some cases, the method can include displaying the medical condition status. The filling operation can include movement of a plunger through a medicament reservoir to generate a suction force to draw the fluid medicament from a vial into the medicament reservoir via a vial adapter. In some cases, the step of instructing the device to initiate the filling operation occurs when the device is within the cradle. In some embodiments, the fluid medicament can include levodopa.

In another aspect, the invention relates to a medicament vial adapter for use with a device for delivering a fluid medicament to subcutaneous tissue of a user. The device can include a reservoir for containing the fluid medicament. The medicament vial adapter can include a first port operable to connect to the reservoir, a second port operable to connect to a medicament vial containing the fluid medicament, and a needle disposed in the first and second ports, such that when the vial adapter is connected to the reservoir and the medicament vial, the needle fluidically couples the medicament vial to the reservoir.

In some embodiments of this aspect, the needle is operable to pierce (i) a septum disposed in the device to access the reservoir and (ii) a vial plug to access contents of the medicament vial. In some cases, the needle can include a metal material and can be operable to pierce the vial plug under an insertion force of no greater than about 10N. The needle can be shielded from inadvertent user contact. In some embodiments, the fluid medicament can include levodopa.

In another aspect, the invention relates to a method for filling a device for delivering a fluid medicament to subcutaneous tissue of a user. The device can include a reservoir for containing the fluid medicament. The method can include the steps of connecting a first port of a medicament vial adapter to the reservoir, connecting a second port of the medicament vial adapter to a medicament vial containing the fluid medicament, and disposing a needle in the first and second port to fluidically couple the medicament vial to the reservoir.

In some embodiments of this aspect, the needle is operable to pierce (i) a septum disposed in the device to access the reservoir and (ii) a vial plug to access contents of the drug vial. The needle can include a metal material and can be operable to pierce the vial plug under an insertion force of no greater than about 10N. In some cases, the method can further include shielding the needle from inadvertent user contact. In some embodiments, the fluid medicament can include levodopa.

In another aspect, the invention relates to a filling system that can include (i) a device for delivering a fluid medicament to subcutaneous tissue of a user, the device including a reservoir for receiving and containing the fluid medicament, and (ii) a vial adapter including a first port operable to connect to the reservoir, a second port operable to connect to a medicament vial containing the fluid medicament, and a needle disposed in the first and second ports, wherein when the vial adapter is connected to the reservoir and the medicament vial, the needle fluidically couples the medicament vial to the reservoir.

In another aspect, the invention relates to a holder for securing a pump device to a user. The holder can include a receiving portion operable to receive the pump device and detachably retain the pump device, an attachment component for attaching the holder to the user and/or an article of apparel (e.g., clothing) worn by the user, and a position altering component inter disposed between the receiving portion and the attachment component to alter a position and/or orientation of the pump relative to the attachment component.

In some embodiments of this aspect, the position altering component is operable to change the orientation of the pump device to multiple angular positions, and/or the position of the pump device. In some cases, the pump device includes external tubing and the position altering component is operable to rotate the pump device to advantageously position the tubing. In some cases, the attachment component can include a clip operable to clip onto a belt worn by the user. The receiving portion can include a quick release coupling.

In another aspect, the invention relates to a method for securing a pump device to a user. The method can include the steps of receiving and detachably retaining the pump device on a holder, attaching the holder to at least one of the user and an article of clothing worn by the user, and altering a relative position of the pump device using a position altering component on the holder.

In some embodiments of this aspect, the altering the relative position step includes rotating the pump device to multiple angular positions. In some cases, the pump device includes external tubing and the rotating the pump device step includes rotating the pump device to advantageously position the tubing. In some cases, the attaching the holder step includes attaching a clip of the holder onto a belt worn by the user. In some cases, the receiving and detachably retaining step includes using a quick release coupling.

In some aspects, the device may include a cannula part, a reservoir part, and a control and drive part, all, some, or none of which can be the same as or have common features with the disposable and/or reusable parts described above. The cannula part includes the cannula which is operable to engage with the patient's skin to subcutaneously deliver a fluid medicament. The reservoir part includes the medicament reservoir operable to receive the fluid medicament from a vial. The control and drive part includes the motor and control electronics for controlling the delivery of the fluid medicament from the reservoir via the cannula to a subcutaneous tissue site.

The cannula part may be detachably and operably couple-able with the reservoir part such that the cannula of the cannula part is in fluid communication with the reservoir of the reservoir part. The control and drive part may be detachably and operably coupleable with the reservoir part such that the control electronics and the drive can control the operation of delivery of fluid from the medicament reservoir.

The cannula part, the reservoir part and/or the control and drive part may be reusable or disposable or both reusable and disposable.

This Summary introduces a selection of concepts in a simplified form that are further described below in the Description of the Figures and the Detailed Description. This Summary is not intended to identify key features or essential features of the claimed subject matter, nor is it intended to be used to limit the scope of the claimed subject matter.

BRIEF DESCRIPTION OF THE FIGURES

In the drawings, like reference characters generally refer to the same parts throughout the different views. Also, the drawings are not necessarily to scale, emphasis instead generally being placed upon illustrating the principles of the invention. In some cases, references to previously presented elements are implied without necessarily further citing the drawing or description in which they appear. The number of elements shown in the drawings should by no means be construed as limiting and is for illustrative purposes only. In the following description, various embodiments of the present invention are described with reference to the following drawings, in which:

FIGS. 8A-8B are schematic, 3D views illustrating a snap connection between the disposable part and the reusable part, according to some embodiments;

FIGS. 10A-10C are schematic, 3D views showing the medicament delivery device with multiple reservoirs, according to some embodiments;

FIGS. 15A-15G are schematic illustrations of various configurations and techniques for charging the delivery device, according to some embodiments;

FIG. 16 is a schematic, 3D view of a standalone pump unit and an infusion set, according to some embodiments;

FIGS. 21A-21C are schematic illustrations of a cannula insertion mechanism, according to some embodiments;

FIGS. 22A-22B are schematic illustrations of a cannula having side wall apertures, according to some embodiments;

FIGS. 24A-24E are schematic illustrations of another cannula insertion mechanism, according to some embodiments;

FIGS. 25A-25E are schematic illustrations of various delivery device configurations having multiple reservoirs and/or multiple cannulas, according to some embodiments;

FIGS. 29A-29C are schematic, 3D views of a skin/tissue property control unit and a skin/tissue detection unit of the delivery device, according to some embodiments;

FIG. 33 is a chart listing example values for parameters related to the configuration and operation of the medicament delivery device, according to some embodiments;

FIGS. 34B-34J schematically show various embodiments of liquid quantity sensor devices operably coupled with reservoirs;

FIG. 37A schematically shows a liquid quantity sensor device that is operably coupled with a reservoir, according to some embodiments;

FIG. 37B schematically shows a side view of a reusable part of the device comprising a liquid quantity sensor device, according to some embodiments;

FIG. 37C schematically shows a partial sectional top view of the reusable part, according to some embodiments;

FIG. 37D schematically shows an enlarged view of the partial sectional top view of FIG. 37C with the liquid quantity sensor device;

FIG. 37G schematically shows front and back views of a capacitor-based liquid quantity sensor, according to some embodiments;

FIG. 37H is a schematic block diagram illustration of a capacitor-based liquid quantity measurement system, according to some embodiments;

DETAILED DESCRIPTION

Figure 1:
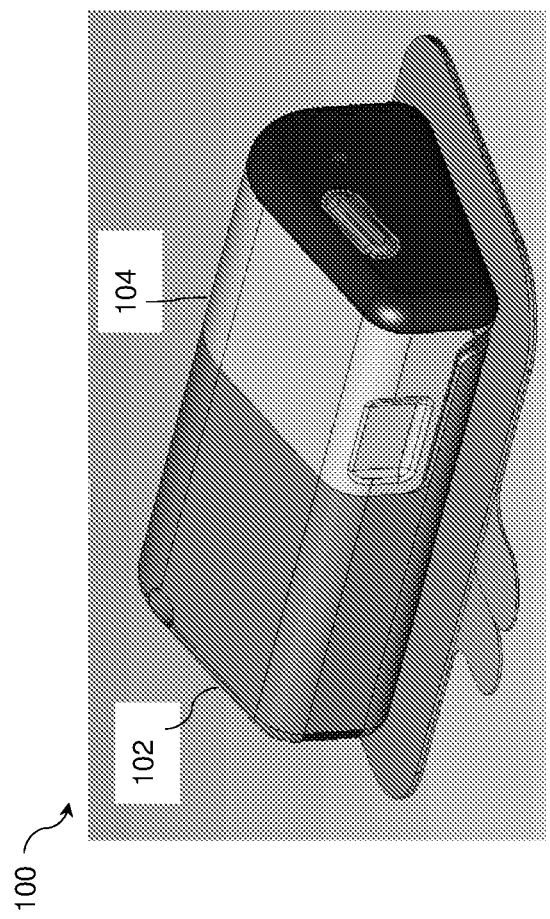
FIG. 1 is a schematic, transparent 3D view of a medicament delivery device, according to some embodiments.
Figure 2:
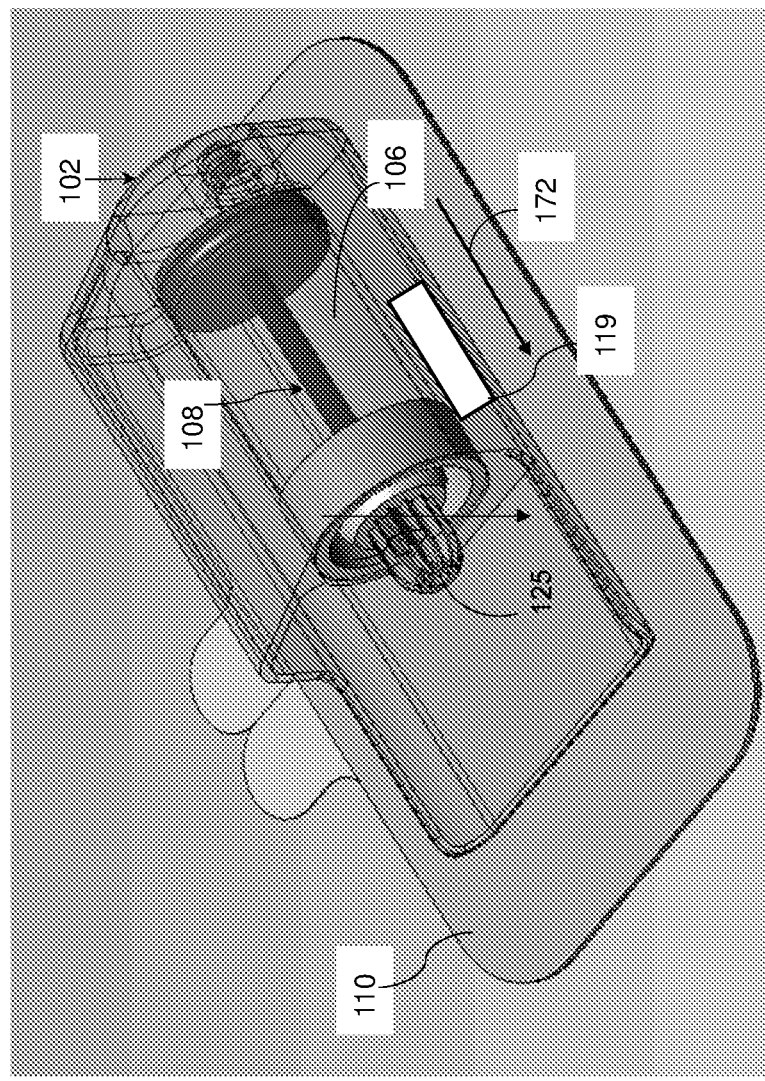
FIG. 2 is a schematic, transparent 3D view of a disposable part, according to some embodiments.
Figure 3:
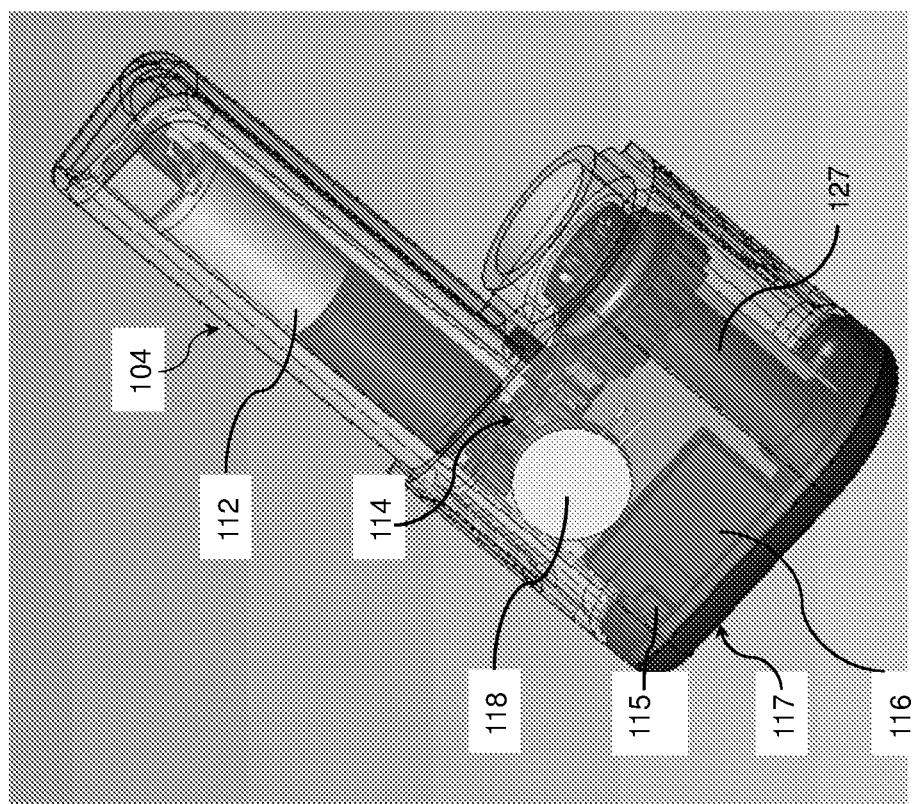
FIG. 3 is a transparent schematic 3D view of a reusable part, according to some embodiments.

Embodiments of the present invention relate to an improved device for the subcutaneous delivery of medicament to a patient. In some embodiments, the device can take the form of either a patch pump or a standalone pump used with an infusion set. FIG. 1 shows an example patch pump 100 that includes a disposable part 102 and a reusable part 104. A transparent view of the example disposable part 102 is shown in FIG. 2. As shown, the disposable part 102 includes a medicament reservoir 106, a plunger assembly 108, and an adhesive portion 110 for attachment to a patient's skin. A transparent view of the example reusable part 104 is shown in FIG. 3. As shown, the reusable part 104 can include a drive component 112 (e.g. a motor (DC or AC)), a drive train 114 (e.g., a gear train), a memory unit 115, a control unit 116, and a power supply 118 (e.g., a battery). In some embodiments, the disposable part 102 may comprise a power supply 119.

In some cases, the memory unit 115 and control unit 116 can be part of a single computing unit 117.

It will be appreciated that separate controllers and/or memory units can be allocated for each processing function and/or element (such as the device 100 and/or the filling station 154 (described below)). For simplicity, the following description will refer to computing unit 117 as a generic controller and memory unit that conduct all the necessary controlling and/or processing functions. In some cases, only the device 100 includes computing unit 117.

Each of the disposable part 102 and the reusable part 104 and how they engage and interact with each other are described in more detail below.

Figure 4A:
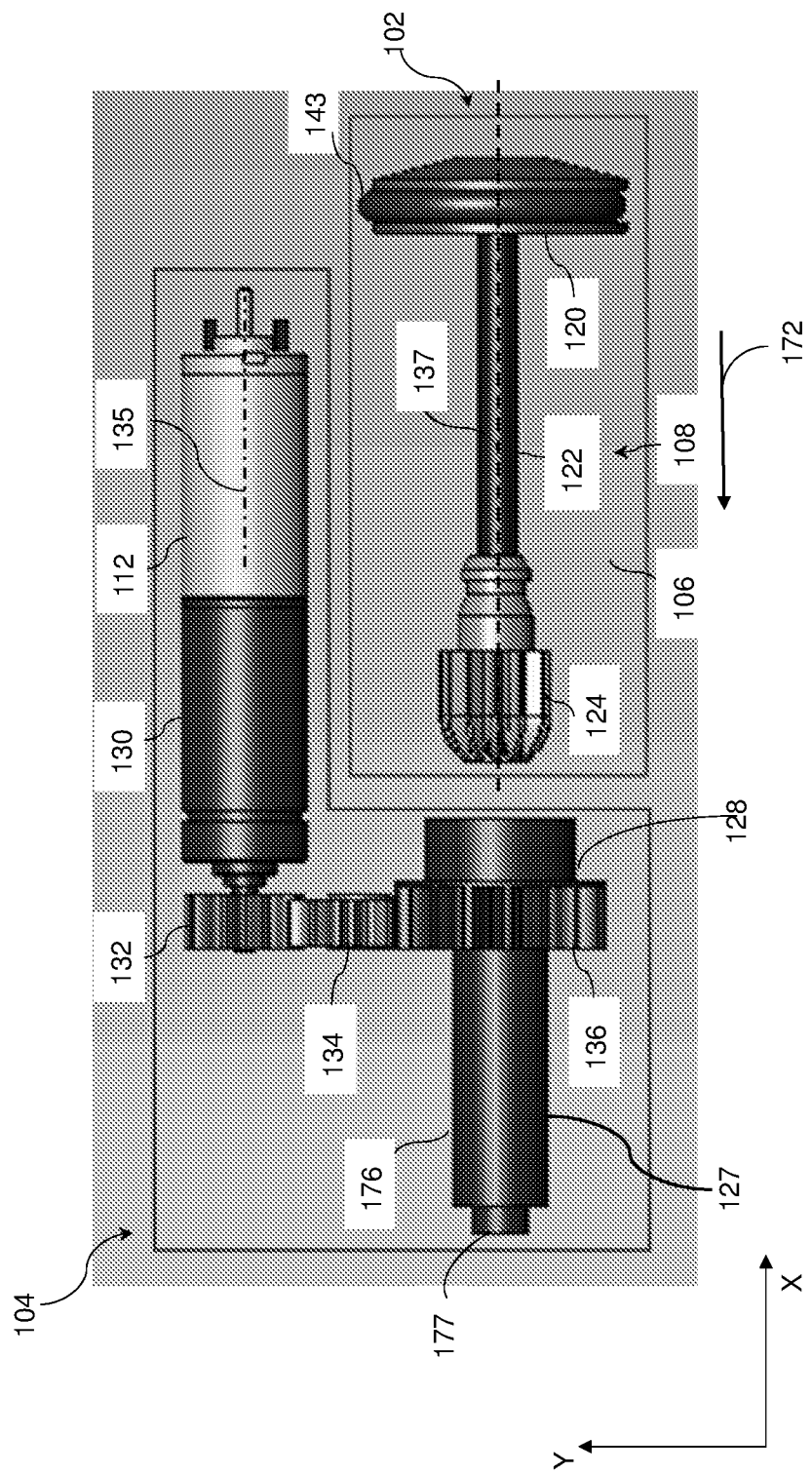
FIG. 4A is a schematic, side view illustrating how the disposable part and the reusable part fit together, according to some embodiments.
Figure 5:
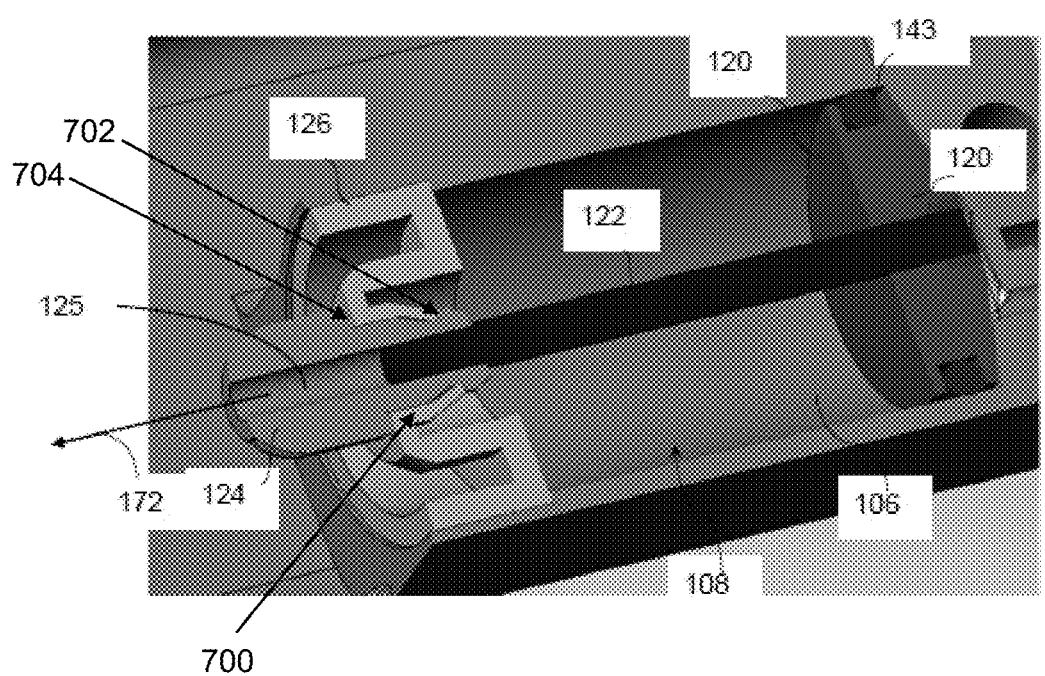
FIG. 5 is a schematic, cross-sectional 3D view of a plunger assembly within a medicament reservoir, according to some embodiments.

FIG. 4A is a schematic diagram illustrating how the disposable part 102 and reusable part 104 interact. As shown, in some embodiments, the plunger assembly 108 of the disposable part 102 includes a plunger head 120, a lead screw 122 attached to the plunger head 120 with substantially no rotational ability therebetween, and a nut 124 having an inner threaded profile that engages with threads on the lead screw 122. Rotation of the nut 124 can cause linear translation of the lead screw 122 such that the plunger head 120 is displaced in either direction through the reservoir 106, depending on the direction the nut 124 is rotated. In some instances, nut 124 has an opening 125 (see FIG. 5) to allow displacement of the lead screw 122 in a proximal direction 172 towards the reusable part 104. As depicted in FIG. 5 in some embodiments, the bushing 126 comprises a compliant portion 700 that permits the nut 124 a degree of lateral freedom of movement. In some embodiments, the nut 124 comprises a circumferential groove formed by a first circumferential ledge 702 and a second circumferential ledge 704 longitudinally opposite the first circumferential ledge 702, wherein the bushing 126 secures the nut 124 via a compliant portion 700 of the bushing 126 adapted to fit within the circumferential groove. In some embodiments, as described herein with respect to the nut 124 being rotatable within a bushing 126, the circumferential groove and the compliant portion 700 each comprise a rounded profile. In some embodiments, a cross-section perpendicular to a longitudinal axis of the nut 124 through the compliant portion 700 and the circumferential grooves forms two complete concentric circles.

Figure 4B:
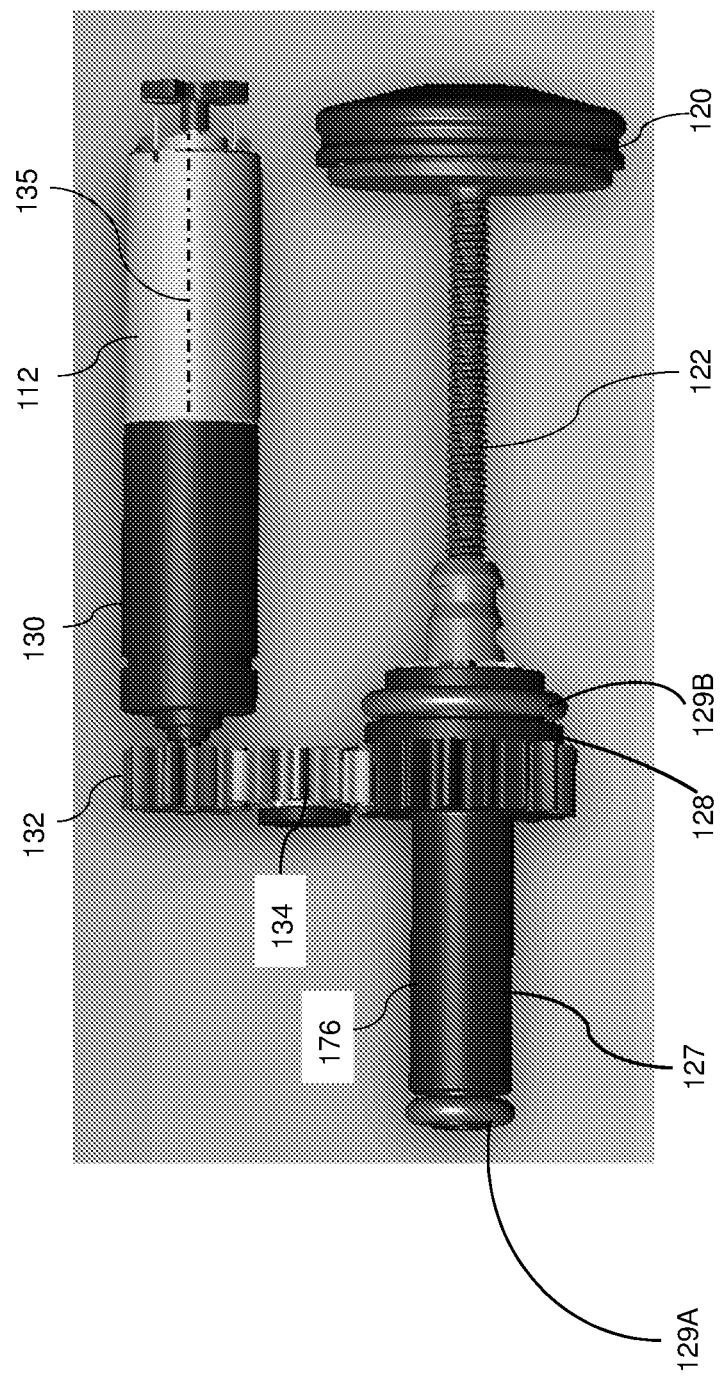
FIG. 4B is a schematic, side view illustrating a sealing arrangement of the disposable and the reusable part, according to some embodiments.

In some embodiments, the proximal side of the reusable part 104 has a screw-receiving tube cavity 127 formed in a sealing arrangement with the reusable part 104. When the disposable part 102 and the reusable part 104 are operably coupled with each other, the screw-receiving tube cavity 127 can be located opposite and oriented relative to the opening 125 such that their axes are substantially coinciding, and further such that the portion of the translated lead screw 122 protruding out of the opening 125 is received within the screw-receiving tube cavity 127. Optionally, the screw-receiving tube cavity 127 may be a rotation axis for a load gear 136, whose functionality is outlined herein in more detail. This configuration allows housing at least some or all electronic parts of the reusable part 104 in a sealed manner, thus protecting them from the environment external to the reusable part 104 while, at the same time, allowing proper functionality of the device during operation and control of the moving parts of the disposable part 102 through the electronic components of the reusable part 104. As shown in FIG. 4B, the sealing arrangement may be obtained by employing one or more O-rings. For example, a first O-ring 129A may be coupled with (e.g., disposed over) a proximal end of the screw-receiving tube cavity 127, and a second O-ring 129B may be coupled with (e.g., disposed over) a distal end of the screw-receiving tube cavity 127.

In some embodiments, screw-receiving tube cavity 127 can be open to the reservoir at both ends, thus enabling drainage of liquids when disassembled. In other embodiments, screw-receiving tube cavity 127 can also be closed at one or both ends, to prevent ingress of materials, for example, when the disposable part 102 and the reusable part 104 are assembled. In some embodiments, components of the device may be made or consist of inert material or materials having comparatively high elasticity such that after a force that caused deformation of the component is removed, the component attains its original form. For example, the component may exhibit comparatively non-plasticity characteristics and, for example, non-rigid characteristics. Optionally, plunger head 120 may be made of a single part which is compressibly confined within the reservoir to create liquid-sealing properties. Hence, in some embodiments, the plunger head 120 may be liquid sealing, but not include an O-ring. Additional or alternative components of the device may also not include an O-ring.

The nut 124 can be rotated within a bushing 126 (see FIG. 5). Displacement of the plunger head 120 in one direction can force medicament contained in the reservoir out of the reservoir into the patient (as described below). Displacement of the plunger head 120 in the other direction can create space in the reservoir (and, in some cases, generate a vacuum) to enable filling of the reservoir 106 (as described below). In some embodiments, linear translation to generate forces within the reservoir 106 (e.g., compressive forces to deliver fluid or suction forces to enable filling) are only performed by components within the disposable part 102 (e.g., the lead screw 122 and the plunger head 120). In such embodiments, the drive components within the reusable part 104 do not translate linearly within the reservoir 106.

Figure 6:
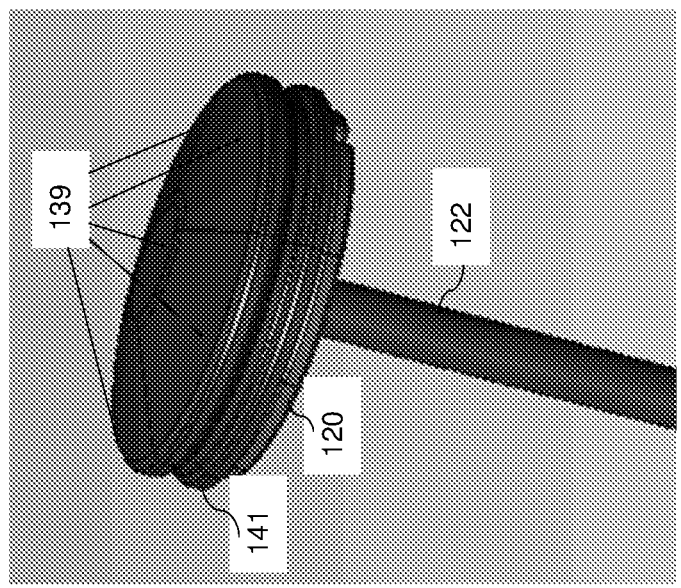
FIG. 6 is a schematic, 3D view of a plunger head with a cover, according to some embodiments.

As shown in FIG. 6, in some embodiments, the fluid contacting surface 139 of the plunger head 120 can be made from an elastic material that is safe to contact the fluids contained in the reservoir 106. The fluid contacting surface 139 can be defined as a surface that makes fluidic contact with the fluid contained in the reservoir 106, during either delivery or filling operations. The fluid contacting surface 139 can reduce or eliminate contact with the medicament by other materials (e.g., of other components of the device 100). In some instances, the fluid contacting surface 139 is formed from a cover 141 placed over the plunger head. In such instances, the cover 141 can serve as a seal that prevents fluid in the reservoir 106 from flowing past the plunger head 120. In some cases, in addition to or as an alternative from the cover 141 seal, an O-ring 143 (see FIG. 4A) (or gasket or other sealing mechanism) can be included on the plunger head 120.

Returning to FIG. 4A, in some embodiments, the nut 124 can be rotated via engagement with structure in the reusable part 104. As mentioned above, the reusable part 104 can include a drive component 112 for generating a force for driving the plunger assembly 108 (e.g., rotating the nut 124). In general the drive component 112 can be any component capable of generating this force; for example, a motor. The reusable part 104 can also include a drive train 114 for transferring the drive force from the drive component 112 to the plunger assembly 108. For example, the drive train 114 can be a gear train. As shown, the gear train can include a planetary gear 130 (e.g., for reducing the speed and increasing the moment of the motor), a drive gear 132 coupled with the planetary gear 130, an idler gear 134 coupled with the drive gear 132, and a load gear 136 coupled with the idler gear 134. Many different gear configurations are possible. Alternative drive train systems are also contemplated, e.g., belt and pulley systems, rack and pinion systems, etc.

In the configuration shown in FIG. 4A, the nut 124 can be detachably coupled with the load gear 136 to enable transfer of the drive force from the drive component 112 to the nut 124. In some embodiments, the nut 124 can include an outer profile that engages with a mating profile of the load gear 136. As depicted in FIG. 4A, the mating profile can be formed within a boss 128 protruding from the load gear 136. As mentioned above, the load gear 136 can transmit a force to nut 124 which can cause linear translation of lead screw 122 within the reservoir 106. In some instances, only components within the disposable part 102 translate linearly within the reservoir 106. Thus, in some embodiments, the load gear 136 does not translate linearly within the reservoir 106. Other techniques for detachably coupling the nut 124 to the load gear 136 are contemplated.

In some embodiments, when the disposable part 102 and the reusable part 104 are engaged, the drive component 112 and the reservoir 106 are co-planar. For example, as shown in FIG. 4A, the longitudinal axis 135 of the drive component 112 and the longitudinal axis 137 of the reservoir 106 are both within the same plane. In some instances, when the disposable part 102 and the reusable part 104 are engaged, the longitudinal axis 135 of the drive component 112 and the longitudinal axis 137 of the reservoir 106 are substantially parallel. In some instances, when the disposable part 102 and the reusable part 104 are engaged, the drive component 112 and the reservoir 106 can overlap in the longitudinal direction. The amount of overlap can be at least 30%, at least 40%, at least 50%, at least 60%, and/or at least 70% of the length of the drive component 112, or in some cases at least 30%, at least 40%, at least 50%, at least 60%, and/or at least 70% of the length of the reservoir 106. Each of the configurations described earlier in this paragraph can reduce the profile of the device 100, which can make the device 100 more wearable and discrete for the user. As one example, if the drive component 112 and the reservoir 106 were not co-planar and, for example, the longitudinal axis 135 were in the z axis, then the device would be much thicker and bulkier.

Figure 7C:
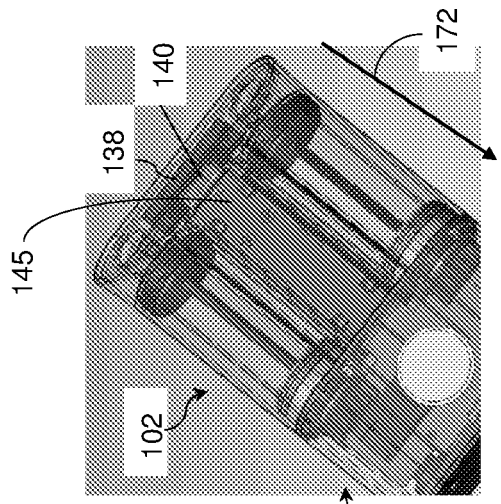
FIGS. 7A-7C are schematic, 3D views illustrating a magnetic connection between the disposable part and the reusable part, according to some embodiments.
Figure 7B:
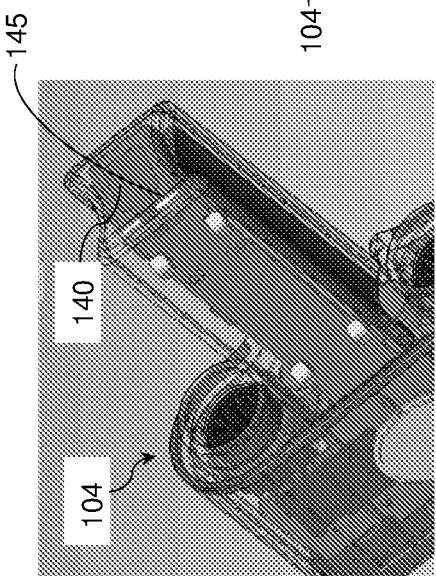
Figure 7A:
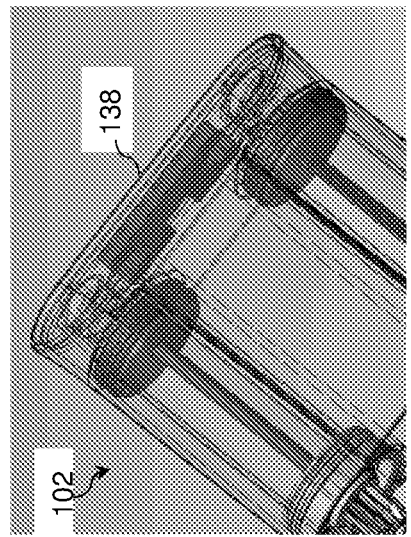
Figure 9A:
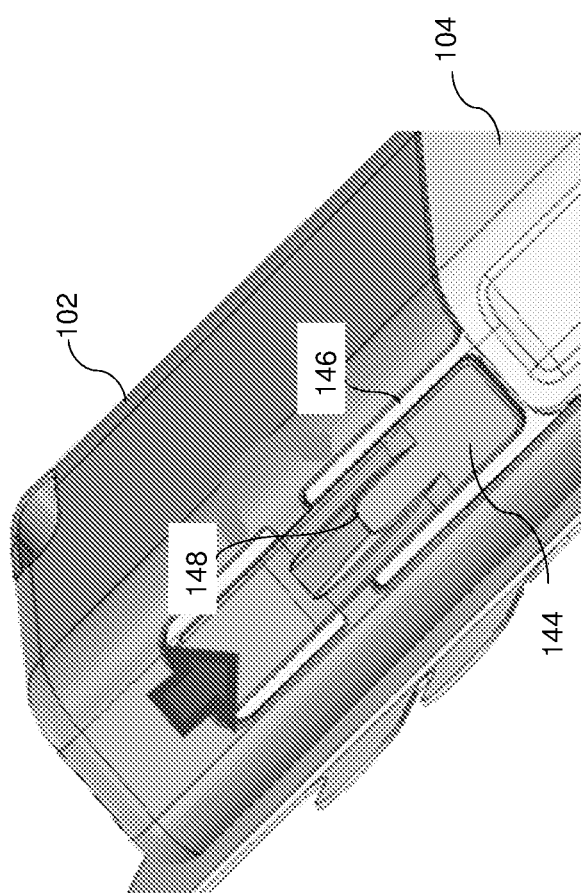
FIGS. 9A-9F are schematic, 3D views illustrating a swing latch connection between the disposable part and the reusable part, according to some embodiments.
Figure 9D:
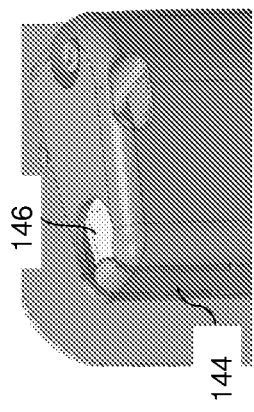
Figure 9C:
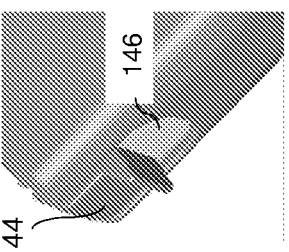
Figure 9B:
Figure 9F:
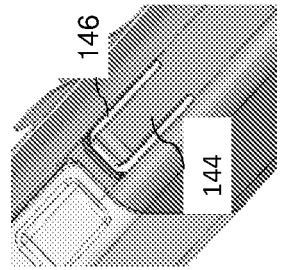
Figure 9E:
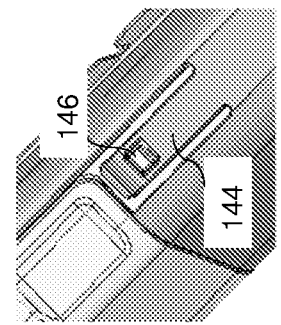

In addition to, or as an alternative from, the engagement between the nut 124 and the load gear 136, several techniques can be used for attaching the disposable part 102 and the reusable part 104. In some embodiments, the parts are attached using a magnetic force. As shown in FIGS. 7A-7C (depicting an embodiment including two medicament reservoirs, described below), a first magnet 138 of the disposable part 102 and a second magnet 140 of the reusable part 104 can be arranged to attract one another when the two parts are positioned together (e.g., such that the nut 124 engages the load gear 136). In some embodiments, the parts can be attached using a snap connection that uses a locking feature 142 to hold the parts together, as shown for example in FIGS. 8A-8B. In some embodiments, the parts are attached using a swing latch. As shown in FIG. 9A, the swing latch can include an arm 144 on the disposable part 102 that engages a corresponding groove 146 on the reusable part 104 to hold the parts together. The arm 144 can have a flexible hinge 148 that, when pressed, releases the arm 144 from the groove 146. In some instances, the arm 144 is on the reusable part 104 and the groove 146 is on the disposable part 102. Various alternate configuration and locations of the swing latch are shown in FIGS. 9B-9F.

Regardless of the connection technique employed, in general, the disposable part 102 and the reusable part 104 can be attached and detached at any time, regardless of the position of the plunger head 120 within the reservoir 106 or the amount of fluid in the reservoir 106. In some instances, the parts are detached when the reservoir 106 is empty and it is time to replace the disposable part 102, but the parts are not required to only be detached at that time.

In general, the reusable part 104 can be operably coupled with the disposable part 102 in any orientation relative to each other. With reference to FIGS. 10A-10C, in some embodiments, the reusable part 104 and the disposable part 102 can be attached such that nut 124*a* engages load gear 136*a* and nut 124*b* engages load gear 136*b*, and the reusable part 104 and the disposable part 102 can also be attached when rotated 180 degrees with respect to this orientation, e.g., such that nut 124*a* engages load gear 136*b* and nut 124*b* engages load gear 136*a*. In some instances, this feature can improve the usability of the device 100 because the patient need not ensure that the reusable part 104 and disposable part 102 are in the correct orientation before attaching the parts. In other embodiments, the reusable part 104 and the disposable part 102 must be in a particular orientation in order to attach to each other (e.g., nut 124*a* only engages load gear 136*a* and nut 124*b* only engages load gear 136*b*). This can be accomplished using many techniques, e.g., having unique mating profiles for nut 124*a*/load gear 136*a* and nut 124*b*/load gear 136*b*.

In some embodiments, the device 100 can include multiple reservoirs. FIGS. 10A-10C show an example embodiment in which the disposable part 102 includes two reservoirs 106*a*, 106*b* that contain separate plunger assemblies 108*a*, 108*b*, each of which are driven by separate drive trains 114*a*, 114*b*. As shown in FIG. 10C, in some instances, both plunger assemblies 108*a*, 108*b* can be driven by a single drive component 112. With reference to FIG. 10C, the drive component 112 can cause rotation of a single drive gear 132 (e.g., via planetary gear 130), which can cause rotation of both load gears 136*a*, 136*b* (via idler gears 134*a*, 134*b*), which can cause translation of both plungers 120*a*, 120*b* to drive fluid out of both reservoirs 106*a*, 106*b* (or to generate a suction force to fill the reservoirs, as described below). In some embodiments, the gears, nuts, and/or lead screws can be modified such that plunger assemblies 108*a*, 108*b* translate in the same or opposite directions from each other. In other embodiments, the device 100 can be modified such that the drive component 112 controls the plunger apparatuses completely separately from each other. In other embodiments, the device 100 can be modified such that a separate drive component 112 controls each of the plunger assemblies 108*a*, 108*b*. In some embodiments with multiple reservoirs, all of the reservoirs (or a subset of two or more) can deliver fluid through a common outlet. In other instances, each reservoir can deliver fluid through its own dedicated outlet.

In some embodiments with multiple reservoirs, each of the reservoirs can include the same fluid or different fluids. In instances in which the reservoirs are filled with the same fluid, the multiple reservoirs can increase the dosage capacity of the device, or increase the amount of time the device can be used without replacing the disposable part 102. In some instances in which the reservoirs are filled with different fluids, each reservoir can contain a different medicament (e.g., medicaments that are prescribed together). For example, one reservoir can include levodopa and the other reservoir can include carbidopa. In some instances, one of the reservoirs can be empty (in such instances, the device can be configured or adapted such that a plunger assembly does or does not translate through the empty reservoir. In certain embodiments, the device 100 can be further operable to include more than two reservoirs (e.g., 3, 4, 6, 8, etc.). The same concepts described above regarding control of the plunger assemblies by either a single or multiple drive components can be applied to embodiments with more than two reservoirs.

Figure 10E:
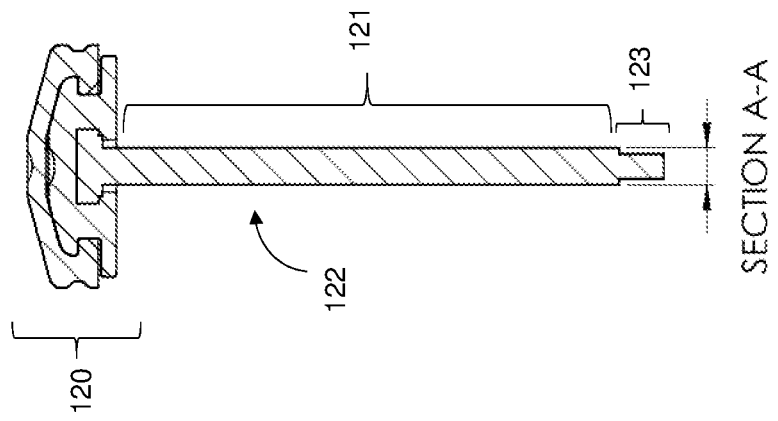
FIG. 10E is a schematic cross-sectional side view illustration of the plunger head and the lead screw of FIG. 10D, according to some embodiments.
Figure 10D:
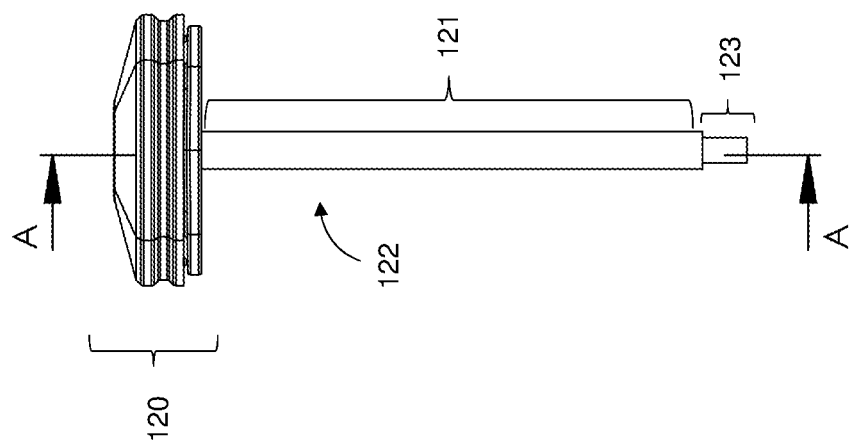
FIG. 10D is a schematic side view illustration of a plunger head and a lead screw attached to the plunger head of the delivery device, according to some embodiments.

Further referring to FIGS. 10D and 10E, the lead screw 122 may have a threaded portion 121 that extends along the lead screw 122 and a non-threaded portion 123, e.g., at a terminal end of the lead screw 122. The non-threaded portion 123 can extend from a distal end of the lead screw 122 in proximal direction thereof towards the plunger head 120. In other words, a tip portion at the distal end of the lead screw 122 may be non-threaded. The diameter of the non-threaded portion 123 can be smaller than, larger than, or the same as the outer diameter of the threaded portion 121. Optionally, the other tip portion at the proximal end of the lead screw 122, just below the plunger head 120, may also be non-threaded.

By configuring the lead screw 122 to have a non-threaded distal tip portion 123, limited mechanical positional tolerance can be afforded. For example, in cases where a plurality of lead screws are employed for concurrently forcing fluid medicament out of a respective plurality of reservoirs. For example, rotation of the corresponding nuts 124*a* and 124*b* by the drive gear 132 can cause the first and the second lead screws 122*a* and 122*b* (along with their corresponding plunger heads 120*a* and 120*b*) to concurrently translate in reservoirs 106*a* and 106*b*, as for example in embodiments of the double-piston arrangement schematically shown in FIG. 10C.

The first and second lead screws 122*a* and 122*b* may not, for example, translate in perfect temporal and/or spatial synchronization. As a result thereof, the first plunger head 120*a* for instance may arrive at the distal end of the reservoir 106*a* prior to the second plunger head 120*b*. Thus, the first plunger head 120*a* may abut against the distal end of the reservoir 106*a* and be brought to a stop thereby, while the first nut 124*a* is still forced to rotate and further while the nut 124*b* imparts a rotational force on the second plunger head 120*b* causing it to translate in distal direction. By having a non-threaded portion tip portion on either one of the two lead screws, the blocked lead screw 122*a* uncouples from the nut's 124*a* inner thread. As a result thereof, both nuts 124*a* and 124*b* can continue to rotate, only with nut 124*b* continuously imparting a translational force on the corresponding lead screw. In such embodiments, the drive gear 131 can continuously impart a rotational force onto nuts 124*a* and 124*b*, while avoiding damage to the mechanical components of the device's motor or plunger assemblies in case of abutment of the plunger heads 120*a* and 120*b* against the reservoirs' distal ends.

In some embodiments, the disposable part 102 is delivered to the patient with the medicament reservoir 106 not yet filled. To facilitate filling, in some cases the disposable part 102 is delivered to the patient with an attached vial adapter 150 (e.g., pre-packaged in sterilized packaging). Optionally, the vial adapter may be pre-assembled with the disposable part 102 in a packaging. Once unpackaged, the vial adapter is removable from the disposable part 102 to allow the fluid coupling thereof with a (e.g., standard) infusion or tubing of the patch pump for delivery of the fluid medicament that was delivered from the vials to the reservoir(s) of the disposable part 102.

Figure 11:
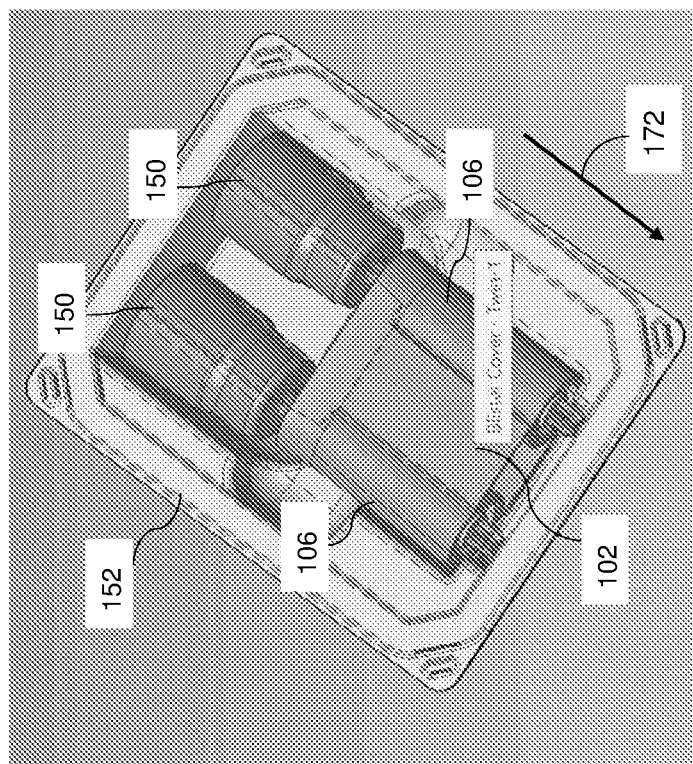
FIG. 11 is a schematic, 3D view of vial adapters attached to a disposable part within a blister, according to some embodiments.

An example blister 152 containing the disposable part 102 attached to vial adapters 150 is shown in FIG. 11 (depicting an embodiment including two vial adapters 150 for two medicament reservoirs 106a, 106b). In other embodiments, the device 100 can be provided to the patient with the disposable part 102 and vial adapter 150 detached from each other (e.g., in separate sterilized packages). As shown in FIG. 11, for a multiple reservoir embodiment, a separate vial adapter 150 can be used for each reservoir. In other instances, a single vial adapter 150 can be used to fill all of the reservoirs 106 (or in some cases a subset of two or more). In yet other embodiments, the disposable part 102 can be delivered pre-filled with medicament and a vial adapter 150 is not used.

In some embodiments, the device 100 is operable to use a filling station to fill the medicament reservoir 106 with medicament. An example filling station 154 is shown in FIG. 12A.

The filling station 154 can include a cradle 155 that receives the device 100 such that the filling station 154 and the device 100 are communicatively connected. Any type of connection can be used, e.g., a wired connection and/or a wireless connection (e.g., via a WiFi network, Bluetooth, etc.). In some instances, the cradle 155 holds the device 100 such that the reservoir 106 is held in a substantially vertical orientation (e.g., with reference to FIG. 4A, longitudinal axis 137 substantially along the y-axis) to reduce the flow of air into the reservoir 106 during the filling process.

Figure 12A:
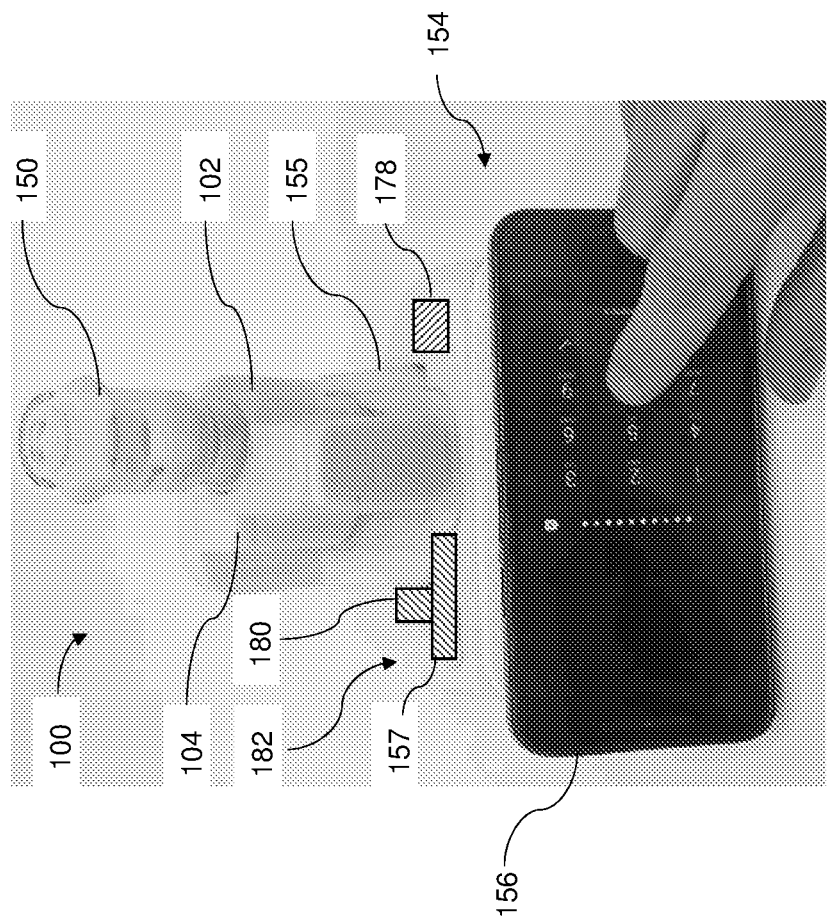
FIGS. 12A-12C are various views of the filling station and the filling station containing the delivery device, according to some embodiments.

As shown in FIG. 12A, in some embodiments, the filling station 154 can be controlled by a computing device (e.g., a smartphone) 156 in communication with the filling station 154 (wired or wirelessly). In such embodiments, the computing device 156 can provide a display having a graphical user interface ("GUI") for a user to interact with to input control instructions. The GUI can be provided when the computing device 156 executes a mobile application stored thereon and/or accessed from the cloud. The computing device 156 can transmit (wired or wirelessly) the instructions to a filling station controller 157 of the filling station 154, which can instruct control unit 116 within the device 100, to control the components of the device 100 in accordance with the user's instructions. In other instances, the filling station controller 157 can control the components of the device 100 directly (e.g., via a wired or wireless connection). In still other instances, the computing device 156 can control the components of the device 100 directly. In instances in which the computing device 156 controls the device 100 directly, the filling station 154 may not be used. In other embodiments, the computing device 156 may not be used and the filling station 154 may include its own user interface. In general, the filling station user interface can be any interface capable of receiving user instructions, e.g., a display presenting a GUI, buttons, etc. In operation, after a user removes the disposable part 102 and vial adapter 150 from the blister 152, these components can be attached to the reusable part 104 (which the user may already have from a prior dose administration) and the attached parts can be inserted into the filling station 154. A vial 158 can then be inserted into the vial adapter 150. The vial 158 can include the fluid to be delivered by the device 100, e.g., a medicament to be delivered to a patient. FIG. 13A shows a transparent side view of an example of this configuration.

Figure 13B:
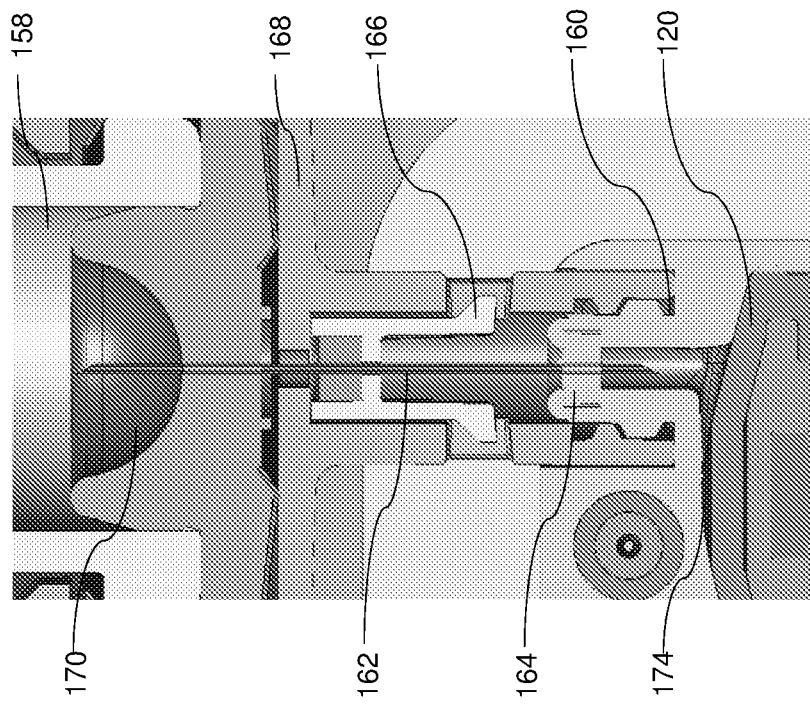
FIG. 13B is an enlarged close-up view of the vial adapter shown in FIG. 13A, according to some embodiments.
Figure 13A:
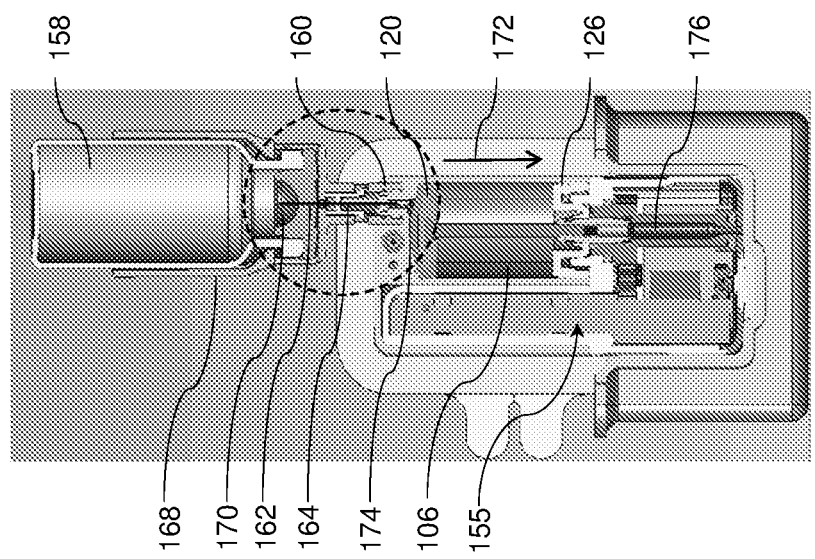
FIG. 13A is a schematic, transparent 3D view of the medicament delivery device within the filling station, according to some embodiments.

FIG. 13B is an enlarged view of the example vial adapter 150 shown in FIG. 13A. As shown, the vial adapter 150 can attach to the disposable part 102 via a first port 160. The first port 160 can be attached using known connection techniques, e.g., a threaded connection (as shown), interference fit, notch and groove connection, etc. The vial adapter 150 can include a hollow fill needle 162 that pierces a fill septum 164 on the disposable part 102 to fluidically access the reservoir 106. In order to avoid the potential for lateral/shear forces imparted by the vial adapter 150 to cause the septum to crawl (e.g., during shipment and/or shelf life), in some instances, the fill needle 162 is not rigidly connected to the vial adapter 150 and is instead held in place by a floating part 166 that enables relative movement between the fill needle 162 and the vial adapter 150. The relative movement can be in any direction, e.g., up and down (along the axis of the fill needle 162), side to side (perpendicular to the axis of the fill needle 162), etc. The end of the fill needle 162 opposite the end that pierces the fill septum 164 extends into a second port 168 of the vial adapter 150. A user can insert the vial 158 into the second port 168 such that the fill needle 162 fluidically accesses the contents of the vial 158 (e.g., by piercing a vial septum 170 (or other vial plug) located on the vial 158). The vial adapter 150 can shield the fill needle 162 to prevent inadvertent user contact.

The fill needle 162 can be adapted or configured such that the insertion force required to pierce the vial septum is relatively low, e.g., about 4N or less, about 5N, about 6N, about 7N, about 8N, about 9N, about 10N, etc., compared to the higher insertion forces typically required to pierce a vial septum, which is often done with a plastic spike. The reduced insertion force can be advantageous for patients with reduced strength, e.g., those suffering from Parkinson's Disease or other CNS disorders. For example, the needle 162 can be formed from a rigid metal material to enable a lower insertion force. By piercing both the fill septum 164 and the vial septum 170, the hollow interior of the fill needle 162 creates a fluidic pathway between the vial 158 and the medicament reservoir 106. In other cases, the fill needle 162 can be formed from plastic, in which case the insertion force can be, for example, in a range from about 30N to about 40N.

In some embodiments, once the vial 158 and the reservoir 106 are fluidically connected, the contents of the vial 158 can be transferred to the reservoir 106 to fill the reservoir 106. In some embodiments, the fill process requires translation of the plunger head 120, e.g., because the plunger head 120 is blocking the reservoir and/or because a suction force needs to be generated to draw fluid from the vial 158 through the fill needle 162 into the reservoir 106. In such embodiments, the plunger head 120 can be translated in response to control signals sent from control unit 116 (or in some cases from the filling station controller 157 of the filling station 154 or from the computing device 156. For example, the control signals can cause the drive component 112 to drive the drive train 114 such that the nut 124 rotates and causes the lead screw 122 and attached plunger head 120 to translate away from the vial 158, e.g., in a direction towards the reusable part 104 (schematically illustrated by arrow 172) generating a suction force (e.g., a vacuum) within the reservoir 106 that draws fluid from the vial 158 into the reservoir 106. The plunger head 120 can be translated in the direction of arrow 172 until it abuts bushing 126 and/or until a predetermined amount of fluid is contained within the medicament reservoir 106.

Figure 14:
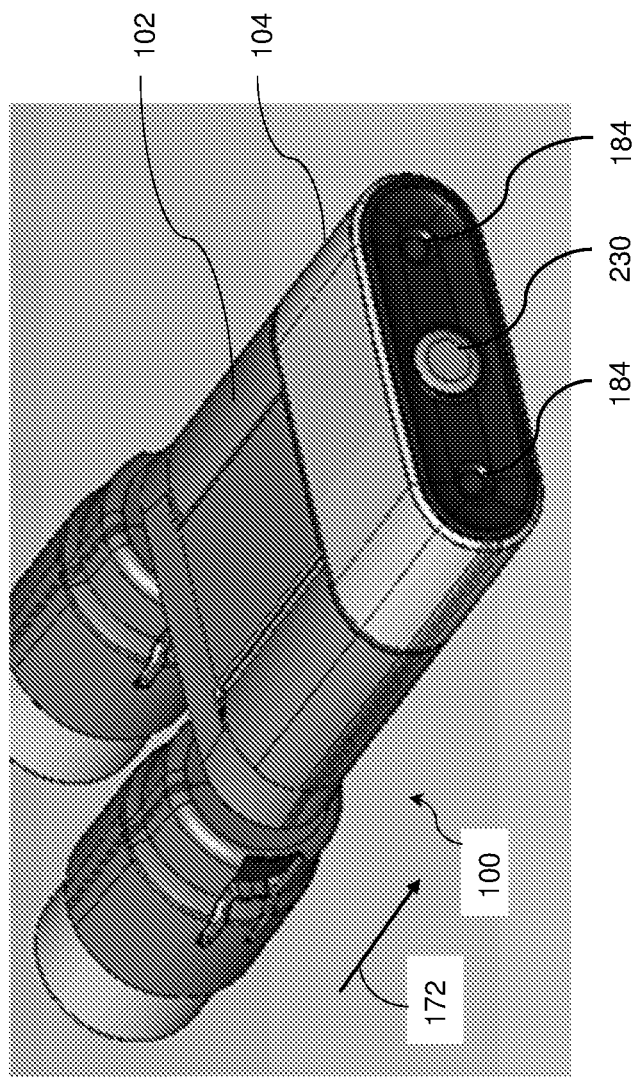
FIG. 14 is a schematic, 3D view of the delivery device including an access aperture and a control button, according to some embodiments.

In some instances, the reusable part 104 forms a void or cavity 176 for receiving a lead screw 122, when the plunger translates in the direction of arrow 172, for example, from a proximal to a distal end of the reusable part 104. Including the void 176 within the reusable part 104 of the device 100 ensures that the lead screw 122 remains enclosed and protected at all times, which can reduce obstructions that may otherwise block or interfere with the travel of the lead screw 122. In addition, enclosing the lead screw 122 can increase safety and wearability for the patient by shielding the patient from moving component(s). In some embodiments, the device 100 can include an access aperture 184 (see FIG. 14) such that the lead screw 122 can be accessed, e.g., for lubrication, repair, and/or to remove an obstruction or interference.

In some embodiments, the reusable part 104 comprises one or more openings at a distal end thereof. Example purposes of such opening(s) can include preventing the accumulation of dirt or other debris within the void 176, removing debris from the void via the opening(s), and/or gaining access to the void via the opening(s). An opening is for example shown in FIG. 4A (opening 177) and in FIG. 12B (openings 177A and 177B).

In general, the reservoir 106 can be filled at any appropriate filling rate. For example, the fill rate can be in a range from about 0.1 ml/min to about 5 ml/min. As further examples, the fill rate can be in a range from about 0.5 ml/min to about 2 ml/min, 0.7 ml/min to about 1.5 ml/min, and/or 1 ml/min to about 1.2 ml/min.

The vial adapter 150 can be either vented or not vented. The vial adapter 150 may not be vented in order to prevent fluid from exiting the vent ports when the vial adapter 150 is disconnected from the device 100. In embodiments with a non-vented vial adapter, the pressure within the vial 158 may be reduced as fluid is drawn out of the vial 158 during the filling process. In some cases, the pressure within the vial 158 at the end of the filling process is between about 0.3 bar and about 0.5 bar.

In some cases, the control signals can cause more complex motions of the plunger head 120. For example, in some instances, upon receipt of a fill instruction, the control unit 116 can cause the drive component to translate the plunger head 120 until it contacts the delivery end 174 of the medicament reservoir 106 (e.g., in instances in which the plunger head 120 does not contact the delivery end 174 when the disposable part 102 is provided to the patient). This action can serve multiple functions. For example, it can remove air from the reservoir 106 to ensure that a vacuum is created upon retraction of the plunger head 120. As another example, it can provide the control unit 116 with a known location of the plunger head 120 before filling (retraction) begins to ensure a repeatable amount of fluid is drawn into the reservoir. This may be advantageous in instances in which the position of the plunger head 120 within the reservoir 106 may vary when the disposable part 102 is provided to the patient.

In some instances, the control unit 116 can receive information from a sensor that informs it of the starting location of the plunger head 120, to determine how far the plunger head 120 needs to be translated to contact the delivery end 174 of the reservoir 106. In other instances, the control unit 116 can cause the plunger head 120 to be translated until a sensor informs it that the plunger head 120 is at the delivery end 174 of the reservoir 106. The device sensors are described in more detail below. In still further instances, the control unit 116 can operate open loop and cause the plunger head 120 to be translated a pre-determined amount that is known to bring the plunger head 120 into contact with the delivery end 174. Once the plunger head 120 is located at the delivery end 174, it can be retracted in the direction of arrow 172 to cause filling of the reservoir 106, as described above. Many other techniques and control algorithms for filling the reservoir 106 are contemplated. In some embodiments, the control unit 116 can operate in a closed loop, e.g., based on a force-feedback signal provided by a sensor (not shown).

In some instances, the control unit 116 (or in some cases the filling station controller 157 on the filling station 154 or the computing device 156) can initiate a filling operation upon receipt of instructions from a user to initiate filling. For example, the user can select an "initiate filling" icon on a GUI, e.g., on the computing device 156 or the filling station 154. In other instances, the control unit 116 (or in some cases the filling station controller 157 on the filling station 154 or the computing device 156) can automatically initiate the filling operation upon receipt of the device 100 within the cradle 155, without receipt of a user input fill instruction. In still other instances, the filling operation can be initiated based on the time of day (e.g., determined by a signal received from a clock of the processing unit 182 of the filling station 154).

In some embodiments, the filling station 154 can perform other functions, in addition to or as an alternative from the filling function described above. For example, the filling station 154 can include a charging module 178 (see FIG. 12A) for charging the power supply 118 (see FIG. 3). The charging module 178 can use any known charging technologies, e.g., electrical contract leads, inductive coils for wireless charging, etc. The charging module 178 can charge the power supply 118 to have at least enough power for a fully delivery cycle (e.g., 12 hours, 18 hours, 24 hours, 36 hours, 48 hours, 72 hours, etc.)

Figure 15B:
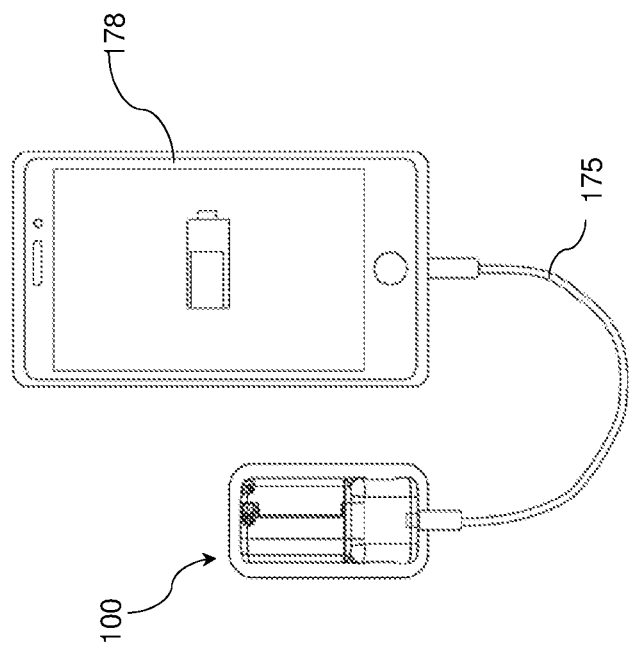
Figure 15A:
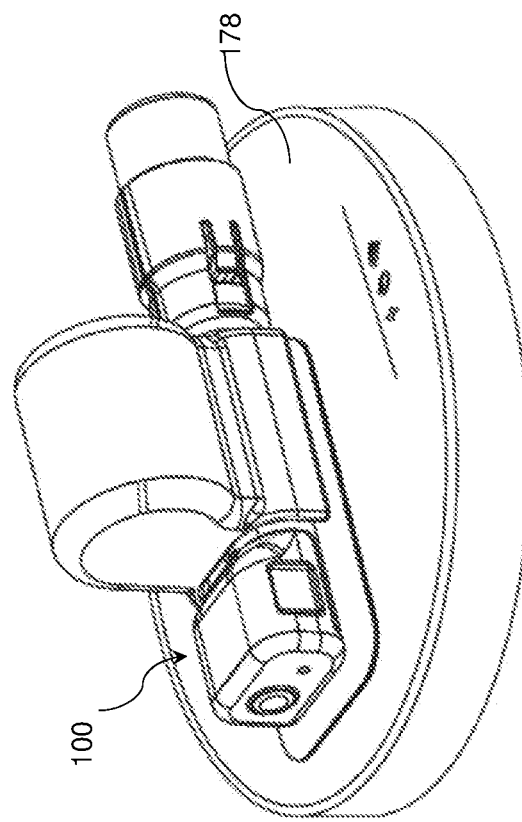
Figure 15C:
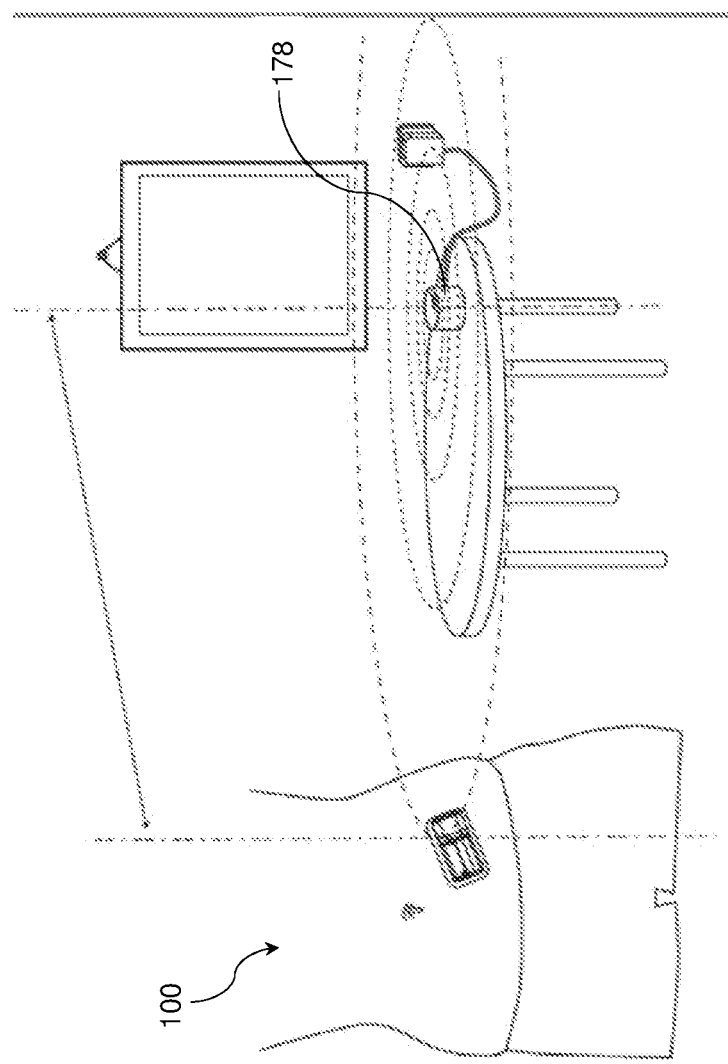
Figure 15F:
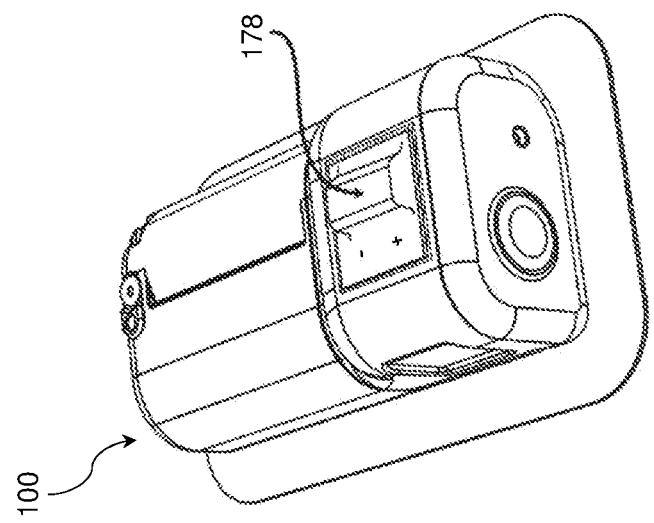
Figure 15E:
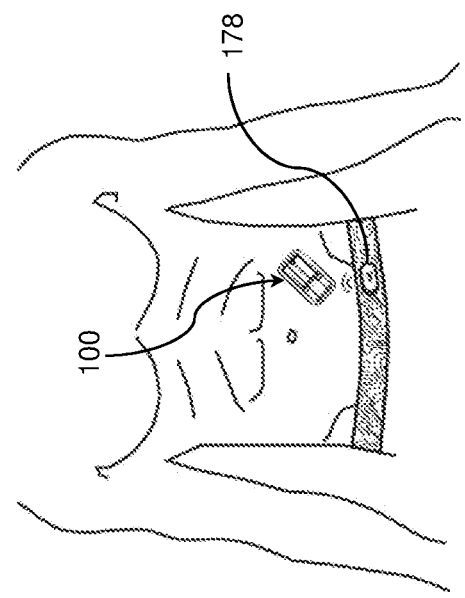
Figure 15G:
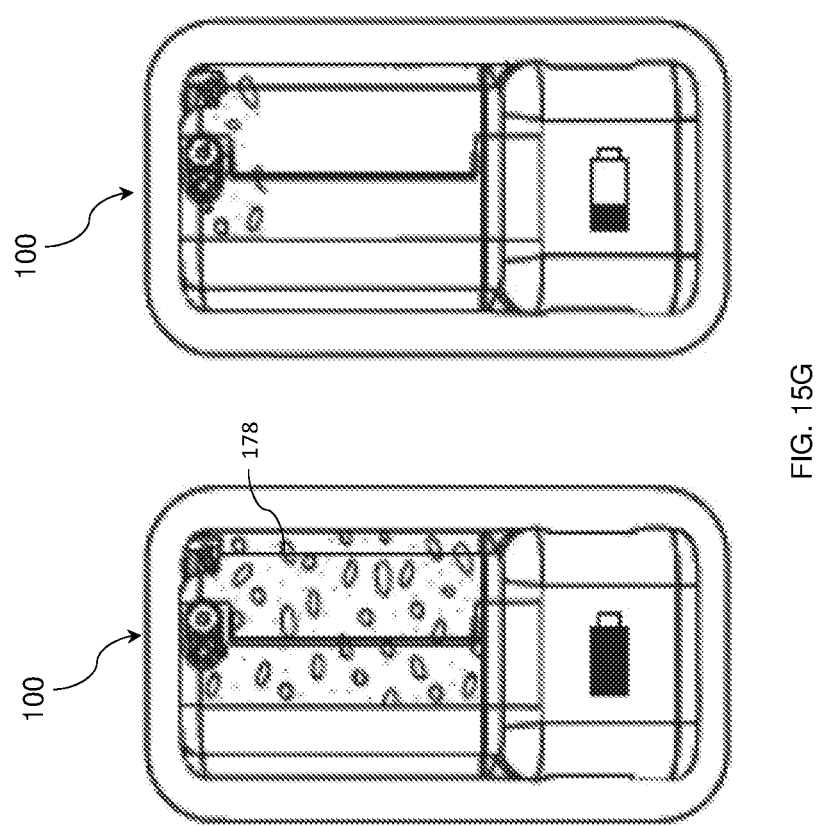

Some example charging configurations and techniques are described with reference to FIGS. 15A-15G. FIG. 15A shows an example wireless charging technique that uses inductive energy transfer from a charging module 178 to the device 100 (e.g., to power supply 118). The charging module 178 in FIG. 15A is a schematic depiction. As mentioned above, in some embodiments, it can be included in the filling station 154 (see FIG. 12A). FIG. 15B shows an example charging technique that uses a charging wire 175. The wire can connect to any power supply (e.g., a charging station, a wall outlet, a computing device, etc.). In some instances, the charging wire 175 can also have data communication capabilities. In some embodiments, as shown for example in FIG. 15C, the device 100 can be charged while it is attached to the patient's body. For example, as shown, the charging module 178 may emit a wireless charging field that charges the device 100 while the patient is wearing it. In some instances, the device 100 can be actively delivering medicament while being charged. In some embodiments, as shown for example in FIG. 15D, the charging module 178 can be a pad (or other structure) that can be placed on, under, and/or within any surface on which the user may be laying, sitting, and/or standing. For example, as shown, the charging module 178 can be placed on a mattress and/or charging pad and wirelessly charge the device 100 while the patient is sleeping. In some embodiments, as shown for example in FIG. 15E, the charging module can be worn by the user (e.g., clipped to the patient's clothing (e.g., belt), wristband, necklace, etc.). The wearable charging module 178 can charge the device 100 wirelessly (as shown) and/or with a wire. In some embodiments, the device 100 can be charged by an adhesive paper battery adhered to the device (see FIG. 15F). In some embodiments, the medicament contained by the device 100 can serve as the electrolyte of a battery that powers the device 100 (see FIG. 15G). In general, the device 100 can be powered by any suitable power supply 118. In some embodiments, the power supply 118 is a particular battery having voltage and/or current parameters that fits the performance requirements of the device 100 (e.g., 3.7V).

Figure 12B:
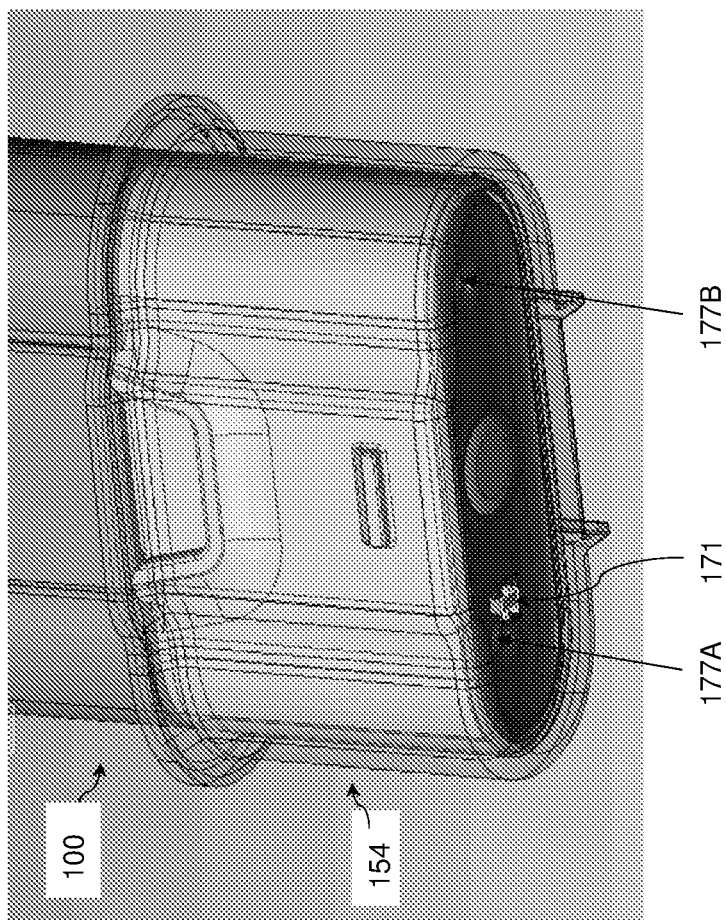
Figure 12C:
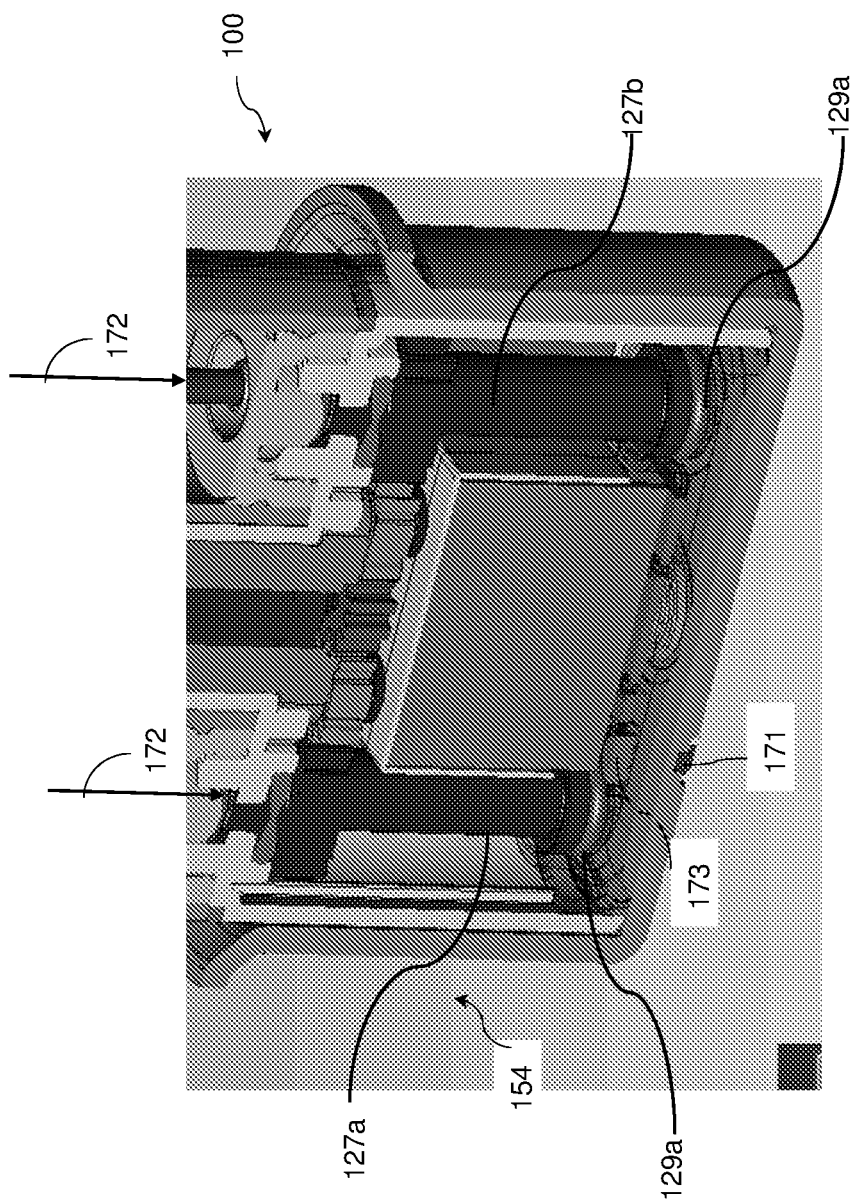

In some embodiments, the filling station 154 can include a feature to detect the presence of the device 100 in the cradle 155, which in some cases can cause the filling station 154 to initiate the filling process, the charging process (e.g., wireless charging), and/or another process. For example, the filling station can include a magnetic relay 171 (e.g., a reed switch) that can detect a magnet 173 within the device 100 (e.g., the reusable part 104). FIG. 12B is a bottom perspective view of the filling station 154 (in phantom) containing the device 100, showing an example magnetic relay 171. FIG. 12C is a cross-sectional view of the filling station 154 containing the device 100, showing an example configuration of the magnetic relay 171 and the magnet 173.

As another example, the filling station 154 can include a communication module 180. In some cases, the communication module 180 and the filling station controller 157 are part of a single processing unit 182. The communication module 180 can receive and transmit information between the device 100 and the filling station 154, the computing device 156, and/or the cloud. For example, the transmitted information can include information regarding the user's status and/or medical condition that can affect the configuration and operation of the device 100. As one example, a user may input their medical condition (e.g., stage two Parkinson's Disease) into the filling station 154 and/or the computing device 156, which can be transmitted to the device 100 via the communication module 180. In such instances, the electronics on the device 100 (e.g., via computing unit 117) can configure and operate the device appropriately for a patient having that condition. A medical condition is one of many examples of information that can be transmitted to the device 100 for configuration and operation of the device. A few other examples include particular dosing schedules, user sleeping schedule, user eating schedule, user weight/height, user age, status of user's medical condition, time of day, etc. In some cases, a user's dosing schedule is time based, e.g., the amount of medicament to be delivered is set on an hourly basis. In such cases, a clock of the processing unit 182 of the filling station 154 (or in some cases the computing device 156) can synchronize with a clock of the computing unit 117 of the device 100, to ensure that the proper dosage is delivered on the correct schedule.

The communication module 180 can also communicate information from the device 100 back to the filling station 154 and/or computing device 156. For example, as described in more detail below, the device 100 can track data collected by its sensors while the device 100 is worn by the patient. The collected data can include medical data, e.g., amount of medicament delivered, amount of time medicament was delivered, delivery schedule, etc. The collected data can also include user data, e.g., number of steps taken, hours asleep/awake, etc. The collected data can also include operational data for the device 100, e.g., if any malfunctions occurred, amount of charge in the power supply 118, if the reusable part 104 is scheduled for maintenance or replacement, etc. The information communicated from the device 100 to the filling station 154, the computing device 156, and/or the cloud via the communication module 180, can be presented to the user on the display of the filling station 154 and/or computing device 156.

In some embodiments, the communication module 180 is not used and/or not included and communication occurs directly between the device 100 and a computing device 156 and/or the cloud and vice versa. In such embodiments, information transmitted to and from the device 100 can occur with devices remote from the device 100 (e.g., computers, laptops, smartphones, tablets, smart watches, and/or any device that can communicate via wireless networks and/or access the cloud). In such instances, the information transmitted from the device 100 can be accessed remotely by the user, a caregiver, medical personnel, or other individuals. In some cases, the user (or other parties) can also transmit information to the device 100 from remote locations.

In some embodiments, once the filling process is complete, the vial 158 and vial adapter 150 can be removed from the device 100. More particularly, the first port 160 of the vial adapter 150 can be removed (e.g., unthreaded) from the device. The device 100 can then be removed from the filling station 154, in some instances following any data exchange or charging processes taking place. In some instances, the user can be alerted if the power supply 118 has not received a sufficient charge to complete a full dosing regimen. In some such cases, a user may not be able to activate the delivery mode (e.g., by pressing button 230, described below) unless the power supply 118 has a sufficient charge (e.g., to complete a full dosing regimen). The device 100 can then be coupled with the patient.

As shown in FIG. 16, in embodiments in which the device 100 is a standalone pump unit, tubing 186 can be attached to the outlet(s) 188 of the reservoir(s) 106 of the device 100. In some cases, the tubing 186 can be attached to the outlet(s) 188 with a Luer connector 190. The other end of the tubing can include an infusion set 192 that can include an infusion set needle 194 that accesses the subcutaneous tissue. The infusion set 192 (or in some cases multiple infusion sets) can be adhered to desired infusion site(s) on the body of the patient, e.g., abdomen, thigh, arm, etc. The device 100 can be carried by the patient, e.g., clipped to an article of clothing worn by the patient (e.g., a belt), adhered to the patient's skin, carried in the patient's pocket or in a fanny pack, etc.

Figure 17C:
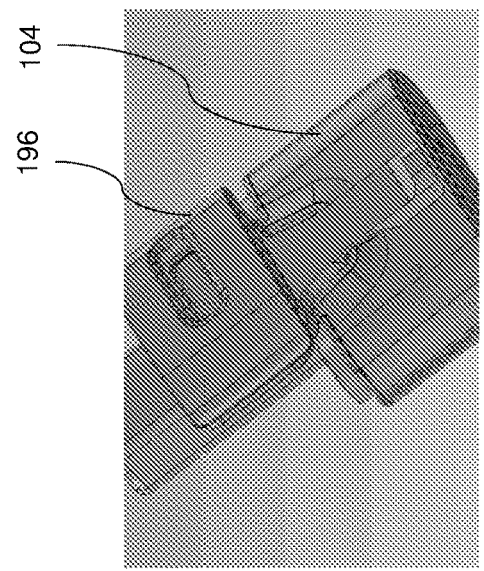
FIGS. 17A-17G are schematic, 3D views of a pump holder, according to some embodiments.
Figure 17B:
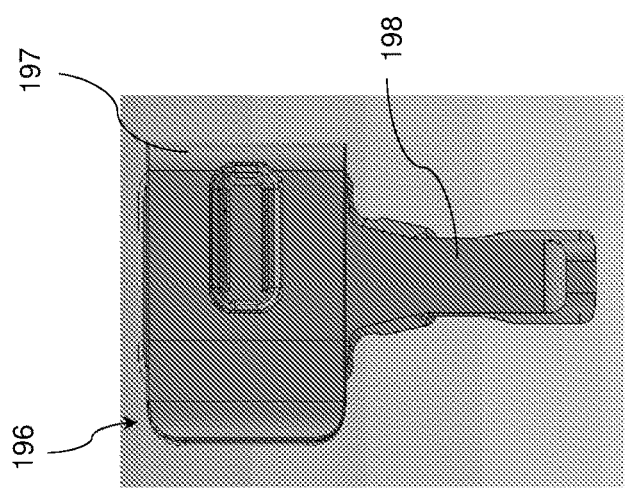
Figure 17A:
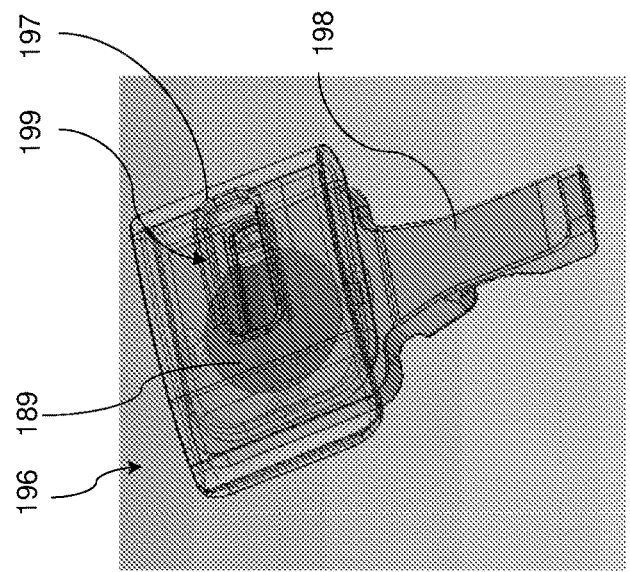
Figure 17E:
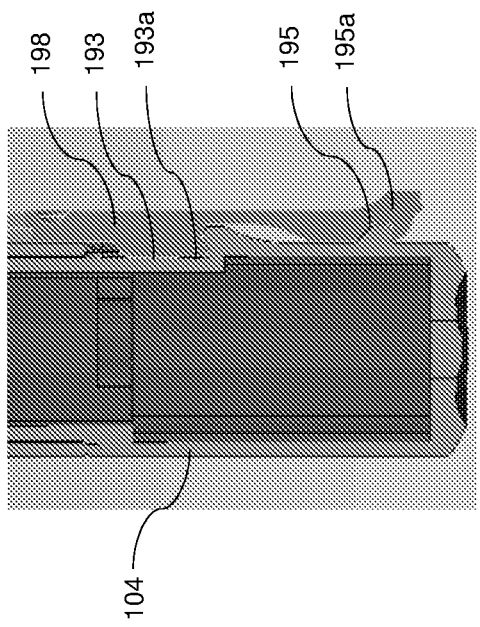
Figure 17G:
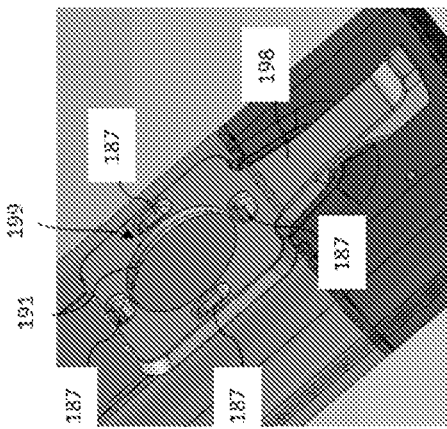
Figure 17D:
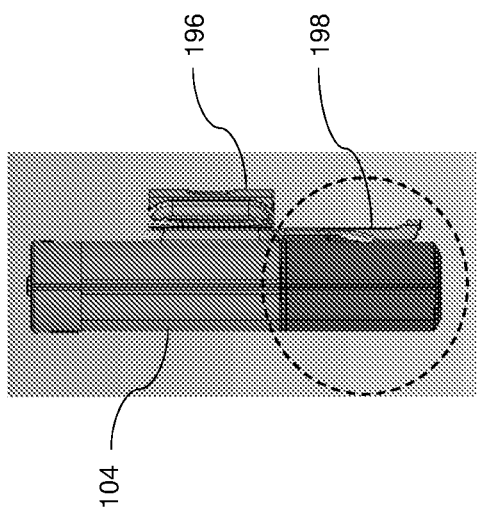

In some embodiments, the device 100 can be held by a pump holder 196 that allows the pump to be held in multiple different orientations. An example pump holder 196 can be seen in FIGS. 17A-17B. As shown, the pump holder 196 can include a clip portion 197 for attaching to a user or an article of clothing worn by the user (e.g., a belt) and a latch portion 198 for attaching to the device 100. FIG. 17C shows the pump holder 196 with the latch portion 198 attached to the reusable part 104 of the device 100 (though in other embodiments the latch portion 198 can attach to the disposable part 102). FIGS. 17D-17E illustrate an example attachment scheme between the latch portion 198 and the reusable part 104, which can generally employ any quick connect/disconnect scheme that allow the device 100 to be quickly and easily connected and disconnected from the holder 196. FIG. 17D is a side view of the holder 196 attached to the reusable part 104 and FIG. 17E is a close-up cross sectional view of the circled portion in FIG. 17D. As shown, the reusable part 104 can include a groove 193 and a notch 195 that are operable to engage corresponding clips 193a, 195a on the latch portion 198. In some embodiments, either the groove 193 and/or notch 195 can be omitted. Many other attachment schemes are possible (e.g., alternative groove/notch configurations, magnets, etc.). In some instances, the device 100 can be connected or disconnected with a single hand.

Figure 17F:
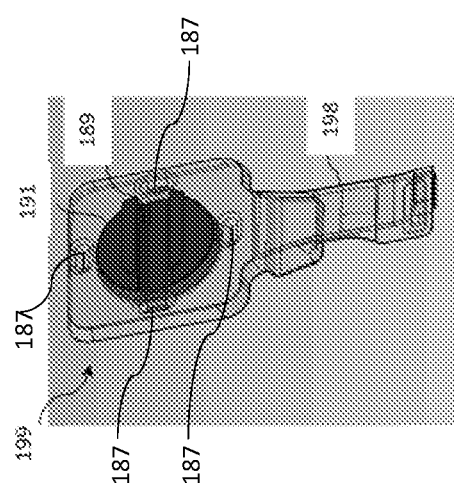

In some situations, it can be advantageous to have the tubing 186 connected to the device 100 directed in a particular orientation that is advantageous for reaching a particular infusion site, e.g., to avoid tugging/discomfort or to keep the tubing out of the patient's way. The holder 196 can offer a solution by including a rotation mechanism 199 that rotates the device 100 (and, as a result, the tubing 186)

to a desired orientation. In general, the holder 196 can include any structure capable of rotating and holding the tubing in various orientations (e.g., angular positions). An example rotation mechanism 199 can be seen in FIGS. 17F-17G (with reference to FIG. 17A). As shown the rotation mechanism 199 can include a disc 189. In some instances, the disc 189 is rotationally fixed to the clip portion 197 and a bore 191 of the latch portion 198 can rotate about the disc 189 to position the device 100 at various angular positions. In other instances, the disc 189 is rotationally fixed to a latch portion of the disc 189 and can rotate with respect to the clip portion 197 to rotate the device 100 to various angular positions. In general, the device 100 can be positioned at any desirable angular position. In some instances, the rotation mechanism 199 can include structure to position the device 100 at certain predetermined locations. As one example, the rotation mechanism 199 can include detents 187 operable to hold the disc 189 at 4 predetermined positions (as shown in FIGS. 17F-17G).

In operation, fluid can be evacuated from the reservoir(s) 106 through the tubing 186, through the infusion set 192 and into the subcutaneous tissue. In some instances, each reservoir 106 can deliver fluid to separate infusions sets 192. In other instances, two or more reservoirs 106 can deliver fluid to the same infusion set 192.

In embodiments in which the device 100 is a patch pump, the device 100 can be adhered to a skin surface of the patient (e.g., abdomen, thigh, arm, etc.) In general, any adhesion technique that results in the device 100 being firmly secured to the skin surface can be used. For example, an exterior surface of the disposable part 102 can be adapted or configured to be adhered to the skin surface. In some instances, microdermal anchors can be used to attach the exterior surface to the skin surface. In other instances, a sub-pressure can be generated between the skin surface and the exterior surface (e.g., using a suction cup). In other instances, the adhesive portion 110 can be used (see FIG. 2). The adhesive portion 110 can include a layer of adhesive having a device surface side that adheres to the device 100 and a skin surface side that adheres to the skin surface. The adhesive portion 110 and/or the adhesive layer can have elastic properties that enable the adhesive portion 110 and/or layer to be stretched to conform to a particular surface. The skin surface side 110*a* and the device surface side 110*b* can each include either a continuous or a discontinuous adhesive. In some cases, one side contains a continuous adhesive (e.g., the skin surface side 110*a*) and the other side contains a discontinuous adhesive (e.g, the device surface side 110*b*).

Figure 18A:
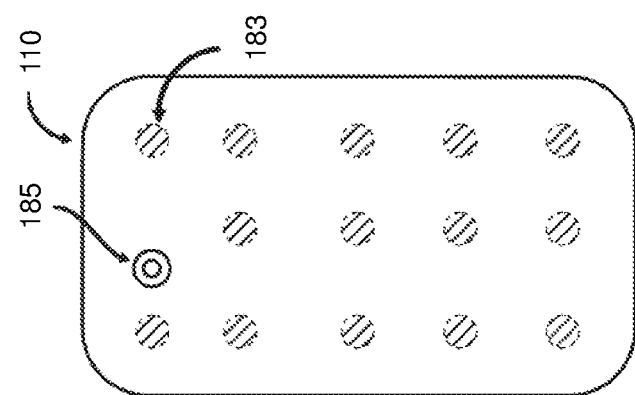
FIGS. 18A-18D illustrate adhesive patterns for an adhesive portion, according to some embodiments.
Figure 18B:
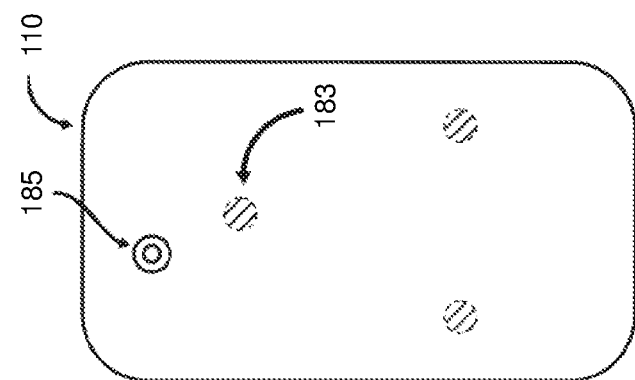
Figure 18D:
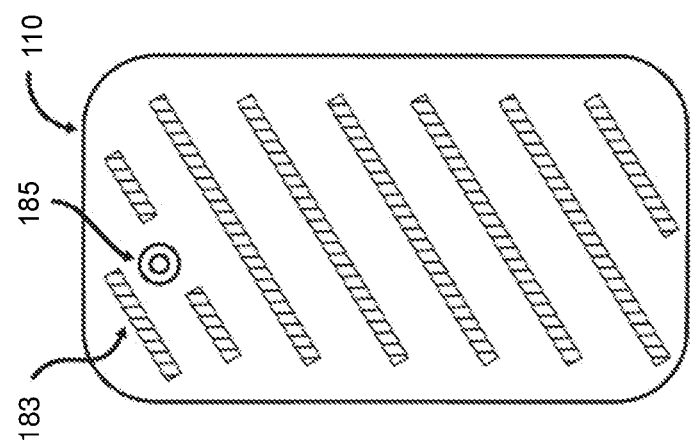
Figure 18C:
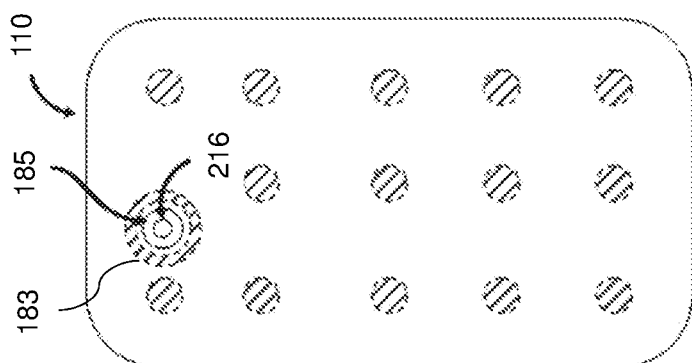

In general, adhesive can be applied to the adhesive portion 110 in any pattern that will reliably adhere the device 100. A few examples are shown in FIGS. 18A-18D. FIG. 18A shows a pattern of three adhesive 183 spots, which in some instances is the minimum number of spots that will fix the device in a given plane and prevent undesirable rotations. FIG. 18B shows a pattern with more adhesive 183 spots in a linear array pattern. FIG. 18C shows a pattern having a concentric ring of adhesive 183 located around an aperture 185 in the adhesive portion 110 through which a cannula is inserted (described below). In some cases the concentric ring of adhesive 183 is discontinuous and/or spaced radially away from the aperture 185. FIG. 18D shows a pattern having, relative to the device's longitudinal axis, diagonally oriented adhesive 183 strips (in other embodiments, the strips can be linear, curved, etc.). Many other examples of adhesive patterns are possible.

Figure 19:
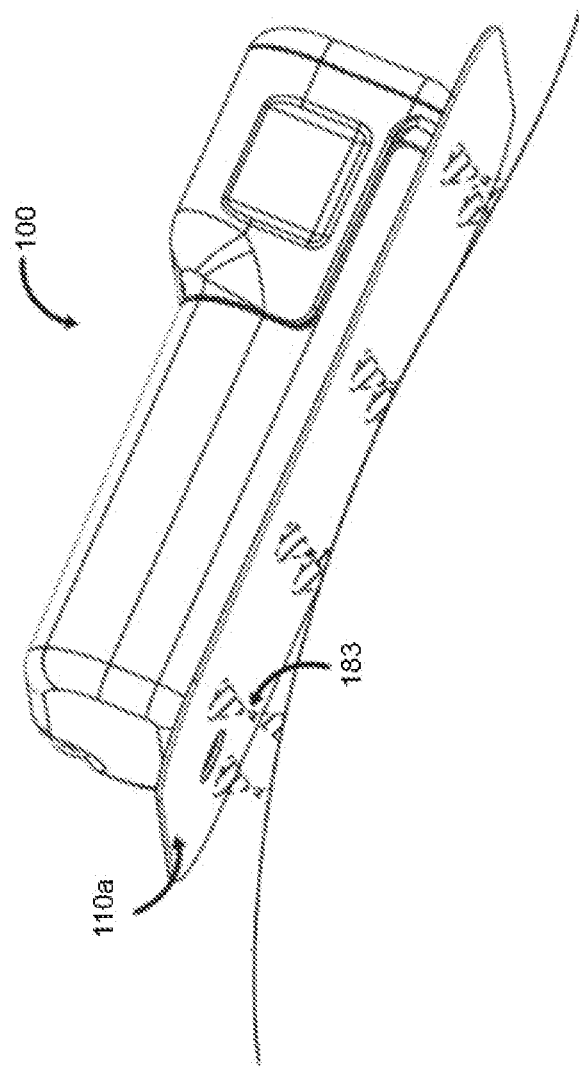
FIG. 19 is a schematic illustration of adhesive on a skin surface side of the adhesive portion, according to some embodiments.
Figure 20:
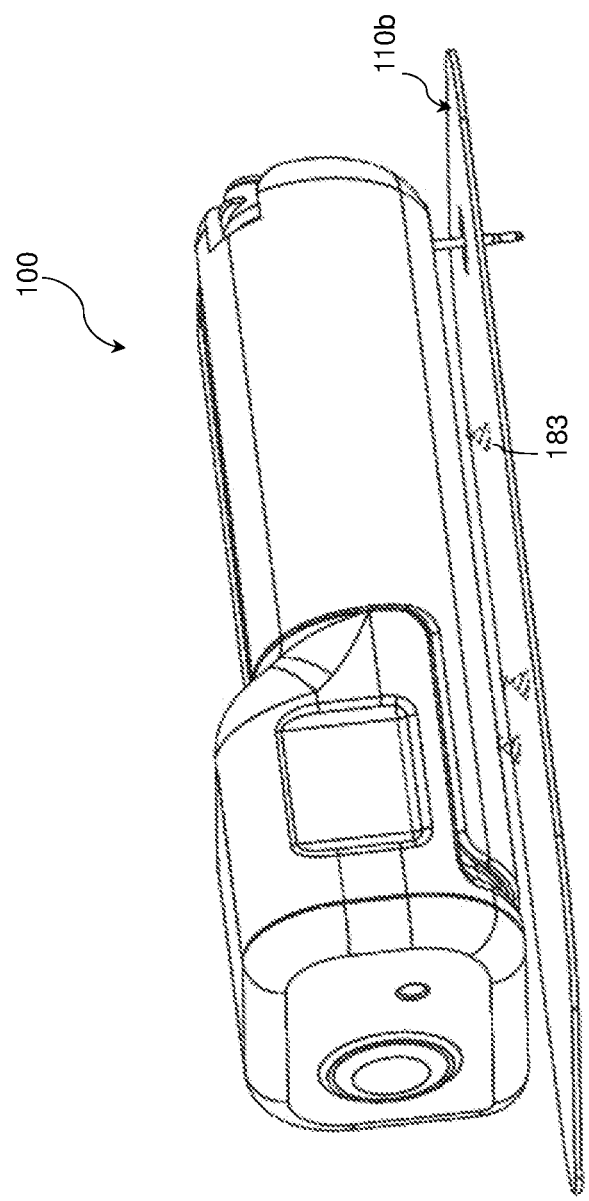
FIG. 20 is a schematic illustration of adhesive on a device surface side of the adhesive portion, according to some embodiments.

The adhesive patterns described above can be applied on either the skin surface side 110*a* or the device surface side 110*b* of the adhesive portion 110. For example, FIG. 19 shows the linear array adhesive spot pattern of FIG. 18B on the skin surface side 110*a* of the adhesive portion 110. As another example, FIG. 20 shows the three adhesive spot pattern of FIG. 18A on the device surface side 110*b* of the adhesive portion 110.

In embodiments in which the device 100 is a patch pump, once the device 100 is adhered to the skin surface of the patient, a fluidic connection can be established between the reservoir(s) 106 of the device 100 and the subcutaneous tissue. In general any prior known technique for inserting a cannula into the subcutaneous tissue can be used to fluidically couple the above device 100 to subcutaneous tissue. In addition, a new inventive technique for establishing the fluidic connection is described herein.

Various embodiments of this description relate to a cannula insertion mechanism 200. In some instances, the cannula insertion mechanism 200 can be a standalone component attachable to the pump 100, when the pump 100 is adhered to the skin surface of the patient. In some instances, like the disposable part 102 and vial adapter 150, the cannula insertion mechanism 200 can be distributed to the patient in sterilized packaging. FIGS. 21A-21C illustrate an example configuration and operation of the mechanism 200, according to certain embodiments. The mechanism 200 may include, for example, a torsion spring 202 that rotates a cam 204. The cam 204 has an eccentric link 206 attached to a cannula plunger 208. The cannula plunger 208 includes an upper portion 210 fixedly attached to a needle 214 and a lower portion 212 that holds a cannula 216 (e.g., a flexible cannula), such that the cannula 216 is mounted on the needle 214. Before the cannula 216 is delivered, the torsion spring 202 is prevented from rotating by a pin 218. In operation, when a user presses a button 220, the pin 218 is displaced allowing the torsion spring 202 to rotate the cam 204. As shown in FIG. 21B, in the example embodiment, during a first stage of delivery, rotation of the torsion spring 202 initially causes the cannula plunger 208 to displace downwards, causing insertion of both the needle 214 and the cannula 216 into the subcutaneous tissue of the patient. At the bottom of stroke, the lower portion 212 of the cannula plunger 208 is held in place (e.g., via a notch and groove assembly, 222 and 224). As shown in FIG. 21C, in the example embodiment, during the second stage of delivery, as the torsion spring 202 continues to rotate the cam 204, the upper portion 210 of the cannula plunger 208 is displaced upward removing the needle 214 from the subcutaneous tissue, while leaving the cannula 216 in place. Once the cannula 216 is in place, the cannula insertion mechanism 200 (e.g., including the torsion spring 202, the cam 204, the eccentric link 206, the upper portion 210, and the needle 214) can be removed from the device 100, while leaving the lower portion 212 and cannula 216 in place to deliver fluid from the reservoir 106 to the subcutaneous tissue.

In some instances, the cannula 216 is hollow and fluid flows through a central hollow void out of the tip 215 of the cannula 216. In other instances, the cannula 216 forms at least one delivery aperture 217 in a side wall 219 of the cannula 216, as shown for example in FIGS. 22A and 22B. In some cases, the cannula 216 can form a plurality of delivery apertures 217 formed at different heights along the side wall 219 of the cannula 216. The delivery apertures 217 can be formed at the same or different circumferential positions about the cannula side wall 219. In some cases, the apertures 217 are formed equidistant from each other and/or the top or bottom of the cannula 216. In other cases, the apertures 217 are formed non-equidistant from each other and/or the top or bottom of the cannula 216. The cannula 216 can be made of any appropriate material, e.g., stainless steel, silicon, carbon fiber, PTFE, and/or combinations thereof. In some cases, a single cannula 216 can be split into multiple injection tubes. In some embodiments, a cannula comprises a plurality of apertures, and at least two of the plurality of apertures are formed at a different height or the same height along a side wall of the cannula.

In some embodiments, many modifications to the mechanism 200 shown in FIGS. 21A-21C are contemplated. For example, the torsion spring 202 can be released using structures other than the button 220 and pin 218 assembly. In general any structure that reliably holds, for example, the torsion spring in a compressed position until a user moves the structure and releases the torsion spring can be used. One example can include a pivoting latch. Many other structures are possible. As another example, the insertion force can be provided by structures other than a torsion spring, e.g., a linear spring, a user-applied force, etc. As another example, the lower portion 212 of the cannula plunger 208 can be held in place using structures other than the notch and groove assembly 222 and 224. In general, any structure that reliably holds the lower portion 212 in place once the needle 214 is delivered to the subcutaneous tissue can be used. For example, in some embodiments the holding structure can include an interference fit, flexible fingers, etc.

Figure 23A:
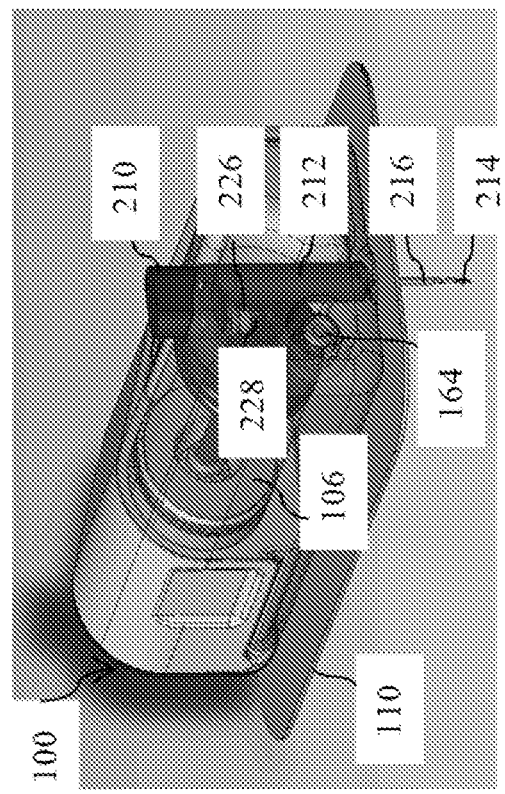
FIGS. 23A-23D are schematic illustrations of a technique for fluidically coupling the reservoir to a cannula, according to some embodiments.
Figure 23B:
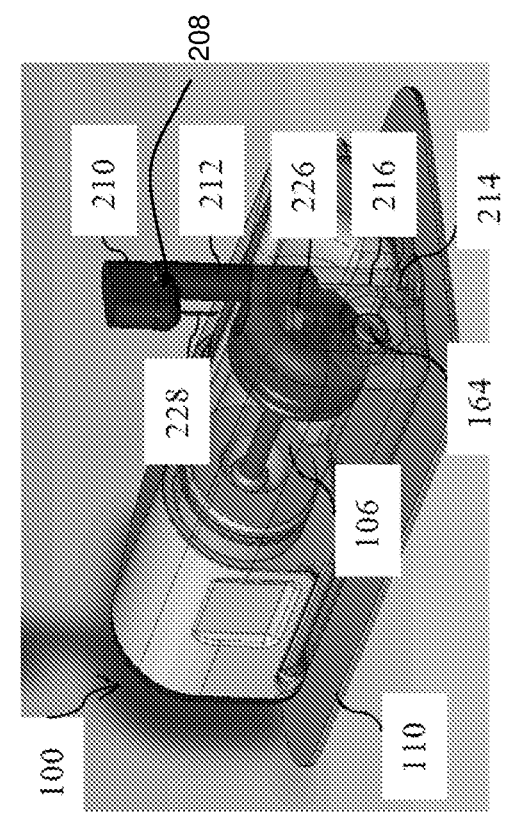
Figure 23D:
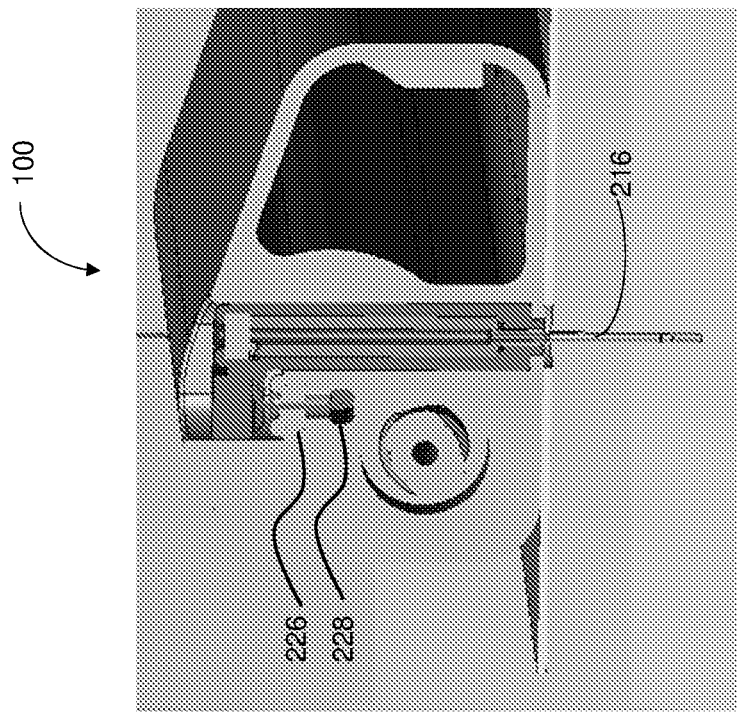
Figure 23C:
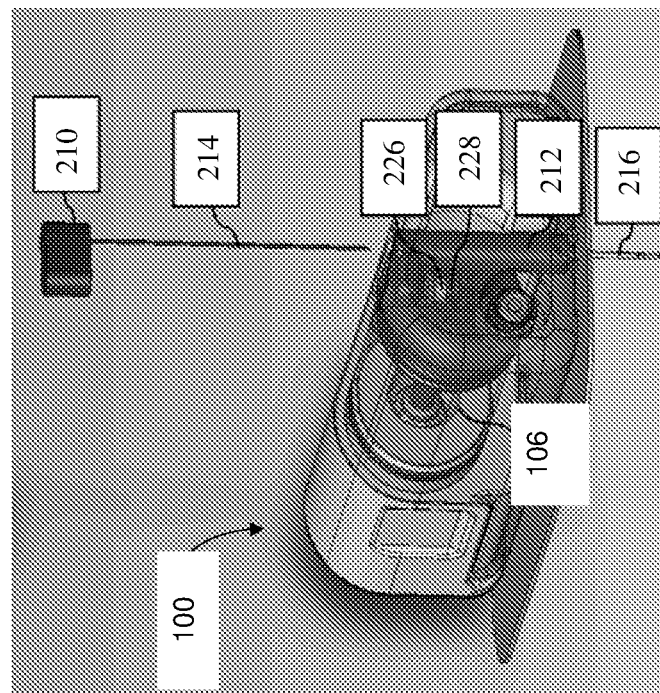
Figures 24A, 24B:
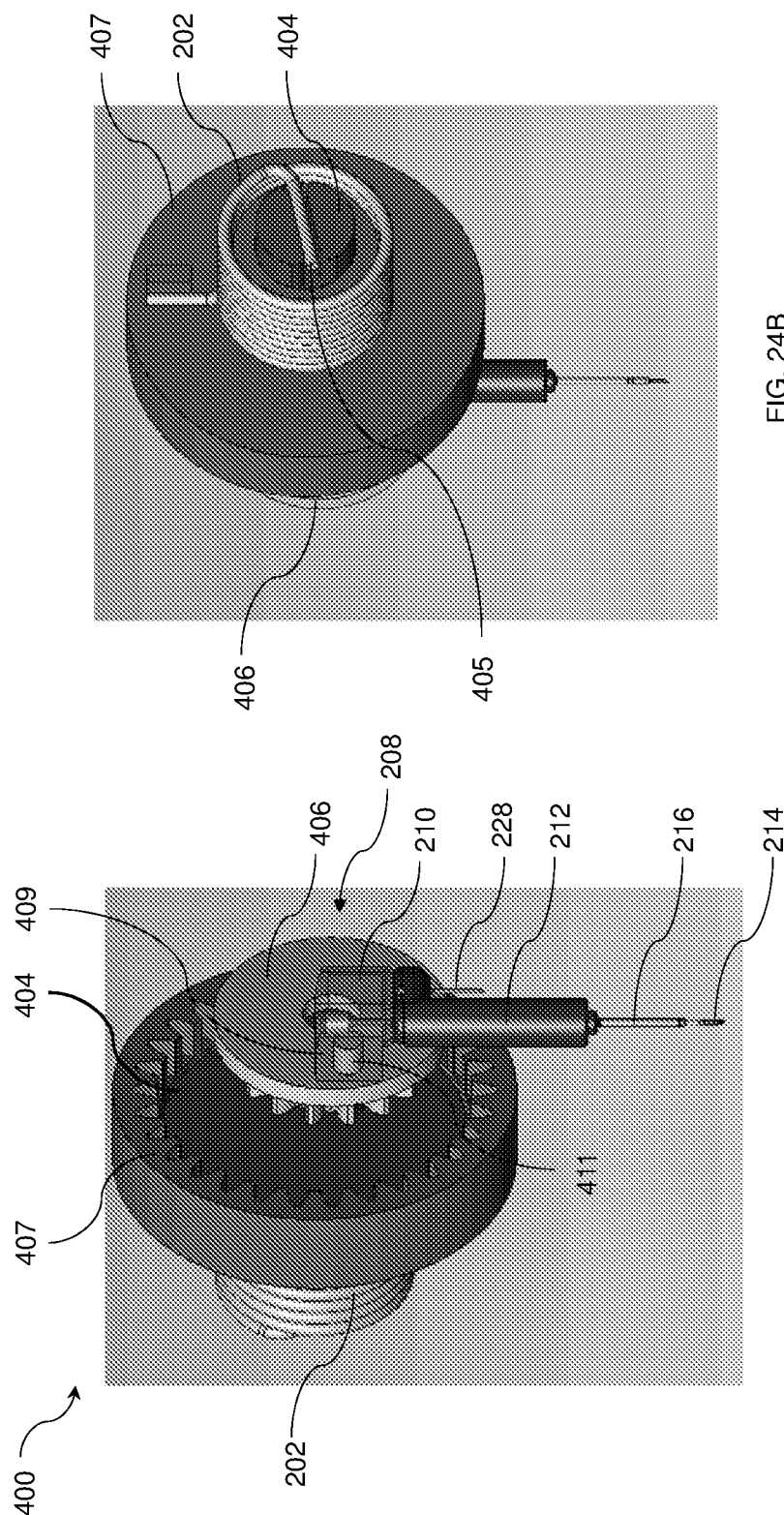

In some embodiments, the cannula insertion mechanism 200 also performs the function of fluidically coupling the reservoir 106 to the cannula 216, such that fluid evacuated from the reservoir 106 is delivered through the cannula 216 to the subcutaneous tissue of the patient. FIGS. 23A-23C illustrate the fluidic coupling functionality, according to example embodiments, with reference to the same delivery stages as the cannula placement shown in FIGS. 21A-21C. FIGS. 23A-23C do not show the torsion spring 202 and cam 204 portion of the cannula insertion mechanism 200, so as to not block certain structures that illustrate the fluidic coupling function. In operation, however, the torsion spring 202 and cam 204 portion of the cannula insertion mechanism 200 can be attached to the cannula plunger 208 shown in FIGS. 23A-23C, to translate the upper portion 210 and the lower portion 212 into the various depicted positions. The same reference numerals refer to generally the same structures in FIGS. 21A-21C and FIGS. 23A-23C, although the structures have slightly different geometries between the two sets of figures, according to some embodiments.

As described above, in some embodiments, before the cannula 216 is inserted into the subcutaneous tissue, the reservoir 106 and cannula 216 are not fluidically coupled. The fluid reservoir 106 can be sealed by a delivery septum 226. The delivery septum 226 can be different than the fill septum 164 (see FIGS. 23A-23C) or the same as the fill septum 164. In addition to holding the cannula 216, the lower portion 212 of the cannula plunger 208 can also include a rigid fluidic link 228 (e.g., a needle) in fluidic communication with the cannula 216. In such embodiments, during the first delivery stage (see FIG. 23B), when the cannula 216 is placed in the subcutaneous tissue, the link 228 can pierce the delivery septum 226, fluidically coupling the reservoir 106 with the cannula 216 (i.e., fluid evacuated from the fluid reservoir 106 travels through the link 228 into the cannula 216, from where it is delivered to the subcutaneous tissue of the patient). As described above, in some instances, during the second delivery stage (see FIG. 23C), the upper portion 210 of the cannula plunger 208 is withdrawn with the needle 214, while the lower portion 212, the cannula 216, and the link 228 remain in place. FIG. 23D is an enlarged view of the lower portion 212, the cannula 216, and the link 228 in place after the cannula insertion mechanism 200 (including the torsion spring 202, the cam 204, the eccentric link 206, the upper portion 210, and the needle 214) are removed from the device 100.

FIGS. 24A-24E illustrate a different cannula insertion mechanism 400 that, in some embodiments, can be used to insert the cannula 216 into the subcutaneous tissue and/or fluidically couple the reservoir 106 to the cannula 216. Similar to the cannula insertion mechanism 200 shown in FIGS. 21A-21C, the cannula insertion mechanism 400 can be used to deliver a cannula plunger 208 having an upper portion 210 and a lower portion 212. Parts that are interchangeable (or nearly interchangeable with minor structural changes) between the two cannula insertion mechanisms 200, 400 are referred to with the same reference numerals in FIGS. 21A-21C and FIGS. 24A-25E, although these structures may be depicted with slight geometric differences in the different figures.

In some embodiments, the cannula insertion mechanism 400 also uses the rotational force of a torsion spring 202. However, instead of being attached to an eccentric link 206, the torsion spring 202 can be attached to a hub 404. The torsion spring 202 can attach to the hub 404 using any known technique, e.g., a portion of the torsion spring 202 can fit into a slot 405 in the hub 404 (see FIG. 24B). The hub 404 can attach to an inner gear 406 such that rotation of the hub 404 rotates the inner gear 406 within an outer gear 407. In general, the hub 404 and inner gear 406 can be attached using any technique, e.g., a slot and pin connection, a notch and groove connection, a shaft connection, etc. The inner gear 406 can also be attached to the upper portion 210 of the cannula plunger 208. In general, the inner gear 406 and upper portion 210 can be attached using any known technique, e.g., the inner gear 406 can include a pin 409 that fits into a corresponding slot 411 in the upper portion 210.

FIGS. 24C-24E illustrate an example operation of the cannula insertion mechanism 400, according to certain embodiments. FIG. 24C shows the mechanism 400 before the cannula is inserted into the tissue. The torsion spring 202 can be restrained (e.g., prevented from being released) using any technique. For example, the hub 404 can be held with a pin that can be released by pressing a button, similar to the configuration shown in FIGS. 21A-21B with pin 218 and button 220. In this approach, the torsion spring 202 can be the only component in tension, which can allow the remainder of the insertion mechanism 400 to be non-stressed. As another example, the inner gear 406 can be held with a pin that can be released by pressing a button, similar to the configuration shown in FIGS. 21A-21B with pin 218 and button 220. As another example, the upper portion 210 of the cannula plunger 208 can be held with a pin that can be released by pressing a button, similar to the configuration shown in FIGS. 21A-21B with pin 218 and button 220. In this approach, freedom of motion between the components of the insertion mechanism 400 can be minimized.

When the torsion spring 202 is released, rotation of the torsion spring 202 rotates the hub 404, which causes the inner gear 406 to rotate counter clockwise, forcing the upper portion 210, lower portion 212, cannula 216, and needle 214 towards the patient's skin/tissue. The mechanism 400 can be adapted or configured such that when the inner gear 406 reaches the position within the outer gear 407 that is closest to the patient's skin, the cannula 216 and the needle 214 are delivered to a desired depth within the patient (see FIG. 24D). After the cannula 216 and the needle 214 are delivered to the desired depth, the inner gear 406 can continue rotating within outer gear 407. As in the embodiment described above, the upper portion 210 can be fixedly connected to the needle 214 and detachably connected to the lower portion 212, such that as the inner gear 406 continues to rotate, the upper portion 210 is separated from the lower portion 212 and the needle 214 is withdrawn from the patient and the cannula 216, while the lower portion 212 and the cannula 216 remain in their delivered position (see FIG. 24E). In some instances, the cannula insertion mechanism 400 can be adapted or configured such that the insertion force (e.g., the force applied to the cannula 216/needle 214 for insertion into the tissue) remains constant during various portions of the delivery process (e.g., during insertion of the cannula 216 and the needle 214 into the tissue and/or during retraction of the needle 214).

The cannula insertion mechanism 400 can also fluidically couple the reservoir 106 with the cannula 216, e.g., by piercing a septum with a rigid fluidic link 228, in a similar manner to that described with respect to the cannula insertion mechanism 200 above. Once the cannula 216 is delivered, the insertion mechanism 400, the torsion spring 202, the hub 404, the inner gear 406, the outer gear 407, the upper portion 210, and the needle 414 can be removed from the device.

Many adaptations to the cannula insertion mechanism 400 shown in FIGS. 24C-24E are possible. As one example, although FIGS. 24C-24E show the inner gear 406 as rotating counter clockwise within outer gear 407, in other embodiments the inner gear 406 can rotate clockwise within outer gear 407. As another example, in some embodiments, the hub 404 can be attached to the outer gear 407, which can be attached to the cannula plunger 208 and rotate (e.g., with respect to a fixed inner gear) to deliver the cannula 216 into the tissue. As another example, in some embodiments, the inner gear 406 and the outer gear 407 can be replaced with structures that engage without threads, e.g., a cam and follower connection, a slot and groove connection, etc.

In some embodiments, many other techniques can be used to fluidically couple the reservoir 106 and the cannula 216. As one example, the torsion spring 202 can be replaced with a linear spring that expands and retracts in a linear fashion to deliver and retract the insertion needle 214. As another example, the lower portion 212 can include an aperture (as opposed to the rigid fluidic link 228) that fluidically couples the reservoir 106 and the cannula 216 upon placement of the lower portion 212. In other instances, a flexible tubing can couple the reservoir 106 to the cannula 216. In some cases, the tubing is attached to the lower portion 212 and/or cannula 216 after placement of the lower portion 212.

Figure 25A:
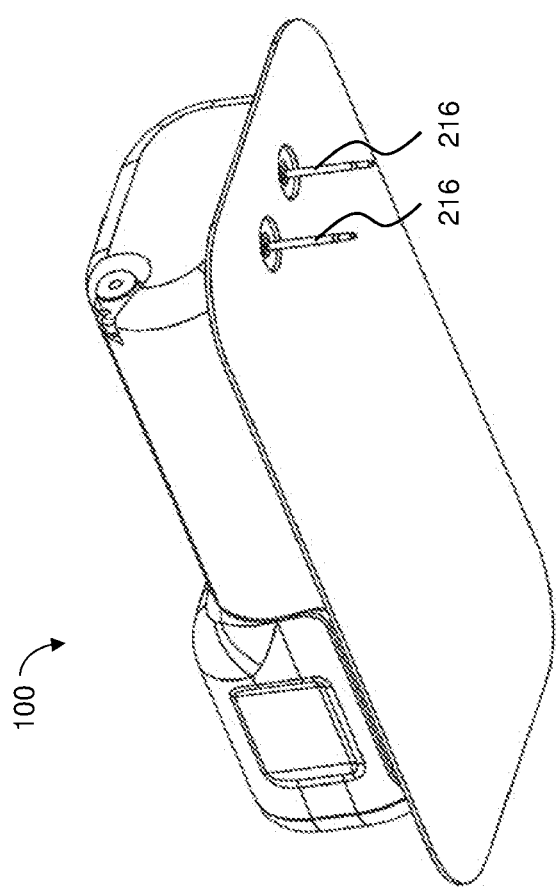
Figure 25B:
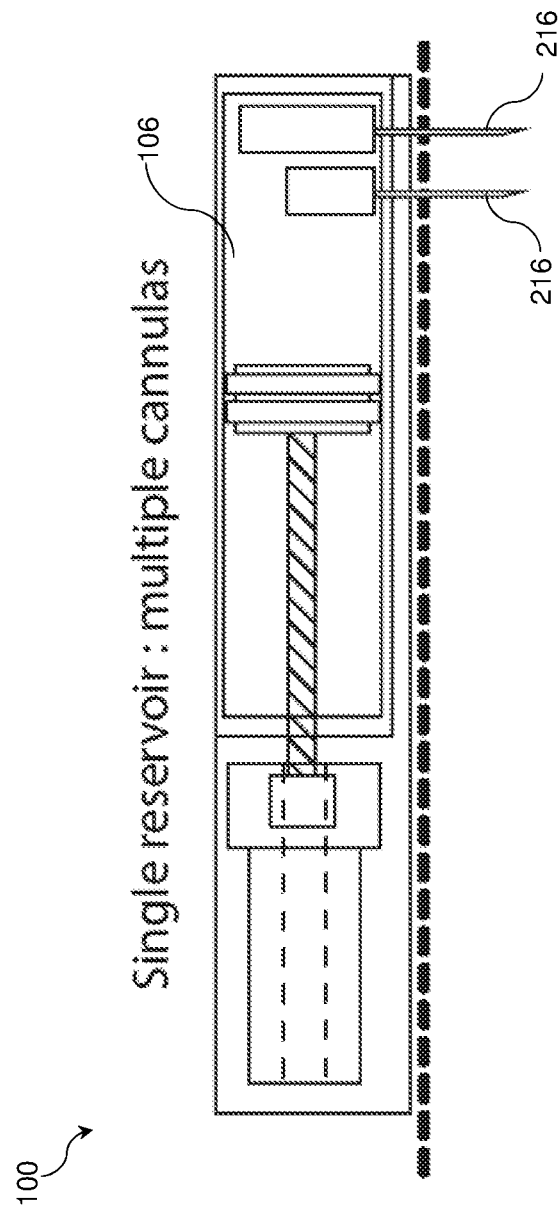

In some embodiments, multiple cannula insertion mechanisms 200 can be used to deliver multiple cannulas 216 into the subcutaneous tissue. An example embodiment of the device 100 having multiple cannulas 216 is shown in FIG. 25A. In some embodiments, the multiple cannulas 216 can be connected to a single reservoir 106 (e.g., see FIG. 25B). In some embodiments including more than one reservoir 106, a separate cannula insertion mechanism 200 can be used to deliver a cannula 216 into the subcutaneous tissue corresponding to each reservoir 106 (e.g., see FIG. 25C). In other embodiments including more than one reservoir 106 (e.g., when more than one reservoir 106 delivers fluid through a single outlet), a single cannula insertion mechanism 200 can be used to deliver a single cannula 216 coupled with more than one reservoir 106 (e.g., see FIG. 25D). In such embodiments, various schemes can be used to control which fluid from which reservoir is delivered through the single cannula 216 at any given time. An example scheme is shown in FIG. 25E that includes a delivery valve 221a for a first reservoir 106a and a delivery valve 221b for a second reservoir 106b. The valves can be independently controllable such that the delivery valve 221a can be open while the delivery valve 221b is closed and vice versa, which can enable delivery of the contents of either reservoir 106a or 106b at a given time. In some cases, both delivery valves 221a and 221b are open which can result in a combination of the contents of reservoirs 106a and 106b being delivered at a given time. In some cases, both delivery valves 221a and 221b are closed and none of the contents are delivered. The delivery valves 221a and 221b can be opened and closed using any technique, e.g., electronically (e.g., with control unit 116), with pressure and/or hydrodynamic forces generated within the device 100, operated as one-way flapper valves, etc. Although the above embodiments were generally described and depicted including two cannulas and/or two reservoirs 106, in various other embodiments any number of cannulas 216 and/or reservoirs 106 can be included. For example, 2, 3, 4, 5, 6, 10, or more cannulas can be included and 2, 3, 4, 5, 6, 10, or more reservoirs 106 can be included.

The use of multiple cannulas 216 and/or multiple reservoirs 106 can have various beneficial advantages For example, the dosage rate can be increased. As another example, the device 100 can be kept in operation if one of the cannulas 216 becomes occluded or otherwise malfunctions. As another example, delivery from the multiple cannulas 216 and/or reservoirs 106 can be performed in an alternating manner, which can have various advantages (e.g., non-constant use of various components can prolong and/or improve their functionality). Embodiments that include multiple reservoirs 106 can enable the delivery of different drugs either intermittently or simultaneously. For example, as described above, one reservoir can contain levodopa and another reservoir can contain carbidopa. In some cases, the different drugs can be delivered through separate cannulas (e.g., see FIG. 25C). In other cases, the different drugs can be delivered through the same cannula (see FIGS. 25D-25E).

In some embodiments, once the device 100 is coupled with the subcutaneous tissue (e.g., via tubing 186 and infusion set 192 or via cannula 216), the device 100 can deliver the contents of the reservoir 106 to the subcutaneous tissue, in some cases at a particular predetermined rate. In some instances, the drive component 112 can be operative to translate the plunger head 120 a predetermined distance over a predetermined time so as to deliver a predetermined amount of fluid over the predetermined time. For example, the drive component 112 (e.g., a DC motor) can be operable to rotate a certain amount (e.g., number of rotations) that will cause load gear 136 to rotate nut 124 a certain number of rotations (e.g., via planetary gear 130, drive gear 132, and idler gear 134) that will cause the lead screw 122 and the plunger head 120 to translate a predetermined distance through the reservoir 106 to evacuate a predetermined amount of fluid to the subcutaneous tissue. In some cases, fluid is delivered to the patient in discrete micro step volumes (e.g., one micro step volume can be delivered based on a certain number or fraction of rotations of the lead screw 122). The micro step volume and delivery rate can combine to determine how often a micro step volume is delivered to the patient. For example, if the micro step is 5 µl and the delivery rate is 40 µl/hour, then a micro step would be delivered to the patient every 7.5 minutes. In other cases, the drive component 112 operates such that fluid is delivered continuously to the subcutaneous tissue. In other cases, the drive component 112 operates such that fluid is delivered in intermittent cycles (e.g., on cycles (when fluid is being delivered) and off cycles (when fluid is not being delivered)). In embodiments in which the drive component 112 is a motor, the motor shaft can include an optical encoder (e.g., encoder disk) to monitor the rotational movement of the motor. As mentioned, the drive component 112 can be controlled by the control unit 116, which in some instances can receive instructions from the filling station 154 and/or the computing device 156.

In some embodiments, the device 100 can include a user interface that the user engages with before the device 100 begins delivery. For example, the user interface can be a mechanical control button 230 (see FIG. 14). In some cases, the user interface can enable the user to toggle the device through various modes, e.g., a priming mode, a delivery mode, and a pause mode. The priming mode can occur at the start of a dosing cycle with a new disposable part 102 and can include priming the system such that the fluidic pathway from the reservoir 106 to the subcutaneous tissue is filled with fluid (e.g., the rigid fluidic link 228, the lower portion 212, and the cannula 216). The delivery mode can include delivery of the fluid into the subcutaneous tissue at a desired rate on a desired schedule. The pause mode can include stopping the delivery of fluid (temporarily or permanently), e.g., if the device 100 needs to be readjusted or removed or for any other reason. In other embodiments, the device 100 can automatically begin delivering fluid once the cannula 216 is delivered into the subcutaneous tissue.

Figure 26:
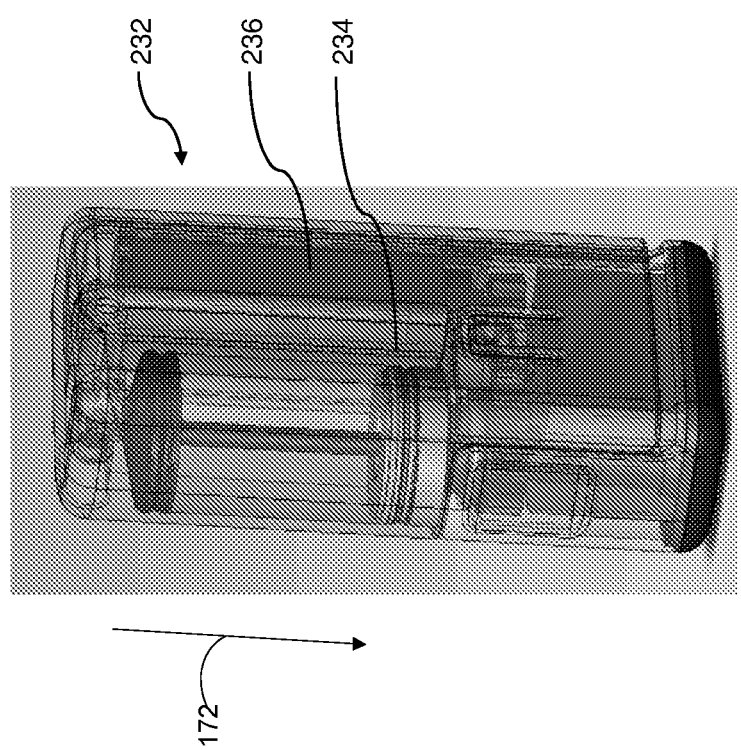
FIG. 26 is a schematic, 3D view showing an antenna sensor of the medicament delivery device, according to some embodiments.

In some embodiments, the device 100 can include sensors to sense various conditions of the device 100, the patient, and/or the environment. For example, as shown in FIG. 26, the device 100 can include an antenna 232 that senses adjacent material. The antenna 232 can have a surface 234 adjacent to the reservoir 106 that senses the fluid level in the reservoir 106 and/or the position of the plunger head 120 in the reservoir 106, which can be used to determine the amount of fluid in the device 100 (e.g., by computing unit 117). The antenna 232 can also have a surface 236 that is substantially parallel with the skin surface of the patient so that the antenna 232 can sense a degree of contact between the device 100 and the skin surface. In some instances, the degree of contact can be measured by measuring an electrical resistivity between at least two locations on the device 100. In some embodiments, the antenna 232 can be a capacitance sensor (e.g., a CapSense® sensor). In some cases, if the degree of contact between the device 100 and skin surface is insufficient, an indicator unit can communicate an alert to the patient (the indicator unit and alerts are described in greater detail below), or, in some cases halt operation of the device 100, at least temporarily. Conversely, the patient can also be alerted if the degree of contact is sufficient.

The device 100 can include various other types of sensors. For example, the device can include a connection sensor for determining connection between the disposable part 102 and the reusable part 104. The connection sensor can include a hall effect sensor that can include a hollow magnet. The sensor can measure an unsymmetrical shape of a metal plate in the disposable part 102 and/or the reusable part 104. In some cases, the connection sensor can measure a level of proximity of the disposable part 102 and the reusable part 104 (e.g., far apart, closer together, attached, etc.). The device 100 can also include physiological sensors for sensing at least one physiological characteristic of the user. The physiological sensors can include; for example (i) a temperature sensor for measuring a skin temperature of the user, (ii) a conductivity sensor for measuring a sweat level of the user, (iii) a movement sensor for measuring body motion of the user, (iv) a neural activity sensor, (v) an oxygen saturation level sensor, (vi) a sound sensor for measuring digestion or bowel activity, (vii) an ECG sensor for detecting a heart rate of the user, and/or (viii) an EMG sensor for detecting a muscle spasm of the user, among many other examples. In some embodiments, some of the above-described sensors can be located remote from the device 100 and communicate with the device 100 via a wired and/or wireless connection. As one non-limiting example, the movement sensor can be worn around the patient's neck or wrist and communicate wirelessly with the device 100.

The device 100 can also include functionality sensors for sensing at least one functional parameter of the device 100. The functional sensors can include, for example, (i) a flow rate sensor for measuring the flow rate of fluid through the device 100, (ii) a pressure sensor for measuring the pressure of the fluid within the device 100 (or the pressure of other locations/components within the device 100), (iii) a DC current sensor for measuring the current delivered to the drive component 112, and/or (iv) a temperature sensor for measuring the temperature of the fluid within the device 100 (or the temperature of other locations/components within the device 100).

Figure 27B:
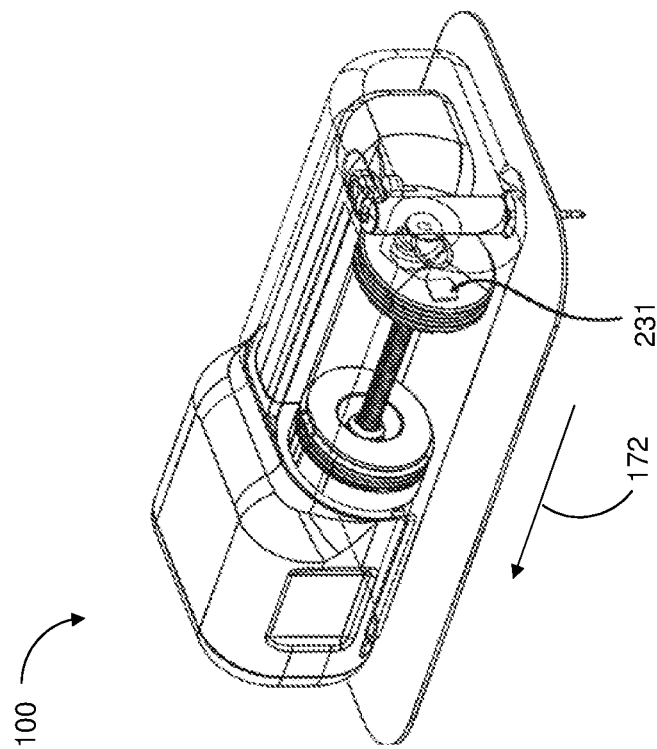
FIGS. 27A-27F are schematic depictions of various sensors that can be included on the delivery device, according to some embodiments.
Figure 27A:
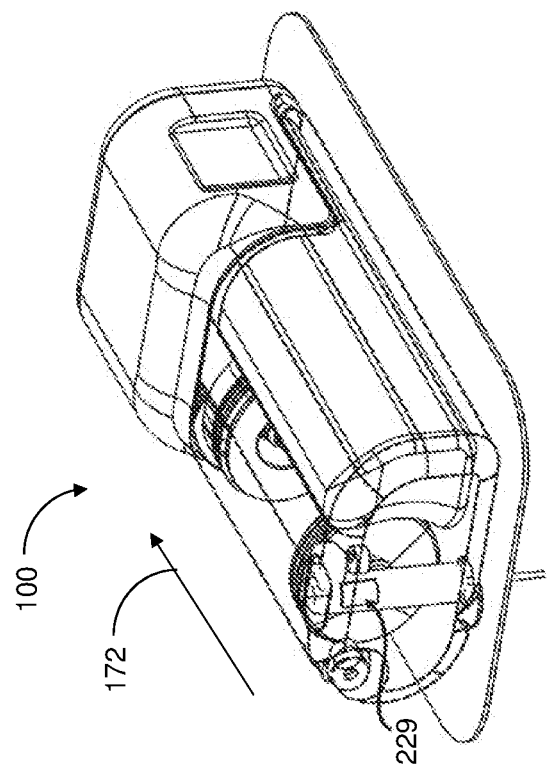

FIG. 27A shows an example flow rate sensor 229. The flow rate sensor 229 can use any flow rate sensing technology, e.g., it can perform echo Doppler measurements to measure the speed of the medicament as it flows through the rigid link 228 and/or the cannula 216. In some instances, measurements from the flow rate sensor 229 or another sensor can be used to determine the actual amount of medicament delivered to patient. In some cases, the actual delivery amount and/or rate can be compared to a programmed amount and/or rate to assess the performance of the device 100 and/or physiological parameters of the patient that may affect delivery (e.g., high and/or low resistivity to injection). The comparison can be performed by the computing unit 117 of the device 100, the processing unit 182 of the filling station 154, and/or another device (e.g., a smartphone). Delivery parameters can then be changed based on the comparison, if necessary. For example, if the actual delivery amount and/or rate is lower than the programmed amount and/or rate, then the control unit 116 can increase the delivery amount and/or rate. Conversely, if the actual delivery amount and/or rate is higher than the programmed amount and/or rate, then the control unit 116 can decrease the delivery amount and/or rate.

FIG. 27B shows an example pressure sensor 231. The pressure sensor 231 can use any pressure sensing technology, e.g., it can be a piezo-electric sensor. As shown in FIG. 27B, in some cases, the pressure sensor 231 can be placed inside the reservoir 106 (e.g., on the plunger head 120). In some instances, the pressure measurements can indicate an issue with the functionality of the device 100. For example, a low pressure measurement can indicate a leak. As another example, a high pressure measurement can indicate an occlusion of the cannula 216. In some instances, the pressure sensor 231 can provide an indication of the resistivity to injection of a particular injection site. For example, if the pressure of the fluid within the cannula 216 (or elsewhere in the device 100) is high it can indicate that the injection site into which fluid is being delivered is resistive to the injection. In some instances, if a particular pressure threshold is exceeded, an alert can be generated to change the injection site (or, in some cases, operation of the device 100 can be halted).

Figure 27D:
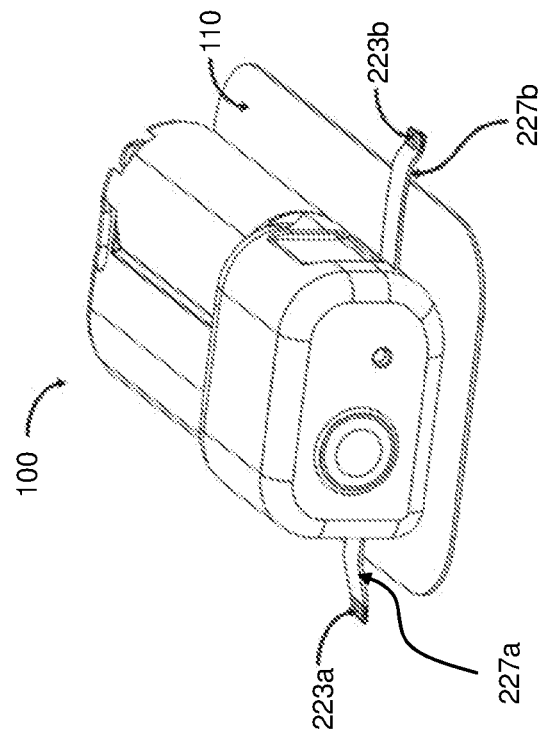
Figure 27C:
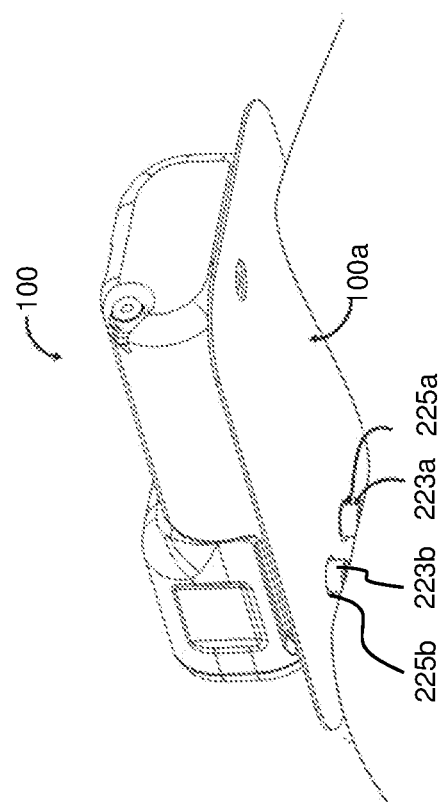

As an alternative or additional technique for determining injection resistivity, the skin impedance can be measured to determine how well the medicament is being absorbed into the body (e.g., by measuring a level of body hydration). For example, if the medicament is not being well absorbed, the skin and/or underlying tissue may have different properties than if the medicament is being well absorbed. FIGS. 27C-27D depict example electrodes 223a, 223b can be used to measure the skin's impedance (in other embodiments, more or less electrodes can be used).

As shown in FIG. 27C, in some instances, the electrodes 223a, 223b are located directly beneath the device 100. For example, the electrodes 223a, 223b can extend through apertures 225a, 225b in the adhesive portion 110. In such instances, the electrodes 223a, 223b can have a spring-like base in order to maintain contact with the patient's skin. As shown in FIG. 27D, in other instances, the electrodes 223a, 223b can be located outside the area directly under the device 100. For example, the electrodes 223a, 223b can extend from the device 100 via tab portions 227a, 227b. In some embodiments, the electrodes 223a, 223b can be located on the reusable part 104 and/or the disposable part 102. In some instances, the electrodes 223a, 223b can communicate with the control unit 116 to generate a closed feedback system in order to improve (or optimize) fluid delivery rates. For example, if the medicament is not being well absorbed, the control unit 116 can decrease (or in some cases increase) the delivery rate and vice versa.

Figure 27F:
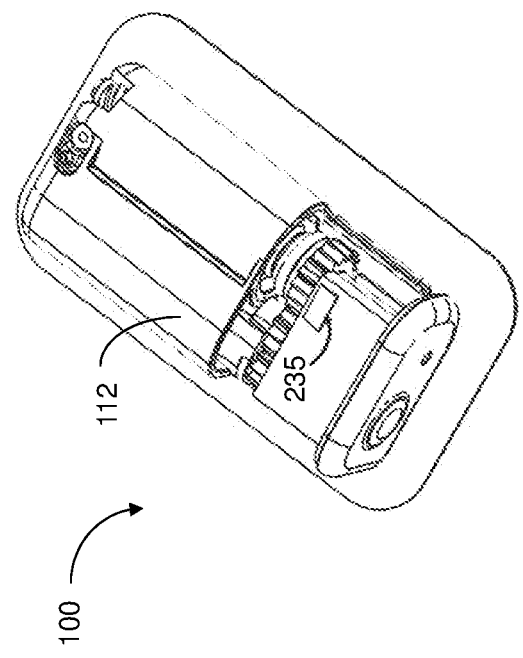
Figure 27E:
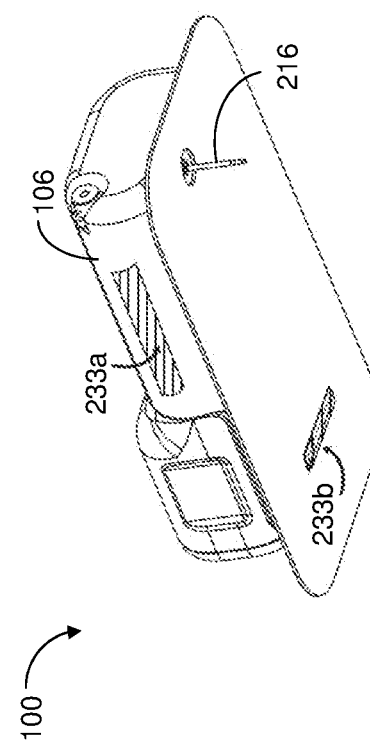

FIG. 27E shows example temperature sensors 233a, 233b. In general, a temperature sensor can be located anywhere on the device. For example, as shown in FIG. 27E, one temperature sensor 233a can be proximate the reservoir 106 to measure a temperature of the contents of the reservoir and another temperature sensor 233b can be proximate the skin surface to measure the temperature of the patient. The temperature sensors 233a, 233b can use any temperature sensing technology, e.g., they can be thermocouples, resistance temperature detectors, thermistors, infrared based devices, silicon-based devices, etc.

FIG. 27F shows an example DC current sensor 235. The DC current sensor 235 can be located at any location on the device 100, e.g., embedded proximate the drive component 112. The DC current sensor 235 can operate using any current sensing technology, e.g., it can be an ampere meter.

The device 100 can also include and/or communicate with medicament level sensors. The medicament level sensors can determine an amount and/or concentration of a particular medicament or other analyte within the blood, tissue, muscle, fat, and/or other biological structures of the patient. In general, the medicament level sensor can sense the amount and/or concentration of any detectable medicament, e.g., levodopa, carbidopa, levodopa/carbidopa combinations, insulin, etc. In some instances, the medicament level sensor is a component within the device 100. In other instances, the medicament level sensor is remote from the device 100, e.g., an external wearable device, a device implanted within the patient, etc. Remote medicament level sensors can communicate with the device via wired and/or wireless connections.

In some embodiments, the control unit 116 can receive signals from the various device sensors (e.g., those mentioned above, among many other examples) and can control the drive component 112 in response to the received signals. In some instances, the control unit 116 can also receive input from the clock of the computing unit 117 (e.g., the time of day) and can control the drive component 112 to deliver fluid based on input from the clock and/or signals received from the sensors. Examples of information that can be communicated to the control unit 116 in signals from the sensors include, e.g., a sleep condition of the user, a food consumption measure for the user, an exercise measure for the user, an amount of movement of the user, a medicament level of the user, a temperature of the user, other physical parameters of the user (e.g., age, height, weight), etc.

As one of many examples, solely for the purpose of illustrating the functionality of the control unit 116, the control unit 116 can receive a signal from a movement sensor (e.g., accelerometer, gyroscope, etc.) on the device 100 indicating that the user experienced above average physical activity for the day. In addition, the control unit 116 can receive an input from the clock indicating that it is 2 PM and, based on information stored in the memory unit 115, the control unit 116 can know that according to the patient's normal eating schedule, he will not eat another meal until 5 PM. Under these conditions, the control unit 116 can be programmed to know that the user should receive an increased dosage of medicament until 5 PM to maintain a stable health condition. The control unit 116 can then control the drive component 112 based on this determination, e.g., the control unit 116 can cause the motor to rotate an additional amount more, to cause the load gear 136 to rotate nut 124 an additional amount (e.g., via planetary gear 130, drive gear 132, and idler gear 134) that will cause the lead screw 122 and the plunger head 120 to translate an additional distance through the reservoir 106 to evacuate an additional amount of fluid to the subcutaneous tissue. In some instances, a drive component module of the control unit 116 is used to control the drive component 112. In some embodiments, the control of the drive component 112 can be performed in an adaptive or a dynamic manner. In this context, the term "adaptive" relates to controlling in response to changes in sensed or measured characteristics (e.g., one or more physiological characteristics of the patient). In this context, the term "dynamic" relates to control through forcefully changing operational parameters of the drive component 112.

As another example, the control unit 116 can receive a signal from a movement sensor (e.g., accelerometer, gyroscope, etc.) on the device 100 (or sometimes remote from the device 100) that provides an indication of a medical condition status of the patient. For example, patients with Parkinson's Disease or other CNS disorders (e.g., essential tremor) sometimes exhibit a more pronounced tremor when they are not properly medicated. Based on the signal from the movement sensor, the control unit 116 can determine whether the amount of medicament being delivered to the patient should be altered (e.g., increased or decreased). For example, if the signal from the movement sensor indicates that the patient is displaying an abnormally pronounced tremor, the control unit 116 can control the drive component 112 to deliver more medicament to the patient. Alternatively, as another example, if the signal from the movement sensor indicates that a patient is moving slowly or sluggishly (a possible side effect of over medication), the control unit 116 can control the drive component 112 to deliver less medicament. In some embodiments, the movement sensor and the control unit 116 can operate in a closed loop feedback system in order to effect desired movement characteristics of the patient (e.g., reduce a tremor).

As another example, the control unit 116 can receive a signal from an ECG sensor measuring the patient's heart rate and/or another movement sensor (e.g., accelerometer) indicating that the patient is exercising or performing another physically strenuous activity. Based on the signal, the control unit 116 can alter the dosage of medicament being delivered to the patient (e.g., increase or decrease the dosage). In some cases, the dosage can be altered to varying degrees, corresponding to a variance between the measured heart rate and a resting heart rate.

As another example, the control unit 116 can receive a signal from a sound sensor or another sensor indicating that the patient is digesting food (e.g., the sound sensor can detect sounds from the digestive system (e.g., stomach, intestines, bowels) characteristic of food being digested).

In some cases, the sensors can determine a relative amount of food consumed. Based on the signal, the control unit 116 can alter the dosage of medicament being delivered to the patient (e.g., increase or decrease the dosage).

As another example, the control unit 116 can receive a signal from the medicament level sensor and control the drive component 112 to deliver medicament in response to that signal. For example, if the signal from the medicament level sensor indicates that the medicament level is low, the control unit 116 can control the drive component 112 to deliver more medicament. Conversely, if the signal from the medicament level sensor indicates that the medicament level is high, the control unit 116 can control the drive component 112 to deliver less medicament (or, in some cases, halt delivery of medicament, at least temporarily). In this way, the medicament level sensor and the control unit 116 can form a closed loop feedback system to maintain a desired medicament level.

As another example, the control unit 116 can receive a signal from a sensor indicating a sleep condition and/or sleep stage of the user. The sensor can be any type of sensor capable of determining a sleep condition and/or stage, e.g., an accelerometer, a clock, polysomnography devices (e.g., electroencephalogram (EEG) sensors, electrocochleogram (EOG) sensors, electrocardiogram (ECG) sensors, electromyogram (EMG) sensors, oxygen level sensors, breathing/air flow sensors, microphone), etc. Based on the signal, the control unit 116 can alter the dosage of medicament being delivered to the patient (e.g., increase or decrease the dosage). In some cases, medicament is only delivered when the patient is in a particular sleep condition or stage. For example, medicament is only delivered if the patient is in REM sleep or deep sleep. In other cases, no medicament is delivered when the patient is in particular sleep conditions or stages. In other cases, medicament is continually delivered, but the dosage is varied depending on the sleep condition and/or stage.

In some embodiments, the dosage can be delivered to control the patient's medical condition/status in accordance with the patient's sleep schedule. As one of many examples, the dosage to a patient with Parkinson's Disease can be controlled such that the patient wakes up in "ON state" (the concepts of "ON state" and "OFF state" relate to stages experiences by a patient with Parkinson's Disease, in which a patient generally feels better during the "ON state" in which a medicament is controlling symptoms and generally feels worse during the "OFF state" in which the medicament is not controlling symptoms; these concepts are well understood by those skilled in the art and should not be confused with the "on period" and "off period" of medicament delivery described elsewhere in this application). In some instances, a user can instruct the control unit 116 regarding the patient's sleep schedule, e.g., by inputting a wake-up time and fall-asleep time into a GUI presented by the filling station 154, the computing device 156, and/or the device 100 itself. The sleep schedule may be stored in the memory unit 115. For example, if the user inputs a wake up time of 6 AM, the control unit 116 can alter the dosage delivery schedule such that the patient will be in "ON state" at 6 AM. The exact delivery schedule will depend on the individual patient, e.g., the device 100 may switch to delivering more medicament at 2 AM, 4 AM, etc. As another example, if the user inputs a fall asleep time of 10 PM, the control unit 116 can alter the dosage delivery schedule such that the patient will not enter "OFF state" until they are already asleep (e.g., not until 11 PM). Many additional examples of altering dosage rates based on the patient's sleep schedule are possible.

In general, the device 100 can be adapted or configured to alter the dosage amount from an "ON state" amount (e.g., day schedule) to an "OFF state" amount (e.g., night schedule) at any time of day or night.

Similarly, the device 100 can be adapted or configured to alter the dosage amount from an "OFF state" amount (e.g., night schedule) to an "ON state" amount (e.g., day schedule) at any time of day or night. Thus, the device can accommodate users with any sleep schedule.

Delivering medicament to a patient based on the patient's sleep schedule is an example of a delivery profile. As used herein, delivery profile means a schedule on which medicament is delivered to the patient, which in some cases can be based on the activities and/or environment of the patient. In general, the device 100 is capable of delivering medicament on any schedule within the physical limitations of the device. A few examples include: (i) a delivery profile for a relaxed day at home, which may include delivery of a lower amount of medicament than for a high activity day; (ii) a delivery profile for a high activity day, which may include delivery of a higher amount of medicament than for a relaxed day at home; (iii) a delivery profile for an evening out, which may include delivery of a higher amount of medicament in the evening (e.g., keeping the patient in "ON state" for longer than normal). Many other delivery profiles are possible. In some instances, a user can select pre-programmed delivery profiles from a GUI presented by the filling station 154, the computing device 156, and/or another device. In some instances, a user can program the device 100 to deliver a custom delivery profile.

In some embodiments, the computing unit 117 can include a module that monitors the control unit 116 (or any other unit) and mitigates processing malfunctions (e.g., hang outs, freeze conditions, etc.) In some cases, the monitoring module can be a watchdog. The monitoring module can be implemented on a separate circuit or even a different board from the control unit 116. In some instances, the monitoring module can be programmed to receive an acknowledge signal from the control unit 116 during a repeating time period. If the monitoring module does not receive an update during a particular time period it can generate a signal to reset the control unit 116. The computing unit 117 can also verify the device's connection to the cloud (or in some cases the processing unit 182 can verify the filling station's connection to the cloud).

In some embodiments, the device 100 can provide information and/or alerts to the patient before, during, and/or after delivery, e.g., based on the data collected by the sensors described above (among many others). The device 100 can include any type of indicator unit capable of communication with the patient, e.g., via visual, audible, and/or haptic feedback. The indicator unit can communicate any amount of information collected by the sensors. As one example, the indicator unit can include a single light that communicates the remaining amount of fluid in the reservoir 106. For example, the light can be green, yellow, or red depending on the amount of fluid remaining. In some cases the intensity of the signal delivered to the patient can increase as the reservoir 106 gets closer to being empty. For example, a warning signal (e.g., a yellow light, a single sound, a single vibration) can be generated when the reservoir 106 has a first predetermined amount remaining (e.g., 20%), a replace signal (e.g., a red light, multiple sounds, multiple vibrations) can be generated when the reservoir 106 has a second predetermined amount remaining (e.g., 10%), and an emergency replace signal (e.g., flashing red light, repeated sound, repeated vibrations) can be generated when the reservoir is empty (e.g., 5% or less). As another example, the indicator unit can communicate if the patient's medicament level is too high and/or too low (e.g., as determined by the medicament level sensor). As yet another example, the indicator unit can communicate if the device malfunctions and needs to be readjusted or replaced (e.g., if the control unit 116 freezes, if pressure in the device is abnormal, if contact with the skin is insufficient, among many other examples). As a further another example, the indicator unit can include a screen display that digitally communicates the data being collected by the sensors (or a subset thereof) to the patient. In some instances, the patient's status can be taken into account when determining the intensity of an alert. For example, if the patient is sleeping, the alert may be more intense (e.g., louder, longer, brighter, etc.) to ensure that the patient is alerted. Alternatively, if the alert is noncritical, the alert may be less intense if the patient is sleeping, so as to not disturb the patient. In some embodiments, the indicator unit can provide many additional feedbacks.

The indicator unit can also provide a feedback when the disposable part 102 and reusable part 104 are attached and/or detached. In some instances, if the disposable part 102 and reusable part 104 are not properly attached, then operation of the pump cannot occur (e.g., the control unit 116 will not initiate the filling and/or delivery operations). In some instances, if the disposable part 102 and reusable part 104 become detached during operation of the pump, then the operation can be stopped (e.g., the control unit 116 can stop the filling and/or delivery operations). Operations may be initiated (or resumed) once the disposable part 102 and reusable part 104 are attached (or reattached).

In some embodiments, all data collected by the sensors described above (among many other examples) can be communicated to the filling station 154, the computing device 156, and/or the cloud, as initially described above. In some cases, the data (or a subset thereof) is communicated, processed, and/or displayed in real time as it is being collected (e.g., to alert a caregiver, medical professional, and/or patient to an emergency situation). In other cases, the data (or a subset thereof) is downloaded, processed, and/or displayed solely when the device 100 is placed in the filling station 154.

Figure 28:
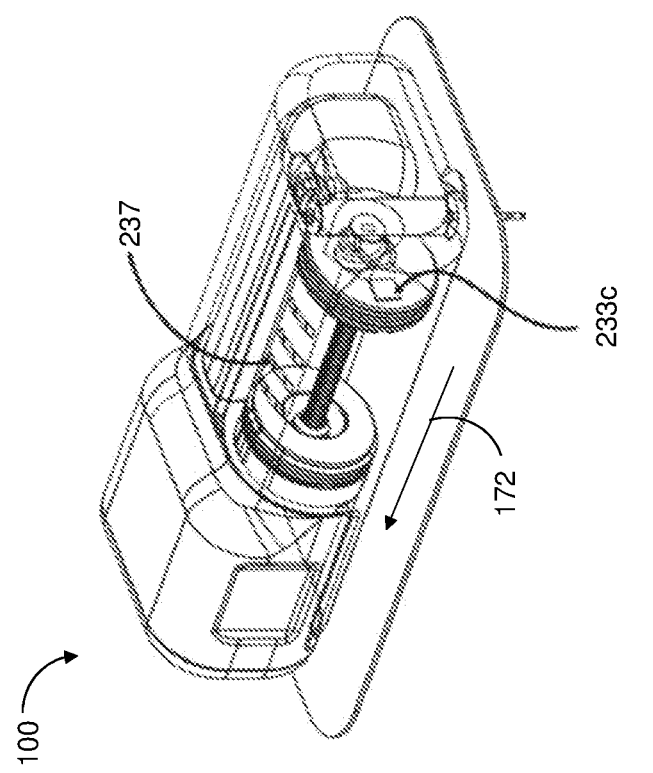
FIG. 28 is a schematic, 3D view of a temperature control unit of the delivery device, according to some embodiments.

In some embodiments, the device 100 can include units for additional control over the fluid delivery process. For example, the device 100 can include a temperature control unit 237 that can control the temperature of the fluid and/or other components of the device 100, as shown for example in FIG. 28. In general, the temperature of the fluid can be controlled to be any advantageous temperature. For example, the temperature of the fluid can be controlled to be within a range from about 4° Celsius to about 40° Celsius. Many other temperature ranges are contemplated. For example, in some embodiments, every integer value within the range of about 4° Celsius to about 40° Celsius (e.g., 5° C., 6° C., 7° C., etc.) can be a minimum or a maximum within a subrange with any other integer value within the range. A few example temperature ranges include about 8° C. to about 15° C., about 22° C. to about 37° C., and about 32° C. to about 42° C. In some instances, the temperature control unit 237 can control the temperature of the drug to be within an effective range for that particular drug. In embodiments in which the device 100 contains multiple drugs, each drug can be maintained at a different temperature (or within a different temperature range). In other instances, all drugs can be maintained at the same temperature (or within the same temperature range).

The temperature control unit 237 can include components that heat, cool, and/or thermally isolate the fluid. In general, the temperature control unit 237 can include any components capable of performing these actions, e.g., a heating element, a cooling element, a thermoelectric module, a thermally isolating jacket, etc. In some instances, the temperature control unit 237 can heat and/or cool the fluid while it is in the reservoir 106. In some instances, the temperature control unit 237 can heat and/or cool the fluid while it is in the cannula 216. In some embodiments, the temperature control unit 237 can include a temperature sensor (see FIG. 27E) for sensing fluid temperature at various locations in the device 100, that can be used as an input to the control unit 116 and/or another components. In some instances, the temperature control unit 237 includes a temperature sensor at the delivery site from the cannula 216 (e.g., tip 215 and/or sidewall aperture 217), as shown for example by sensor 233c. Based on the measurements from the temperature sensor the unit can heat and/or cool the fluid using various techniques (e.g., thermoelectric techniques that use the Peltier effect).

Figure 29A:
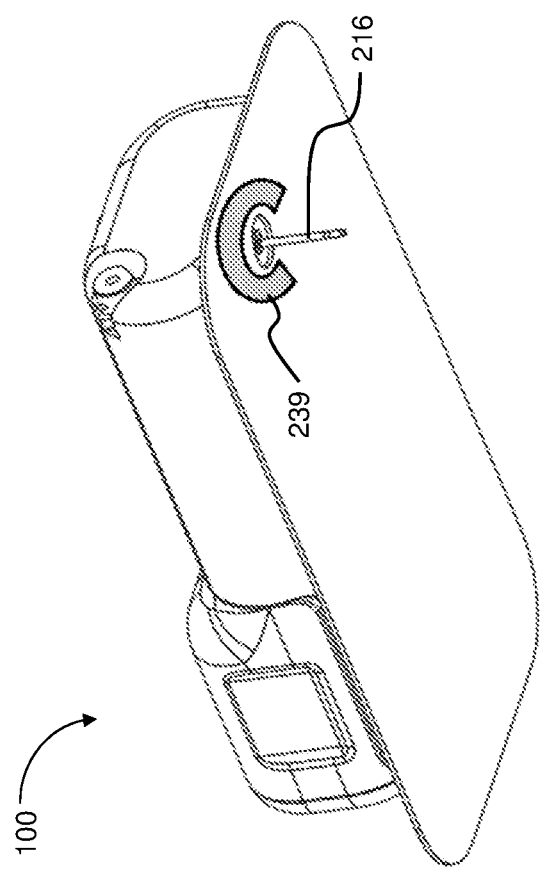

In some embodiments, the device 100 can include a skin/tissue property control unit 239 used for controlling the properties of the skin surface at a delivery site, as shown for example in FIG. 29A. In general any property of the skin can be controlled. For example, the skin/tissue property control unit 239 can include a vibration unit that causes ultrasonic vibration of the skin/tissue, which can facilitate easier introduction and/or disbursement of the medicament within the tissue. As another example, the skin/tissue property control unit 239 can prepare the skin for cannula insertion and/or medicament delivery. For example, the control unit 239 can include an agent delivery unit that can delivery lubricating agents, therapeutic agents, etc., that can enhance the receptiveness of the skin/tissue to the cannula 216 and/or fluid. Many other examples are possible.

In some embodiments, the device 100 can include a skin/tissue detection unit 241 for detecting the properties of the tissue that surround the cannula 216, e.g., once the cannula 216 is delivered into the tissue. An example skin/tissue detection unit 241 is shown in FIGS. 29B-C. In some cases, the detection unit 241 can determine the type of biological material (e.g., tissue) surrounding the cannula 216 (e.g., dermis, skin, fat, blood vessel, bone, muscle, etc.) For example, the type of biological material can be identified by measuring the impedance between two electrodes 243a, 243b located on the cannula 216. The measured impedance can be mapped to known values for various biological materials.

Figure 30:
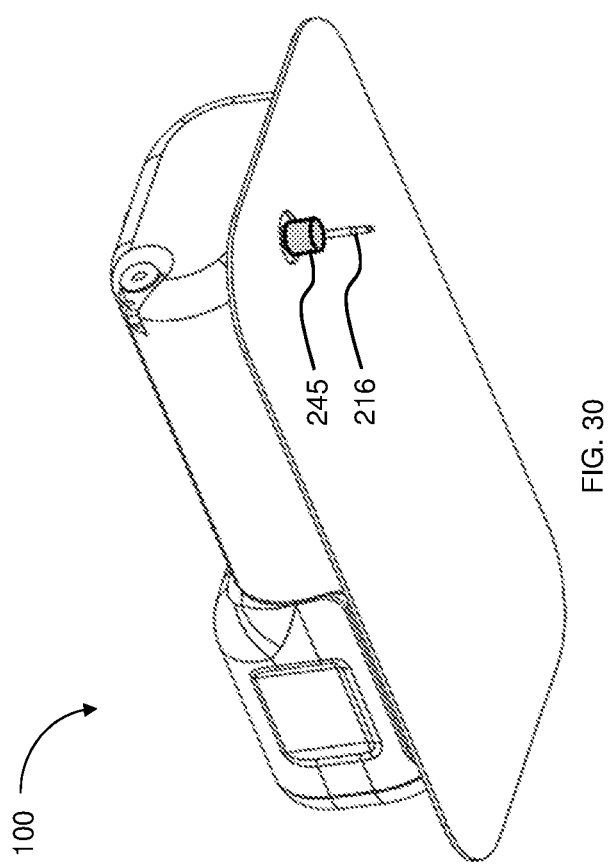
FIG. 30 is a schematic, 3D view of a cannula opening unit of the delivery device, according to some embodiments.

In some embodiments, the device 100 can include a cannula opening unit 245 for opening an occluded or partially occluded cannula 216, as shown for example in FIG. 30. For example, the cannula 216 may be occluded with medicament, skin, tissue, and/or other matter. In general, any technique for opening the cannula 216 can be used. For example, the opening unit 245 can be a vibrating unit that applies ultrasonic vibrations to the cannula 216. As another example, a suction force can be applied to the cannula 216. As yet another example, the cannula 216 can be heated (e.g., q tip heating) and/or cooled.

Figure 31:
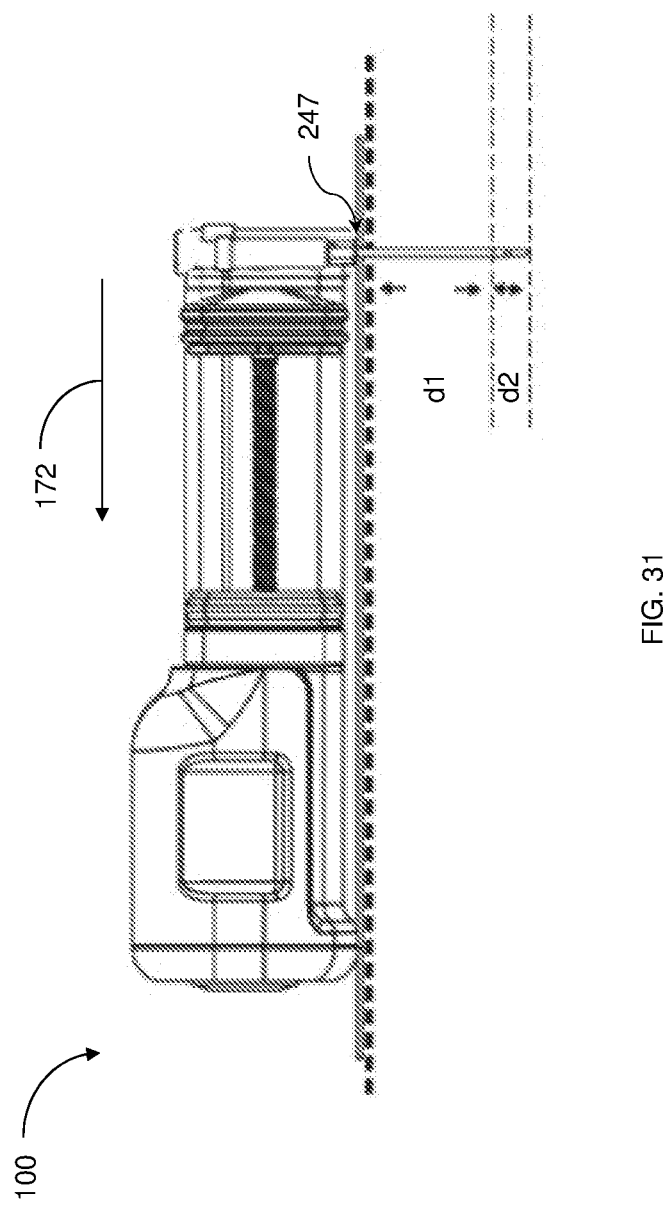
FIG. 31 is a schematic, 3D view of a depth penetration control unit of the delivery device, according to some embodiments.

In some embodiments, the device 100 can include a depth penetration control unit 247 for controlling the depth (or altitude) to which the cannula 216 and/or the needle 214 is inserted into the skin/tissue, as shown for example in FIG. 31. For example, the unit 247 can be used to penetrate the skin/tissue up to a depth d1, e.g., to avoid undesirable contact with the patient's muscle, bone, organs, etc., which may located at additional depth d2. In some instances, the unit can include a sensor that performs subcutaneous inspection, e.g., via an optical system that delivers and receives infrared (or other wavelength) waves into the body at an identified treatment site. If the optical system identifies that there is an undesirable structure located at a depth to which the cannula 216 and/or the needle 214 will be delivered, then the delivery system can be deactivated. This can be accomplished in many ways, e.g., blocking an aperture through which the cannula 216 and/or the needle 214 is delivered. In other embodiments, the depth penetration control unit 247 can deliver the needle 214 and/or the cannula 216 further into the tissue to a desired position and/or retract the needle 214 and/or the cannula 216 back to a desired position. In some embodiments, the adjustment of the needle 214 and/or the cannula 216 position can be automatically controlled (e.g., by control unit 116 or by a controller of the cannula insertion mechanism 200). In other embodiments, a manual technique can be used in which the user can manually adjust the position of the needle 214 and/or the cannula 216 (e.g., by manipulating the cannula insertion mechanism 200 and/or by delivering needles 214 and/or cannulas 216 of varying lengths).

As mentioned above, the patient can receive a signal (e.g., visual, audible, and/or haptic feedback) when the reservoir 106 is empty or close to empty. At this point, the patient can remove the device 100 (e.g., disconnect a standalone pump from the belt and infusion sets 192, remove a patch pump from a skin surface, etc.), detach the disposable part 102 from the reusable part 104, dispose of the disposable part 102, attach the reusable part 104 to a new disposable part 102, and repeat the filling and delivery process described above.

Figure 32:
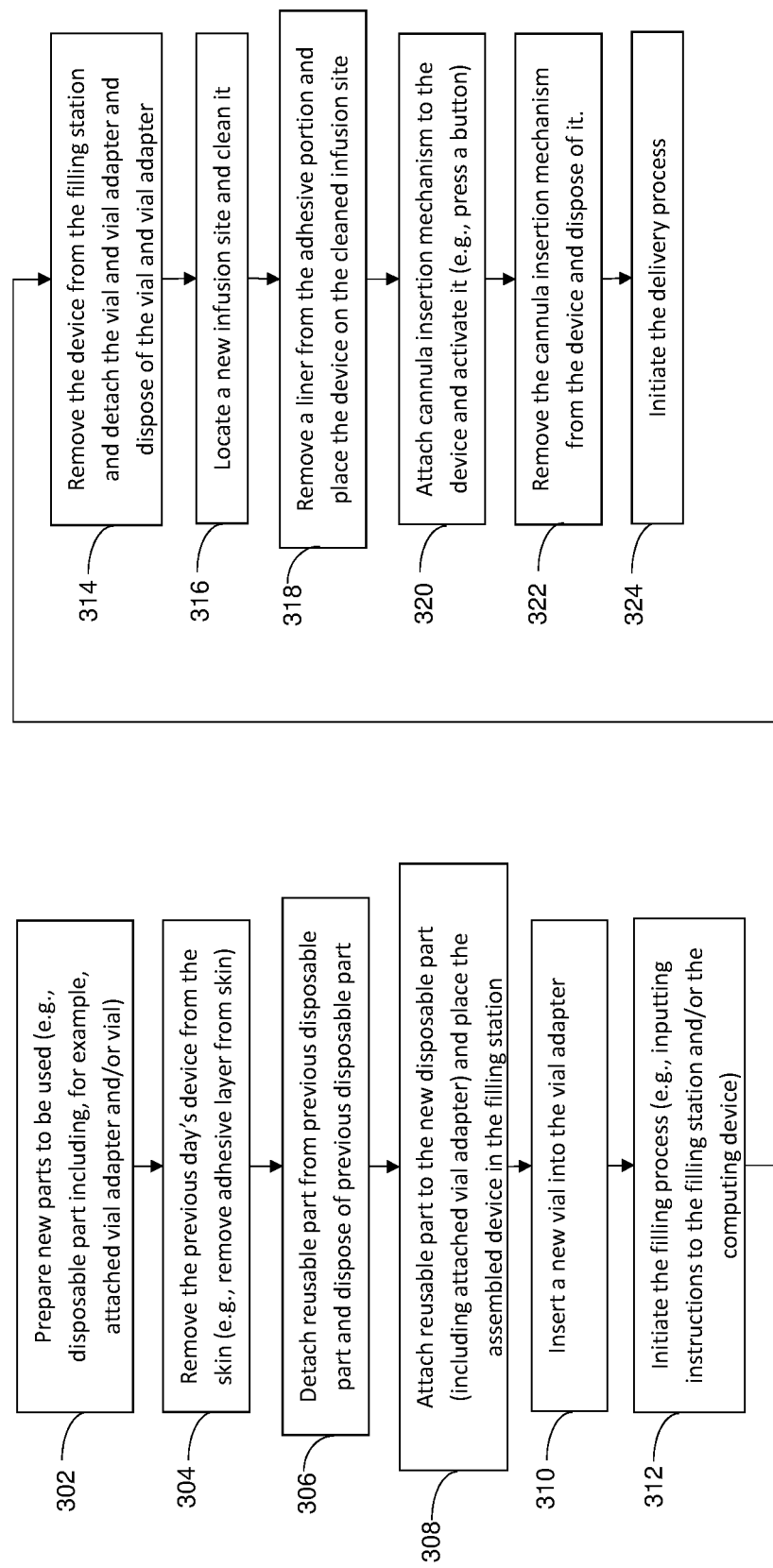
FIG. 32 is a flowchart showing example steps performed by a patient using the medicament delivery device, according to some embodiments.

FIG. 32 is a flowchart showing example daily steps 300 that can be taken by patients using the device 100. At step 302, the patient can prepare new parts to be used (e.g., the disposable part (including attached vial adapter) and the vial). At step 304, the patient can remove the previous day's device from the skin (e.g., remove the adhesive layer from the skin). At step 306, the patient can detach the reusable part from the previous disposable part and dispose of the previous disposable part. At step 308, the patient can attach the reusable part to the new disposable part (including attached vial adapter) and place the assembled device into the filling station. At step 310, the patient can insert a new vial into the vial adapter. At step 312, the patient can initiate the filling process by inputting instructions to the filling station and/or the computing device. At step 314, once the filling process is complete, the patient can remove the device from the filling station and detach the vial adapter and the vial from the device and dispose of the vial adapter and the vial. At step 316, the patient can locate a new infusion site and clean it (e.g., with an alcohol wipe). At step 318, the patient can remove a liner from the adhesive portion and place the device on the cleaned infusion site. At step 320, the patient can attach the cannula insertion mechanism to the device and activate the cannula insertion mechanism (e.g., by pressing a button). At step 322, the patient can remove the cannula insertion mechanism from the device and dispose of it. At step 324, the patient can initiate the delivery process (e.g., by pressing a button on the device). After the reservoir is depleted, the steps 300 can be repeated. In some embodiments, some or all of the above steps 300 can be performed by someone other than the patient (e.g., caregiver, medical professional, etc.) Further the above steps 300 are provided for purposes of example only; in other embodiments, some of the above steps are not performed and other steps are performed.

FIG. 33 is a chart providing minimum, maximum, and nominal values for certain parameters related to the configuration and operation of the device 100, according to some embodiments. Every value between the minimum value and the maximum value for each parameter shown in FIG. 33 (not just the nominal value), is contemplated and expressly supported herein, subject to the number of significant digits expressed in each particular range.

Fluid Medicaments

Contemplated fluid medicaments, i.e., pharmaceutically acceptable formulations, that can be contained within and/or delivered by the device 100 may include compositions that comprise carbidopa, levodopa, carbidopa esters, and/or levodopa esters (e.g., a levodopa or a carbidopa phosphoester or alkyl ester). In certain embodiments, the formulation is a carbidopa, levodopa, or a carbidopa/levodopa formulation that also includes two or more antioxidants, e.g., (a) ascorbic acid or a salt thereof (e.g., sodium ascorbate) and (b) another antioxidant, such as cysteine or a cysteine derivative (for example, L-cysteine or N-acetylcysteine (NAC), glutathione, or diacetylcystine), or a sulfite (e.g., sodium sulfite). Such pharmaceutically acceptable formulations can include: levodopa; about 0.1% to about 6% by weight carbidopa; about 1% to about 25% by weight arginine, or meglumine, or a combination thereof; and/or at least one o-quinone scavenger. In other embodiments, a formulation includes: about 8% to about 16% (e.g., about 11% to about 15% or about 12% to about 14%) by weight levodopa; about 1% to about 4% by weight carbidopa; about 0.1% to about 40% by weight of arginine, meglumine, a o-quinone scavenger, or any suitable combination thereof. In these embodiments, the pharmaceutically acceptable formulation can have less than about 10.0 μg/ml, less than about 5.0 μg/ml, less than about 2.5.0 μg/ml, less than about 1.0 μg/ml, less than about 0.75 μg/ml, less than about 0.5 μg/ml, less than about 0.25 μg/ml, less than about 0.1 μg/ml, less than about 0.05 μg/ml, or less than about 0.025 μg/ml of hydrazine, e.g., as determined by a gas chromatography-mass spectrometry (GCMS) method. In particular embodiments, the formulation has less than about 0.1 μg/ml of hydrazine or less than about 0.05 μg/ml of hydrazine or about 0.1 μg/ml of hydrazine to about 0.5 μg/ml of hydrazine, e.g., as determined by a GCMS method.

Contemplated liquid medicaments may include an o-quinone scavenger selected from the group consisting of: ascorbic acid and/or a salt thereof, L-cysteine, NAC, glutathione, diacetylcystine and/or a salt thereof, and a combination thereof. A formulation may further include about 0.1% to about 10% by weight ascorbic acid or a salt thereof and a component selected from the group consisting of about 0.01% to about 1% by weight of NAC, about 0.01% to about 1% by weight Lcysteine, about 0.001% to about 1% by weight glutathione, about 0.001% to about 1% by weight diacetylcystine or a salt thereof, or any combination thereof.

In other embodiments, a pharmaceutically acceptable liquid formulation includes (a) carbidopa (e.g., about 0.1% to about 10% carbidopa); (b) ascorbic acid or a salt thereof; and (c) one of L-cysteine, NAC, glutathione, and diacetyl-cystine, or a salt thereof. The formulation may for example include less than about 10.0 μg/ml, less than about 5.0 μg/ml, less than about 2.5.0 μg/ml, 1.0 μg/ml 1.0 μg/ml, less than 0.75 μg/ml, less than 0.5 μg/ml, less than 0.25 μg/ml, less than 0.1 μg/ml, less than 0.05 μg/ml, or less than 0.025 μg/ml of hydrazine, e.g., as determined by a GCMS method. In particular embodiments, the formulation has less than about 0.1 μg/ml of hydrazine, less than about 0.05 μg/ml of hydrazine, or about 0.1 μg/ml to about 0.5 μg/ml of hydrazine, e.g., as determined by a GCMS method. The formulation may include about 0.1% to 10% (e.g., about 0.3% to about 2%, about 0.5%, about 1.0% to about 1.3%, about 1.2%, or about 1.3%) by weight ascorbic acid. The formulation may include about 0.01% to about 1% (e.g., about 0.1% to about 0.6%, about 0.3%, about 0.4%, about 0.5%, about 0.6%, or about 0.8%) by weight Lcysteine, or a salt thereof. The formulation may include about 0.1% to about 10% (e.g., about 0.1% to about 6%, about 0.1% to about 4%, about 0.6% to about 1.4%, about 1.2% to about 4%, about 0.75%, about 1.4%, about 3%, or about 3.3%) by weight carbidopa. The formulation may include about 0.1% to about 10% (e.g., about 0.4% to about 0.6%, about 0.4% to about 1%, about 0.5%, or about 1.2%) by weight ascorbic acid, or a salt thereof. The formulation may include about 0.01% to about 1% (e.g., about 0.1% to about 1%, about 0.3%, about 0.4%, about 0.5%, about 0.6%, about 0.7%, or about 0.8%) by weight L-cysteine or NAC. The formulation may include, for example, less than about 4% (e.g., less than about 2%, less than about 1%, less than about 0.5%, less than about 0.1%, less than about 0.05%, or less than about 0.01%) by weight levodopa, or may not include levodopa. In certain embodiments, the formulation includes levodopa (e.g., about 2% to about 16%, about 2% to about 8%, about 8% to about 16%, about 6% to about 12%, about 15%, about 2% to about 16%, about 12%, or about 13% by weight levodopa). The formulation may further comprise arginine, meglumine, or a combination thereof, for example, about 0.1% to about 40%, about 1% to about 25%, about 10% to about 25%, about 12% to about 40%, about 32% to about 42%, or about 15% to about 16% by weight arginine, meglumine, or any suitable combination thereof.

| Components | Exemplary Amount | Exemplary amount |
|---|---|---|
| Levodopa | 0-16% | 5-7% |
| Carbidopa | 0.1-6% | 0.6-1.5% |
| Arginine | 0.1-40% | 14-16% |
| Ascorbic acid or Na ascorbate | 0.1-10% | 03-0.7% |
| L-cysteine or NAC or glutathione | 0.01-1% | 03-0.5% |

In particular embodiments, the formulation includes about 2% to about 8% by weight levodopa, about 0.1% to about 3% by weight carbidopa, about 10% to about 25% by weight arginine, about 0.1% to about 10% (e.g., about 0.3% to about 2%) by weight ascorbic acid or a salt thereof, and about 0.001% to about 5% by weight L-cysteine or a salt thereof. In other embodiments, the formulation includes: about 8% to about 16% by weight levodopa; about 1% to about 4% by weight carbidopa; about 12% to about 40% by weight of a component selected from the group consisting of arginine, or of meglumine, or a combination thereof; about 0.1% to about 10% by weight ascorbic acid or a salt thereof; about 0.001% to about 1% by weight L-cysteine or a salt thereof, or any combination of the aforesaid. In these embodiments, the formulation has less than about 0.5 or 0.1 μg/ml hydrazine (e.g., less than about 0.05 or less than about 0.01 μg/ml hydrazine), as determined by GCMS. The formulation may include the components in the following Tables:

| Components | Exemplary Amount | Exemplary amount |
|---|---|---|
| Levodopa | 4-8% | 5-7% |
| Carbidopa | 0.5-2% | 0.6-1.5% |
| Arginine | 13-18% | 14-16% |
| Ascorbic acid | 0.1-2% | 0.3-0.7% |
| L-cysteine, cysteine HCl, and/or N-acetyl cysteine | 0.1-2% | 0.3-0.5% |
| Levodopa | 10-15% | 12-15% |
| Carbidopa | 1.2-4% | 2-4% |
| Arginine/meglumine or a combination thereof | 25-40% | 30-38% |
| Ascorbic acid or sodium ascorbate | 0.1-2% | 0.3-0.7% |
| L-cysteine or cysteine-HCl | 0.1-1% | 0.2-0.5% |

In other particular embodiments, the formulation includes about 2% to about 8% by weight levodopa, about 0.1% to about 3% by weight carbidopa, about 10% to about 25% by weight arginine, about 0.1% to about 10% by weight ascorbic acid or a salt thereof, and about 0.001% to about 5% by weight NAC. In other embodiments, the formulation includes: about 8% to about 16% by weight levodopa; about 1% to about 4% by weight carbidopa; about 12% to about 40% by weight of a component selected from the group consisting of arginine, or meglumine, or a combination thereof; about 0.1% to about 10% by weight ascorbic acid or a salt thereof; about 0.001% to about 1% by weight NAC, or any combination of the aforesaid. In these embodiments, the formulation has less than about 0.5 μg/ml or less than about 0.1 μg/ml hydrazine (e.g., less than 0.05 μg/ml or less than about 0.01 μg/ml hydrazine), as determined by GCMS. The formulation may include the components in the following Tables:

| Components | Exemplary Amount | Exemplary amount |
|---|---|---|
| Levodopa | 4-8% | 5-7% |
| Carbidopa | 0.5-2% | 0.6-1.5% |
| Arginine | 13-18% | 14-16% |
| Ascorbic acid | 0.1-2% | 0.3-0.7% |
| NAC | 0.1-2% | 0.3-0.5% |
| Levodopa | 10-15% | 12-15% |
| Carbidopa | 1.2-4% | 2-4% |
| Arginine/meglumine or a combination thereof | 25-40% | 30-38% |
| Ascorbic acid or sodium ascorbate | 0.1-2% | 0.3-0.7% |
| NAC | 0.1-1% | 0.2-0.5% |

In particular embodiments, the formulation includes about 2% to about 8% by weight levodopa, about 0.1% to about 3% by weight carbidopa, about 10% to about 25% by weight arginine, about 0.1% to about 10% by weight ascorbic acid or a salt thereof, and about 0.001% to about 5% by weight glutathione. In other embodiments, the formulation includes: about 8% to about 16% by weight levodopa; about 1% to about 4% by weight carbidopa; about 12% to about 40% by weight of a component selected from the group consisting of arginine, or meglumine, or a combination thereof; about 0.1% to about 10% by weight ascorbic acid or a salt thereof; about 0.001% to about 1% by weight glutathione, or any combination of the aforesaid. In these embodiments, the formulation has for example less than about 0.5 µg/ml or less than about 0.1 µg/ml hydrazine (e.g., less than about 0.05 µg/ml or less than about 0.01 µg/ml hydrazine), as determined by GCMS. The formulation may include the components in the following Tables:

| Components | Exemplary amount | Exemplary amount |
|---|---|---|
| Levodopa | 4-8% | 5-7% |
| Carbidopa | 0.5-2% | 0.6-1.5% |
| Arginine | 13-18% | 14-16% |
| Ascorbic acid | 0.1-2% | 0.3-0.7% |
| Glutathione | 0.1-2% | 0.3-0.5% |
| Levodopa | 10-15% | 12-15% |
| Carbidopa | 1.2-4% | 2-4% |
| Arginine/meglumine or a combination thereof | 25-40% | 30-38% |
| Ascorbic acid or sodium ascorbate | 0.1-2% | 03-0.7% |
| Glutathione | 0.1-1% | 0.2-0.5% |

In particular embodiments, the formulation includes about 2% to about 8% by weight levodopa, about 0.1% to about 3% by weight carbidopa, about 10% to about 25% by weight arginine, about 0.1% to about 10% by weight ascorbic acid or a salt thereof, and about 0.001% to about 5% by weight diacetylcystine or a salt thereof. In other embodiments, the formulation includes: about 8% to about 16% by weight levodopa; about 1% to about 4% by weight carbidopa; about 12% to about 40% by weight of a component selected from the group consisting of arginine, or meglumine, or a combination thereof; about 0.1% to about 10% by weight ascorbic acid, and/or a salt thereof; about 0.001% to about 1% by weight diacetylcystine or a salt thereof, or any combination of the aforesaid. In these embodiments, the formulation has for example less than about 0.5 µg/ml or less than about 0.1 µg/ml hydrazine (e.g., less than 0.05 µg/ml or less than 0.01 µg/ml hydrazine), as determined by GCMS. The formulation may include the components in the following Tables:

| Components | Exemplary amount | Exemplary amount |
|---|---|---|
| Levodopa | 4-8% | 5-7% |
| Carbidopa | 0.5-2% | 0.6-1.5% |
| Arginine | 13-18% | 14-16% |
| Ascorbic acid | 0.1-2% | 0.3-0.7% |
| Diacetylcystine | 0.1-2% | 0.3-0.5% |
| Levodopa | 10-15% | 12-15% |
| Carbidopa | 1.2-4% | 2-4% |
| Arginine/meglumine or a combination thereof | 25-40% | 30-38% |
| Ascorbic acid or sodium ascorbate | 0.1-2% | 0.3-0.7% |
| Diacetylcystine | 0.1-1% | 0.2-0.5% |

The formulation of any of the above embodiments may include a surfactant. The surfactant may be any of one of polysorbate 20, 40, 60, or 80, or any combination thereof. In particular embodiments, the formulation includes about 0.01% to about 5% surfactant (e.g., polysorbate 80) or about 0.1% to 0.5% surfactant (e.g., polysorbate 80). In more particular embodiments, the formulation includes about 0.3% surfactant (e.g., polysorbate 80).

The formulation of any of the above embodiments may include about 11% to about 15% by weight levodopa. For example, the formulation may include about 12% to about 14% by weight levodopa (e.g., about 12% or about 13.2% levodopa).

The formulation of any of the above embodiments may include about 0.6% to about 4%, about 0.8% to about 3%, or about 1.2% to about 4% by weight carbidopa. For example, the formulation may include about 2.5% to about 3.5% (e.g., about 3.0% or about 3.3%) by weight carbidopa.

The formulation of any of the above embodiments may include about 25% to about 40% (e.g., about 32% to about 40%, about 32%, or about 36%) by weight of a component selected from the group consisting of arginine, or meglumine, or a combination thereof. For example, the formulation may include about 32% arginine, about 32% meglumine, about 36% arginine, or about 36% meglumine.

The formulation of any of the above embodiments may, after storage for 1, 2, 3, 4, 6, 8, 10, 12, 15, 18, 20, or 24 hours; 1, 2, 3, 5, 7, 10, 14, 21, 28, or 30 days; 1, 2, 3, 4, 6, 9, or 12 months; or 1, 1.5, 2, 2.5, or 3 years, at 25° C., 2-8° C. or at −20° C., have less than about 0.1 µg/ml of hydrazine, as determined by GCMS. The formulation of any of the above embodiments may have less than about 5% (e.g., less than about 4%, 3%, 2%, 1%, 0.5%, 0.3%, 0.2%, 0.1% or 0.05%) by weight 3,4dihydroxyphenyl-2-methylpropionic acid (Degradant RRT 1.4), relative to the amount of carbidopa, as determined by HPLC.

The formulation of any of the above embodiments may be in a form selected from the group consisting of a liquid, a gel, a cream, a solid, a film, an emulsion, a suspension, a solution, an aerosol (e.g., a liquid formulation) or any combination of the aforesaid.

In some embodiments, a contemplated liquid medicament features a pharmaceutically acceptable liquid formulation including about 4% to about 8% (e.g., about 6%) by weight levodopa, about 0.1% to about 1.5% (e.g., about 0.6% to about 1.4%, about 0.75%, or about 1.4%) by weight carbidopa, about 10% to about 20% (e.g., about 15% to about 16%, about 15.2%, or about 15.6%) by weight arginine, and about 0.1% to about 1.5% (e.g., about 0.4% to about 1%, about 0.4% to about 0.6%, or about 0.5%) by weight ascorbic acid or a salt thereof, In such embodiments the formulation, after 1 day at 25° C., after 30 days at 25° C., or after 180 days at 25° C., has less than about 1.0, less than about 0.75 µg/ml, less than about 0.5 µg/ml, less than about 0.2 µg/ml, less than about 0.1 µg/ml, or less than about 0.05 µg/ml hydrazine, as determined by GCMS. The formulation may further include about 0.1% to about 0.7% (e.g., about 0.4% or about 0.5%) by weight of L-cysteine or NAC. In a particular embodiment, the formulation includes (a) about 0.4% to about 0.6%, or about 0.4 to about 1% by weight ascorbic acid or a salt thereof; and (b) about 0.1% to about 0.7% by weight of L-cysteine or NAC. In this aspect, the formulation may further include about 0.1% to about 0.5% (e.g., about 0.3%) by weight Tween-80.

In some embodiments, a liquid medicament features a pharmaceutically acceptable liquid formulation including: about 8% to about 16% (e.g., about 12% to about 15%, about 12%, or about 13.2%) by weight levodopa; about 1% to about 4% (e.g., about 3.0% or about 3.3%) by weight carbidopa; about 20% to about 42% (e.g., about 32% to about 42%, about 32%, or about 36%) by weight of a component selected from the group consisting of arginine, or meglumine, or a combination thereof; about 0.1% to about 1.5% (e.g., about 1.0% to about 1.4%, about 1.2%, or about 1.3%) by weight ascorbic acid or a salt thereof (e.g., sodium ascorbate), e.g., where the formulation, after 1, 2, 3, 4, 6, 8, 10, 12, 15, 18, 20, or 24 hours; 1, 2, 3, 5, 7, 10, 14, 21, 28, or 30 days; 1, 2, 3, 4, 6, 9, or 12 months; or 1, 1.5, 2, 2.5, or 3 years at 25° C., has less than about 1.0, less than about 0.75 µg/ml, less than about 0.5 µg/ml, less than about 0.2

µg/ml, less than about 0.1 µg/ml, or less than about 0.05 µg/ml hydrazine as determined by GCMS. The formulation may further include about 0.1% to about 1% (e.g., about 0.1% to about 0.5%, about 0.3%, or about 0.5%) of L-cysteine or salt thereof (e.g., cysteine HCl) or NAC. In a particular embodiment, the formulation includes about 0.1% to about 0.5% of L-cysteine or NAC, and about 1.0 to about 1.4% by weight ascorbic acid or a salt thereof, or any combination of the aforesaid.

In certain embodiments, a liquid medicament can include about 0.1% to about 10% carbidopa, e.g., about 0.5% to about 8%, about 0.6% to about 5%, about 0.1% to about 1%, about 1% to about 2%, particularly about 0.75%, about 1.4%, or about 4% carbidopa. For example, a disclosed formulation can include about 1% to about 3% by weight, about 2.5% to about 3.5% by weight, about 0.6% to about 4% by weight, or about 1.2% to about 4% by weight carbidopa. In certain embodiments, disclosed compositions include about 0.01% to about 6% by weight carbidopa, about 0.1% to about 6% by weight carbidopa, or about 1% about to about 4% by weight carbidopa, e.g., about 0.6% to about 4% or about 1.2% to about 3% or about 4% by weight carbidopa.

In certain embodiments, the formulation can include arginine, and/or meglumine, or a salt thereof or any combination thereof. For example, a disclosed formulation can include about 0.1% to about 42%, e.g., about 1% to about 10%, about 12% to about 18%, about 0.1% to about 40%, about 2% to about 7%, about 3.2% to about 3.4%, about 3.6%, about 3.7%, or about 4.6% arginine and/or meglumine, or a salt thereof or any combination thereof. In other embodiments, disclosed formulations include about 10% to about 20%, about 10% to about 25%, about 12% to about 18%, about 12.8%, about 14.8%, about 15.2%, about 15.5%, or about 18.5% arginine and/or meglumine or a salt thereof or any combination thereof. In certain embodiments, arginine, meglumine, a salt thereof, or any combination thereof are present at about 25% to about 40%, about 30% to about 38%, about 32% or about 36%.

The formulations can include levodopa. For example, in certain embodiments the formulation includes about 1% to about 20% levodopa, e.g., about 2% to about 8%, about 4% to about 7%, about 5%, or about 6% levodopa. In other embodiments, the formulations include about 8% to about 20%, about 8% to about 16%, about 10% to about 14%, about 11% to about 14%, about 12%, or about 13.2% levodopa. A disclosed formulation can have a molar ratio of carbidopa to arginine (or meglumine) of about 1:1 to about 1:25 or of about 1:1 to about 1:35.

The formulations can include one, two, or more antioxidants or o-quinone scavenger agents. For example, a disclosed formulation can include one, two, or more of an agent each independently selected from the group consisting of ascorbic acid, a salt thereof (e.g., sodium ascorbate, calcium ascorbate, potassium ascorbate, ascorbyl palmitate, or ascorbyl stearate, particularly sodium ascorbate), cysteine or a cysteine derivative (e.g., L-cysteine, Nacetylcysteine (NAC), glutathione, diacetylcystine, S-methyl-N-acetylcysteine amide, an acetyl derivative of S-methyl-N-acetylcysteine methylhydrazide, S-methylcysteine morpholineamide, Smethyl-N-acetylcysteine morpholineamide, or a salt thereof), or any suitable combination thereof. For example, a disclosed formulation can include ascorbic acid or a salt thereof, and a cysteine derivative, such as NAC.

The formulations can include other antioxidants, such as di-tert-butyl methyl phenols, tert-butyl-methoxyphenols, polyphenols, tocopherols, and ubiquinones (e.g., caffeic acid).

The formulations can also include a tyrosinase inhibitor. Exemplary tyrosinase inhibitors include captopril, methimazole, quercetin, arbutin, aloesin, N-acetylglucoseamine, retinoic acid, atocopheryl ferulate, MAP (Mg ascorbyl phosphate), substrate analogues (e.g., sodium benzoate, Lphenylalanine), and $Cu^{++}$ chelators (for example, $Na_2$-EDTA, $Na_2$-EDTA-Ca, DMSA (succimer), DPA (D-penicillamine), trientine-HCl, dimercaprol, clioquinol, sodium thiosulfate, TETA, TEPA, curcumin, neocuproine, tannin, and cuprizone).

The formulations can include ascorbic acid or a salt thereof (e.g., sodium ascorbate). For example, disclosed formulations can include 0.1% to about 10% or more ascorbic acid (or a salt thereof), or about 0.1% to about 2%, e.g., about 0.2% to about 1.5%, about 0.2% to about 2.0%, about 0.2% to about 2.5%, about 0.3% to about 1.2%, e.g., about 0.4%, about 0.5%, about 0.75%, about 0.85%, or about 1.0% by weight ascorbic acid. For example, a disclosed formulation can include about 0.8% to about 1.3% or about 1% to about 2.5% by weight ascorbic acid or a salt thereof. In a particular embodiment, a disclosed formulation can include about 0.5% to about 0.85%, or, e.g., about 0.5%, about 0.75%, about 0.85%, about 1.0%, about 1.2%, or about 1.3% by weight sodium ascorbate or ascorbic acid.

In particular embodiments, the formulations can include a bisulfite, e.g., sodium bisulfite or one or more other sulfite salts, e.g., sodium hydrogen sulfite or sodium metabisulfite. In some embodiments, the formulations can include for example, NAC, L-cysteine, diacetylcystine, and/or glutathione. In particular embodiments, the formulations include about 0.001% to about 5%, about 0.01% to about 5%, about 0.1% to about 5%, about 0.001% to about 1%, about 0.01% to about 1%, or about 0.1% to about 1% by weight of each of NAC, L-cysteine, diacetylcystine, and/or glutathione. For example, a disclosed formulation can include about 0.01% to about 5%, e.g., about 0.05% to about 1%, about 0.1% to about 0.6%, about 0.1%, about 0.2%, about 0.3%, about 0.4%, or about 0.5% of NAC and/or L-cysteine. In a particular embodiment, a disclosed formulation includes about 0.4% or about 0.5% NAC. In another particular embodiment, a disclosed formulation includes about 0.3%, about 0.4%, or about 0.5% L-cysteine.

For example, a formulation can include ascorbic acid (or a salt thereof) and a cysteine derivative, e.g., L-cysteine and/or NAC. In an exemplary embodiment, a disclosed formulation includes about 0.1% to about 10% ascorbic acid (or a salt thereof) and about 0.001% to about 5% or about 0.001% to about 1% by weight of each of L-cysteine and/or NAC and/or diacetylcystine and/or glutathione. In particular embodiments, the composition includes ascorbic acid and Lcysteine, sodium ascorbate and NAC, ascorbic acid and NAC, sodium ascorbate and L-cysteine, ascorbic acid and diacetylcystine, sodium ascorbate and diacetylcystine, ascorbic acid and glutathione, or sodium ascorbate and glutathione.

Contemplated formulations are liquid, and can include a surfactant. For example, polysorbate 20, 40, 60, or 80 may be present in a disclosed formulation at, e.g., about 0.01% to about 5%, about 0.1% to about 0.5%, e.g., about 0.3% polysorbate 20, 40, 60, and/or 80. In particular embodiments, polysorbate 80 is present at about 0.3%.

Such formulations or solutions can have a pH that is pharmaceutically acceptable for subcutaneous administration, e.g., a pH of about 8 to about 10, for example, about 9.1 to about 9.8, e.g., 9.2 to 9.6, at 25° C.

In particular embodiments, a liquid medicament is one of those in Tables 1 and 2.

TABLE 1

| DS (%) | LD | CD | Arginine | Ascorbic Acid | L-Cysteine | NAC | Tween-80 | pH |
|---|---|---|---|---|---|---|---|---|
| 1 | 6 | 1.4 | 15.5 | 0.5 | 0.4 | — | 0.3 | 9.4-9.6 |
| 2 | 6 | 1.4 | 15.5 | 0.5 | — | 0.5 | 0.3 | 9.4-9.6 |
| 3 | 6 | 0.75 | 15.2 | 0.5 | 0.4 | — | 0.3 | 9.4-9.6 |
| 4 | 6 | 0.75 | 15.2 | 0.5 | — | 0.5 | 0.3 | 9.4-9.6 |
| Margins | 6 | 0.6-1.4 | 15-16 | 0.5 | 0.4 | 0.5 | 0.3 | 9.4-9.6 |

TABLE 2

| DS (%) | LD | CD | Arginine | Meglumine | Sodium Ascorbate | L-Cysteine | NAC | Cysteine-HCl | Tween-80 | pH |
|---|---|---|---|---|---|---|---|---|---|---|
| 1 | 12 | 3 | 32 | — | 1.2 | 0.3 | — | — | — | 9.6-9.8 |
| 2 | 13.2 | 3.3 | 36 | — | 1.3 | 0.3 | — | — | — | 9.6-9.8 |
| 3 | 13.2 | 3.3 | — | 36 | 1.3 | 0.3 | — | — | — | 9.6-9.8 |
| 4 | 12 | 3 | — | 32 | 1.2 | — | 0.3 | — | — | 9.6-9.8 |
| 5 | 12 | 3 | 32 | — | 1.2 | — | 0.3 | — | — | 9.6-9.8 |
|  | 12-15 | 1.2-4 | 32-42 | 32-42 | 1.0-1.3 |  | 0.1-0.5 | * | ≤2 ** | 9.6-9.8 |

\* Can replace L-cysteine.
\*\* Optionally added to stabilize the formulation

In other embodiments, the fluid medicament may include apomorphine and an organic acid or an amino acid. As used herein, the term "organic acid" refers to an organic compound with acidic properties such as carboxylic acids, dicarboxylic acids, sulfonic acids, alcohols, hydroxy acids, thiols, and thio-acids. For example, the organic acids for use in the formulation may contain at least two, at least three, or at least four carbon atoms, e.g., tartaric acid. Examples of organic acids include, but are not limited to, amino acids such as aspartic acid, glutamic acid, and arginine, and dicarboxylic acids such as fumaric acid, oxalic acid, malonic acid, succinic acid, glutaric acid, maleic acid, and the like. Further examples of organic acids include lactic acid, malic acid, aconitic acid, citric acid, alycolic acid, ascorbic acid, formic acid, acetic acid, tartaric acid, and glucuronic acid. Exemplary organic acids include, but are not limited to, amino acids, carboxylic acids, and dicarboxylic acids. For example, contemplated carboxylic acids and/or dicarboxylic acids for use in the composition may contain at least two, at least three, or at least four carbon atoms, e.g., tartaric acid. Contemplated dicarboxylic acids for use in the claimed formulations may be hydrophilic or substituted with hydrophilic groups, e.g., hydroxyl groups. Contemplated amino acids for use in the claimed formulations may be, without limiting, acidic natural amino acids such as aspartic acid or glutamic acid, or acidic unnatural amino acids such as cysteic acid. The term "natural amino acid" refers to any of the amino acids found in proteins. Examples of natural amino acids include, but are not limited to, alanine, arginine, aspartic acid, glutamic acid, histidine, lysine, and the like. The term "non-natural amino acid" refers to non-proteinogenic amino acids that either occur naturally or are chemically synthesized. Examples of non-natural amino acids include, but are not limited to, ornithine, β-alanine, 2-aminoadipic acid, 3-aminoadipic acid, γ-carboxyglutamic acid, hydroxylysine, 4-guanidinobutyric acid, 3-guanidinopropionic acid, 4-azidobutanoic acid, 5azidopentanoic acid, and the like. Both D- and L-amino acids are contemplated herein.

In certain embodiments, the liquid medicament further comprises a local anaesthetic, i.e., a drug which causes a reversible loss of sensation for a limited region of the body while maintaining consciousness, and/or an anti-inflammatory agent. Examples of local anaesthetics include, without limitation, amide based local anaesthetics such as lidocaine, prilocaine, bupivicaine, levobupivacaine, ropivacaine, mepivacaine, dibucaine, and etidocine, and ester based local anaesthetics such as procaine, amethocaine, cocaine, benzocaine, and tetracaine. Examples of anti-inflammatory agents include, without limitation, non-steroidal anti-inflammatory agents such as diclofenac, ketorolac, salicylates ibuprofen, piroxicam, and benzydamine, and steroidal anti-inflammatory agents such as prednisone, dexmethasone, betamethasone, prednisone hydrocortisone, and salts thereof.

The pharmaceutical composition may be a liquid solution, i.e., a substantially homogeneous liquid mixture at room temperature, e.g., at 25° C., or a semisolid solution formulated, e.g., as a gel, a gum, or a candy. Such liquid or semi-solid mixtures may comprise water and/or other pharmaceutically acceptable carriers and/or excipients. In a particular embodiment, the disclosed composition is substantially aqueous.

Each numerical value presented herein is contemplated to represent a minimum value or a maximum value in a range for a corresponding parameter. Accordingly, when added to the claims, the numerical value provides express support for claiming the range, which may lie above or below the numerical value, in accordance with the teachings herein. Every value between the minimum value and the maximum value within each numerical range presented herein (including in the chart shown in FIG. 33), is contemplated and expressly supported herein, subject to the number of significant digits expressed in each particular range.

As already briefly mentioned herein, the device may include a first fluid sensor for sensing one or more characteristics of the fluid medicament. The one or more characteristics may be monitored continuously. Such characteristics can include, for example, a chemical characteristic, an optical characteristic, a biological characteristic, and/or a physical characteristic.

Non-limiting examples of chemical characteristics may include an analyte concentration (e.g., concentration of an active pharmaceutical ingredient (API) such as carbidopa, levodopa and/or apomorphine), a distribution of the API in the fluid medicament, an aggregate condition of the API and/or the fluid medicament, a map of aggregate conditions of the API and/or the fluid medicament, and/or pH value.

Non-limiting examples of physical characteristics may include mass, volume, electrical conductivity, temperature, density, color, reflectance, transmissivity, viscosity, type of fluid, and/or thermal conductivity. Physical characteristics may optionally be measured to determine if the fluid medicament received in the reservoir contains bubbles.

In some embodiments, the fluid sensor may comprise an optical sensor operable to measure a characteristic of and/or related to the fluid. Characteristics pertaining to fluid contained in the reservoir may be measured using methods that are based on continuous, discrete, transmissive and/or reflective measuring techniques.

The optical sensor may measure or determine a characteristic of the fluid based on one or more characteristics of light detected by one or more light detectors of the fluid sensor. Such characteristic of light can pertain, for example, to the light's wavelength, amplitude, polarization, a phase difference, or any combination of the aforesaid. Detection of light may comprise transmission- and/or reflection-based methods.

Optionally, a liquid quantity in the reservoir 106 may be determined based on a liquid level and/or volume in the reservoir 106. The fluid sensor may be operable to continuously or discretely measure the quantity of a fluid in the reservoir.

Figure 34A:
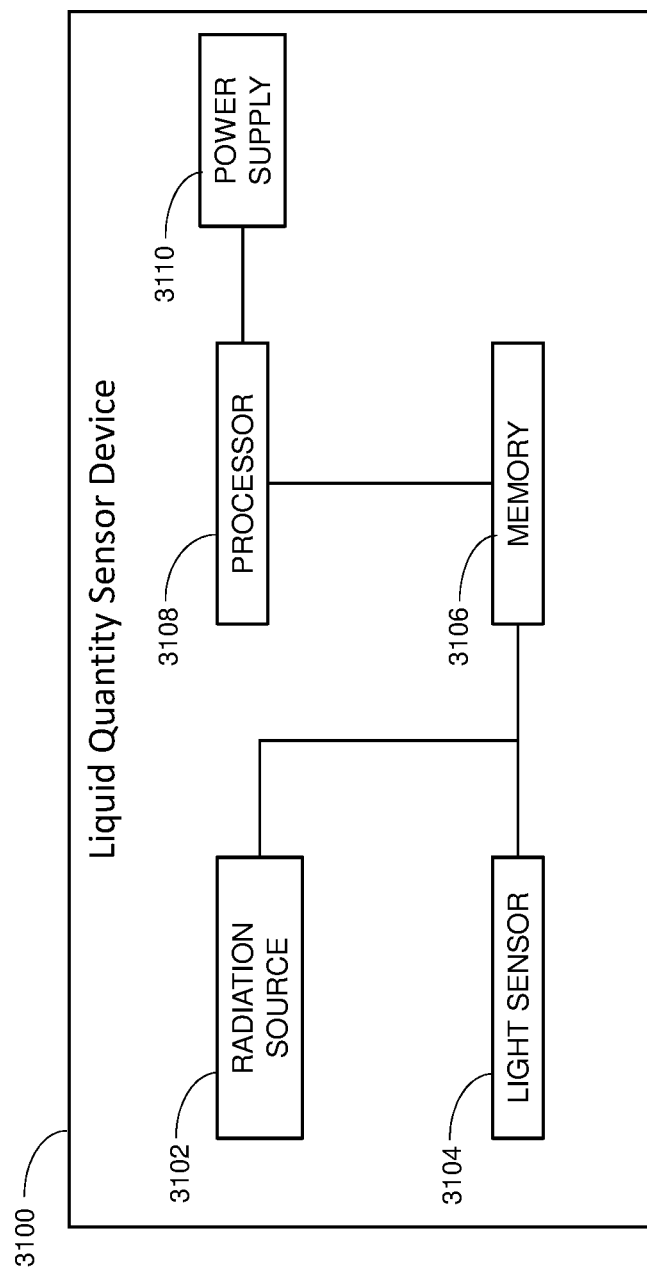
FIG. 34A is a schematic block diagram illustration of a liquid quantity sensor device, according to some embodiments.

Referring to FIG. 34A, a fluid sensor may for example include a liquid quantity sensor device 3100. Liquid quantity sensor device 3100 may include a radiation source 3102 (e.g., an emitter) operable to emit light, a detector 3104 operable to sense light, a memory 3106, a processor 3108 and a power module 3110 (e.g., a power source such as a battery) for powering the various components of liquid quantity sensor device 3100.

In some embodiments, liquid quantity sensor device 3100 may be operable to continuously or discretely measure the quantity of a fluid in the reservoir. Optionally, liquid quantity measurement may be transmission-based, reflection-based, or both. Optionally, liquid quantity in the reservoir may be determined based on a liquid level and/or volume in the reservoir. In some embodiments the measurement of the drug volume inside the reservoir may be measured by determining the time-of-flight (TOF) of emitted light inside the drug reservoir and/or by measuring attenuation of light that propagated through the reservoir 106.

The arrangements referred to herein below with respect to FIGS. 34B to 34G may be considered to enable a method of continuous measurement of liquid quantity in the reservoir 106, based on one or more characteristics of light detected by the one or more detectors of the arrangement(s).

Figure 34C:
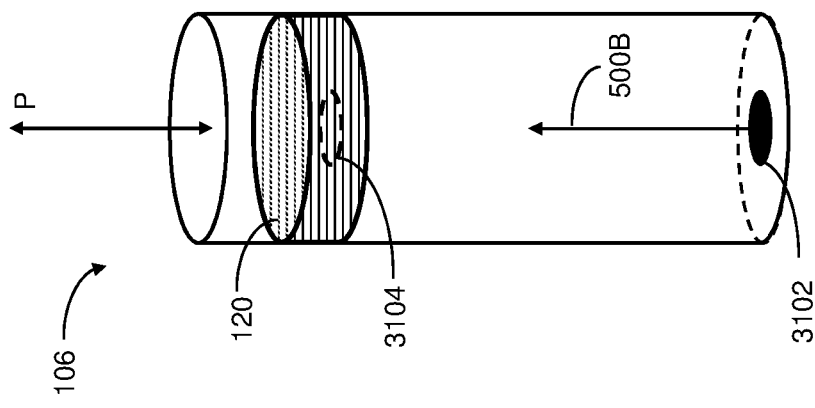
Figure 34B:
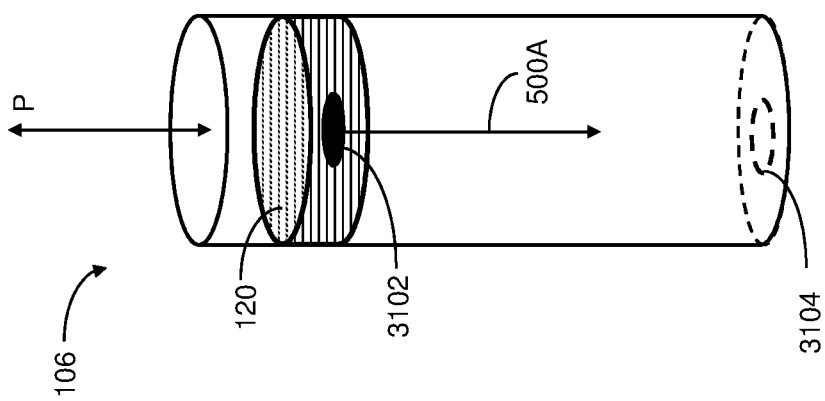

Referring to FIG. 34B, the radiation source 3102 may in some embodiment be arranged on the underside of or embedded in the plunger head 120, and the detector 3104 may be arranged opposite the radiation source 3102 such that light 500A emitted by the radiation source 3102 propagates from the plunger head 120 towards a distal end of the reservoir 106 comprising detector 3104 arranged to detect light 500A. The example shown in FIG. 34B schematically illustrates a method for measuring liquid quantity that is light transmissive-based. Displacement direction of the plunger 120 from a proximal to a distal end of the reservoir 106 (or vice versa) is herein schematically illustrated by double-headed arrow P.

Referring now to FIG. 34C, the radiation source 3102 may be in some embodiments arranged on the distal end of the reservoir 106 and the detector 3104 may be arranged on the underside of or embedded in the plunger head 120 such that light 500A emitted by the radiation source 3102 propagates from the distal end of the reservoir 106 towards the plunger head 120 comprising detector 3104 arranged to detect reflected light 500B. The example shown in FIG. 34C schematically illustrates, in analogy to FIG. 34B, a method for measuring liquid quantity that is light transmissive-based.

Referring to FIG. 34D, both the radiation source 3102 and the detector 3104 may in some embodiments be arranged on the underside of or embedded in plunger head 120, such that reflected light 500B which is generated in response to radiating light 500A from the plunger head 120 into the distal end of the reservoir 106 are detectable by the detector 3104. The arrangement shown in FIG. 34D shows an example reflection-based method for measuring liquid quantity.

Further referring to FIG. 34E, the reservoir 106 may additionally include a second detector 3105 arranged on the distal end of the reservoir 106 and which is operable to detect light 500A emitted by the radiation source 3102 towards the distal end of the reservoir 106. The arrangement shown in FIG. 34E shows an example reflection- and transmissive-based method for measuring a quantity of liquid contained in the reservoir 106.

Referring now to FIGS. 34F and 34G, the arrangement shown in FIGS. 34D and 34E may be reversed. As schematically illustrated in FIG. 34F, the radiation source 3102 and the first detector 3104 may in some embodiments be arranged at the distal end of the reservoir 106 such that reflections 500B produced in response to radiating light 500A from the distal end towards plunger head 120 are detectable by the detector 3104. The arrangement shown in FIG. 34F thus shows a reflection-based method for measuring a quantity of liquid contained in the reservoir 106.

The arrangement shown in FIG. 34G may additionally include the second detector 3105 arranged on the underside of or embedded in the plunger head 120 such that light 500A radiated from the distal end of reservoir 106 towards the plunger head 120 is detectable by the second detector 3105.

The arrangement shown in FIG. 34G thus show examples of both a reflection- and transmissive-based method for measuring a quantity of liquid contained in the reservoir 106.

In some embodiments the radiation source and the detector presented in FIGS. 34D-34F are arranged to be at identical positions. In some embodiments, a plurality of radiation sources may be arranged circumferential to a detector, or vice versa.

As already indicated herein, the arrangements schematically shown in FIGS. 34B to 34G may be considered to enable a method of continuous measurement of liquid quantity in the reservoir 106, based on one or more characteristics of light detected by the one or more detectors of the arrangement(s).

The arrangements referred to herein below with respect to FIGS. 34H to 34I may be considered to implement methods for discretely measuring a quantity of liquid contained in the reservoir 106. For example, a plurality of radiation sources 3112 may be arranged on a cylindrical shell or curved body of the reservoir 106 in a row extending from the reservoir's bottom to top at different heights $h_i$ of the reservoir 106. The reservoir 106 may further include a plurality of detectors 3114 that are arranged on the cylindrical shell body of the reservoir 106 such to be able to detect light emitted by each one of the plurality of radiation sources 3112. For instance, the plurality of detectors 3114 may be arranged opposite the plurality of radiation sources 3112 in a row extending from the reservoir's bottom to top, facing the light sources 3112.

Each one of light sources 3112 may emit a plurality of light rays 500C from different positions $h_i$ along the reservoir 106. A light ray 500Ci propagates across reservoir 106 in a direction that may be substantially perpendicular to the longitudinal axis 137 of the plunger head 120 and is incident onto the corresponding detector 3114*i*. In response to detecting light 500C that is incident onto the detectors 3114, the detectors 3114 may generate an output which relates to a characteristic of the detected light ray. Such characteristic can pertain to a change in intensity of the light ray 500Ci propagating through the reservoir 106 and/or to a time-of-flight. The arrangement shown in FIG. 34H may for example allow generating a height-dependent function of a characteristic of fluid contained in the reservoir 106. For example, density, color, transmissivity, and/or the like, may be measured as a function of the height relative to a level of fluid contained in the reservoir 106. In some embodiments, a plurality of light sources 3112 and/or a plurality of detectors 3114 may be employed at a corresponding height h1 above the bottom of the reservoir 106.

As shown in FIG. 34H, the arrangement shown in FIG. 34I may additionally include the light source 3102 and the second detector 3105 arranged, for example, on the underside of the plunger 120, and the first detector 3104 arranged on the distal end of the reservoir 106. The light sources and detectors shown in FIG. 34I may thus allow radiating light lengthwise and/or radial into the reservoir 106. Additional or alternative arrangements may be employed for radiating light lengthwise and/or radially into reservoir 106. Optionally, light may be selectively (e.g., alternatingly) radiated in lengthwise and radial direction into reservoir 106. For example, during time-period t1, light 500A may be radiated lengthwise into reservoir 106, and during a consecutive time-period t2, light 500C may be radiated transversely into the reservoir 106, and so forth.

Further reference is made to FIG. 34J. In some embodiments, a matrix of light sources 3102 may be arranged on one side of the reservoir 106 and a matrix of detectors 3104 may be arranged opposite the matrix of light sources 3102. In this manner, light and, correspondingly, liquid characteristics may be mapped radially, across the reservoir 106, as schematically illustrated by arrow R, for example, to determine a value relating to homogeneity and/or inhomogeneity of fluid contained in the reservoir 106.

Figure 35:
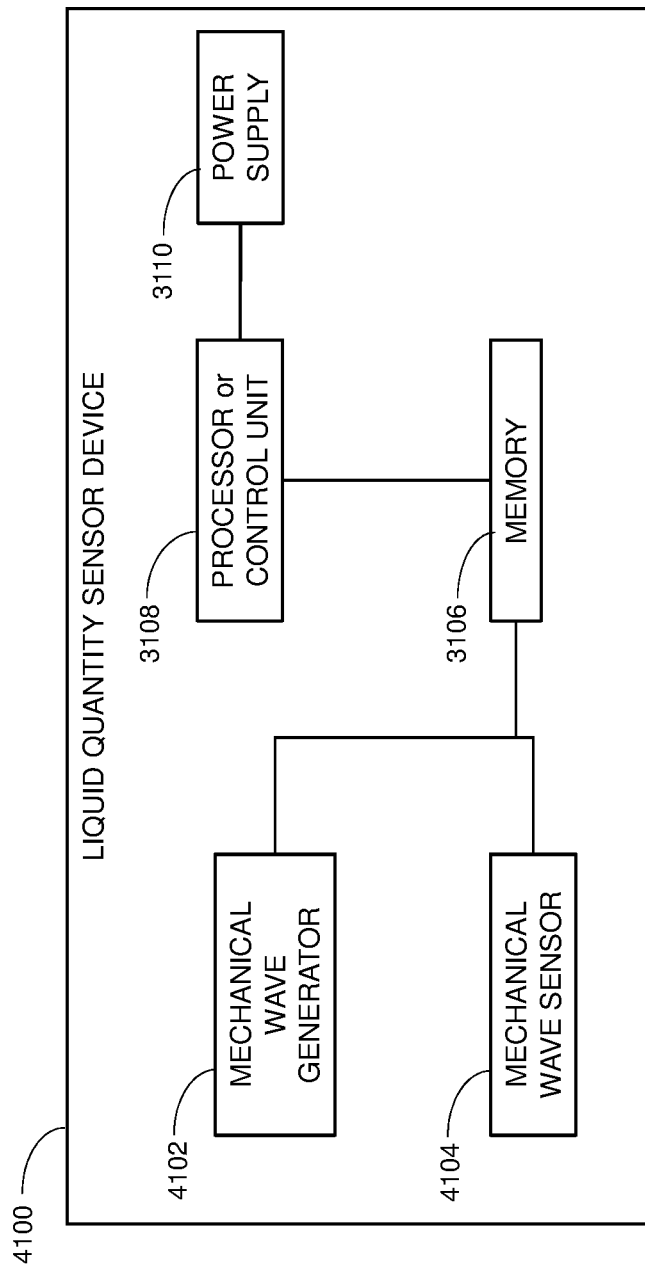
FIG. 35 is a schematic block diagram illustration of a liquid quantity sensor device, according to alternative embodiments.

According to some embodiments, a liquid quantity sensor device 4100 may be operable to determine a quantity of liquid in the reservoir 106 based on the measurement characteristics of pressure waves propagating through the liquid. FIG. 35 is a block diagram illustrating a liquid quantity sensor device. The liquid quantity sensor device 4100 may, for example, include a mechanical wave generator (e.g., a transducer) 4102 and a mechanical wave sensor 4104 that is operable to measure characteristics of mechanical waves produced by transducer 4102. For example, the transducer 4102 may include an ultrasound transducer, and the mechanical wave sensor 4104 may include an ultrasound sensor. In some embodiments, the same sensing element may be employed by the transducer 4102 and the mechanical wave sensor 4104. Optionally, micro-electromechanical and/or piezoelectric transducers may be employed to generate pressure waves in liquid contained in the reservoir 106, e.g., for determining a value relating to a characteristic of the liquid such as temperature, transparency, cloudiness, viscosity, and/or the like. For example, a less transparent liquid may be indicative of an increased level of crystallization. In the event a measured characteristic indicates that the fluid's level of transparency is below a low threshold level, delivery of the fluid medicament may be stopped. Optionally, the fluid may be stirred for a predetermined time period. Optionally, the fluid may be stirred until the level of fluid transparency exceeds a high transparency threshold level.

In some embodiments the reservoir may include an automatic steering element that will operate according to a pre-programed timing and/or according to the level of liquid transparency.

In some embodiments, the device 100 may include a position tracker (e.g., a position encoder 600), e.g., for determining the position (e.g., penetration length), of the plunger 120 relative to the distal end and/or proximal end of reservoir 106 to derive, for example, the amount of fluid that is contained in the reservoir 106. The number of revolutions can be counted by the encoder 600 in either rotation direction. The most proximal or distal position of the plunger 120 in the reservoir 106 may be a reference starting or endpoint for counting the number of revolutions of, e.g., the load gear 136, to determine a penetration distance of the plunger head 120.

In some embodiments, the plunger head 120 may comprise a contact sensor (not shown) on its under and/or upper surface to allow determining when the plunger head 120 engages or makes contact with the bottom or the upper surface of the reservoir 106.

Figure 36:
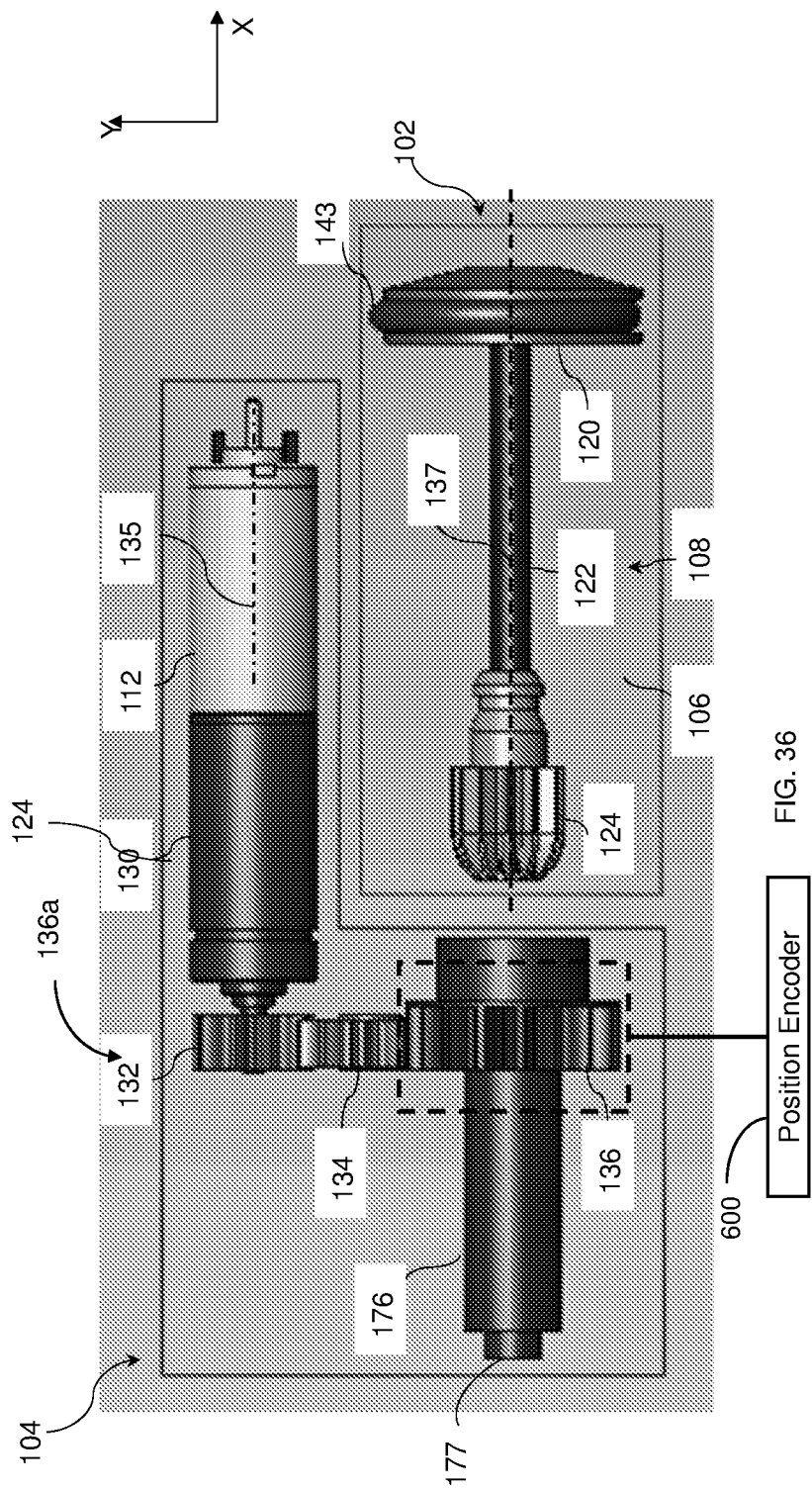
FIG. 36 is a schematic side view illustration of a disposable/reusable part operably coupled with a position encoder, according to some embodiments.

With reference to FIG. 36, a position tracker is schematically designated by reference numeral "600" and schematically illustrated as being operably coupled, for example, with the load gear 136, e.g., for providing a load gear position output that is indicative of a rotational position of the load gear 136. The load gear 136 can be operably engaged with the nut 124. A rotational position of the nut 124 can be determined based on the rotational position of load gear 136. The rotational position of the nut 124 can be associated with a translational position of the plunger head 120 within the reservoir 106. As a result, the load gear position output provided by the position tracker 600 can be used for determining a translational position of the plunger head 120. Based on the translational position of plunger head 120, the quantity of fluid contained in reservoir 134 can be determined, e.g., by the computing unit 117.

In some embodiments, the device 100 may employ a sensor (not shown) for sensing an angular orientation of the plunger head 120 relative to the reservoir 106.

With reference to FIG. 37A, a sensor 3700 may be employed for determining a liquid quantity in the reservoir 106 by measuring a change in an electrical characteristic of the sensor 3700. The sensor 3700 may be arranged internal to and extend longitudinally along the reservoir 106, parallel to the longitudinal axis thereof, so that the sensor 3700 can make direct contact with a fluid contained in the reservoir 106. A measurable electrical characteristic of the sensor 3700 may change depending on the amount overlap between the sensor and the fluid and, optionally, based on a characteristic of the fluid. Such electrical characteristic can pertain, for example, to the capacitance and/or electrical impedance. For example, a measured capacitance of the sensor 3700 may increase as a function of an increase of a level of fluid in the reservoir 106. In another example, the capacitance of the sensor 3700 may decrease as a function of an increase in the level of fluid of the reservoir 106. In some embodiments, a portion of the sensor 3700 may protrude or extend beyond the reservoir 106 or be otherwise arranged such that said portion does not come into operational sensing engagement with the fluid. Accordingly, a sensing output of said fluid portion may not be influenced by the amount of fluid contained in reservoir. The output provided by the protruding portion may thus serve as a reference for determining an amount of fluid contained in the fluid reservoir 106.

Referring now to FIGS. 37B to 37F, a capacitor sensor 3800 may be coupled with (e.g., glued and/or otherwise fastened) a leg portion 145 of the reusable part 104 such that when the disposable part 102 and the reusable part 104 are operably coupled with each other, the sensors 3800a and 3800b are positioned opposite and/or facing reservoirs 106a and 106b such to provide an output related to the quantity of fluid stored in the reservoirs 106a and 106b. Although the discussion concerning the capacitance-based fluid quantity measurement is exemplified with respect to the device employing a double-piston arrangement, this should by no means be construed in a limiting manner.

Considering the double-piston arrangement, the reusable part may have a generally T-shaped configuration, of which leg portion 145 may comprise magnet 140 (see FIGS. 7B-C) and the sensors 3800a and 3800b, as schematically shown in FIG. 37C. The reusable part 104 of the single-piston arrangement may be considered to have a generally L-shaped configuration, of which the leg portion 145 may comprise the sensor 3800.

As shown in FIGS. 37C and 37D, the sensor 3800 may be bendable. A sensor such as sensor 3800 shown herein may be implemented by a flexible printed circuit board (FPCB). Optionally, the leg portion 145 may be curved inwardly or have a concave shape, in order to conformably abut against the rounded surface of a reservoir 106. Accordingly, the sensor 3800 may attain a bent shape when fastened onto the leg portion 145 of for example the reusable part 104 of a single- or double-piston arrangement.

Figures 37E, 37F:
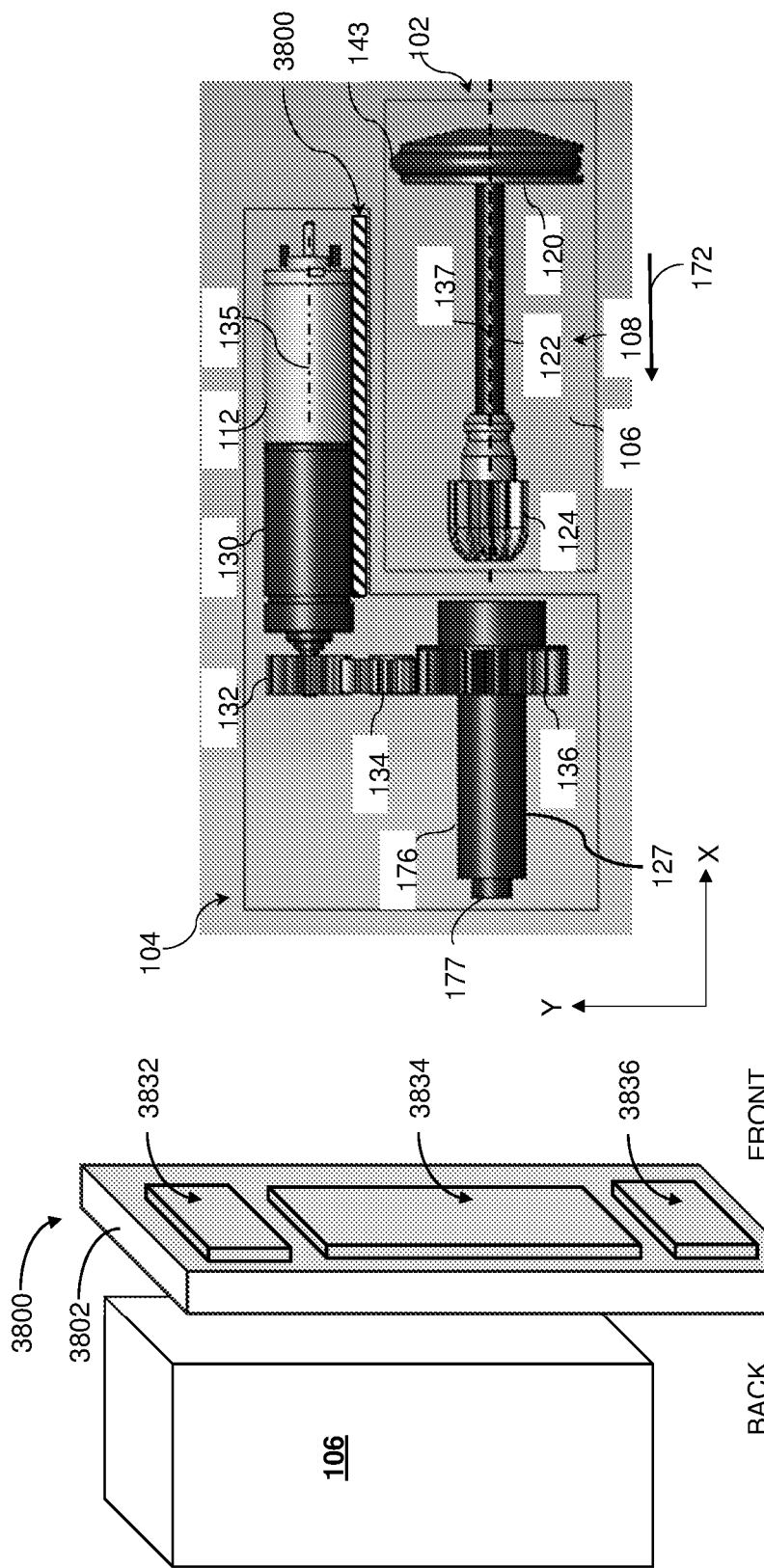
FIG. 37E schematically shows a 3D view of the positional relationship between and a reservoir and a capacitor-based liquid quantity sensor configured to measure a liquid quantity in the reservoir, according to some embodiments.
FIG. 37F schematically shows the disposable part when operably coupled with the reusable part and the resulting positional relationship between the capacitance-based liquid quantity sensor of the reusable part and the reservoir of the disposable part.

Further reference is made to FIG. 37E, which schematically shows a 3D view illustration of the positional relationship between a reservoir 106 and a capacitor-based liquid quantity sensor 3800 configured to measure a liquid quantity in the reservoir 106, according to some embodiments; and further to FIG. 37F which schematically shows a disposable part 102 of the device 100 when operably coupled with a reusable part 104 of the device, and the resulting positional relationship between the capacitance-based liquid quantity sensor 3800 of the reusable part and the reservoir of the disposable part. As exemplified in FIG. 37F, the capacitance-based liquid quantity sensor 3800 is external to the reservoir 106 and part of the reusable part 104.

Additional reference is made to FIG. 37G, which schematically shows front and back view illustrations of a capacitance-based liquid quantity sensor 3800, according to some embodiments. A capacitance-based fluid measurement sensor 3800 may be configured to provide sensing outputs without requiring the sensor to directly engage with the fluid. In other words, sensor 3800 may be a non-contact fluid quantity sensor.

The sensor 3800 may comprise a substrate 3802 having arranged thereon a front inlet electrode 3812, a front outlet electrode 3814 and a front reference electrode 3816. The front outlet electrode 3814 can be arranged between the front inlet electrode 3812 and the front reference electrode 3816. Analogously, the sensor 3800 can further comprise a back inlet electrode 3822, a back outlet electrode 3824 and a back reference electrode 3826. The back outlet electrode 3824 is arranged between the back inlet electrode 3812 and the back reference electrode 3816. The front and back inlet electrodes 3812 and 3822 may be arranged opposite each other to form a reference liquid capacitor ($C_{RL}$) 3832; the front and back level electrodes 3814 and 3824 may be arranged to form an level capacitor ($C_{level}$) 3834. Moreover, the front and back reference electrode 3816 and 3826 may be arranged to form an environmental capacitor sensor, which may provide a reference environmental capacitance output ($C_{RE}$) of an environmental sensor 3836.

In some other embodiments, as schematically illustrated in FIG. 37H, two electrodes forming a capacitor may be arranged side-by-side or juxtaposed on the same surface of substrate material 3802 and shielded from one another by a shielding material 3830. The positional terms "front" and "back" designating the different electrodes may in some cases be replaced by the terms "left" and "right", respectively. The electrodes may be electronically coupled with each other in a variety of configurations.

Positional terms such as "upper", "lower" "right", "left", "bottom", "below", "lowered", "low", "top", "above", "elevated", "high", "vertical" and "horizontal" as well as grammatical variations thereof as may be used herein do not necessarily indicate that, for example, a "bottom" component is below a "top" component, or that a component that is "below" is indeed "below" another component or that a component that is "above" is indeed "above" another component as such directions, components or both may be flipped, rotated, moved in space, placed in a diagonal orientation or position, placed horizontally or vertically, or similarly modified. Accordingly, it will be appreciated that the terms "bottom", "below", "top" and "above" may be used herein for exemplary purposes only, to illustrate the relative positioning or placement of certain components, to indicate a first and a second component or to do both.

As already shown in FIG. 37F, for example, the device may be configured such that when the disposable part 102 and the reusable part 104 are operably coupled with each other, the inlet and outlet capacitors 3832 and 3834 are facing the reservoir(s) 106, while the reference capacitor 3836 never faces any fluid that may be contained in the reservoir 106. Accordingly, the output of the reference capacitor 3836 may be substantially constant, irrespective of the type and/or amount of fluid contained in the reservoir 106. Hence, the sensor 3800 can be calibrated to measure a large variety of liquids without necessarily requiring knowledge of the liquids' characteristics. The relationship between the values output by the inlet and outlet capacitors 3832 and 3836, along with the reading obtained from the reference capacitor 3836, enables determining an amount of fluid in the reservoir 106. The processor 3108 of the device 100 may be operable to independently process signals provided by a plurality of sensors 3800 for providing separate fluid quantity outputs for each one of the plurality of reservoirs that may be employed by the same device.

Reverting to FIG. 37H, the output of the capacitance-based liquid quantity sensor 3800 may be fed into a capacitance to digital converter 148, the output of which may be provided to the control unit 116, e.g., for further processing.

A level of liquid may for example be determined based on the following equation:

$$\text{Level} = h_{RL} \frac{C_{level} - C_{level}(0)}{C_{RL} - C_{RE}} \quad (1)$$

where:
$h_{RL}$=the unit height of the reference liquid sensor (often, but not always, 1);
$C_{level}$=capacitance of the level capacitor;
$C_{level}(0)$=capacitance of the level capacitor when no liquid is present (empty);
$C_{RL}$=capacitance of the reference liquid sensor; and $C_{RE}$=capacitance o the reference environmental sensor.

In some embodiments, an electrical property of the sensor 3700 may change as a result of a change of the position of the plunger head 120.

According to some embodiments, fluid sensor(s) and/or pump-related functional outputs may be utilized for determining a functional state of the pump device 100. For example, a power output required to drive fluid out of the reservoir 106; the number of, e.g., nut rotations required for expelling a certain amount of liquid from cannula 216 (e.g., indicated by a rotary encoder output); a flow rate (e.g., measured by a fluid sensor); a pressure (e.g., measured by a fluid sensor); and/or the like, may be input to, for example, the processor 3108 for monitoring a functional state of pump device 100 and to detect, for example, clogging of a fluid path of the pump device 100 and/or to detect leakage of fluid from the pump device 100.

For example, if the processor 3108 determines that a sensor and/or pump-related functional output meets the conditions of a "clogging criterion," the processor may provide a corresponding output. Optionally, such clogging criterion may relate to a measured flow rate that drops, during a certain time period, below a low flow-rate threshold value. Optionally, such clogging criterion may relate to a pressure output that raises, for a certain time period, above a certain high-pressure threshold value. For example, if an output corresponds to a pressure of 4 bars or more during a certain time period, the clogging criterion conditions may be met. An output that is provided in case the conditions of a clogging condition is met may include, for example, an alert (e.g., visual, audible, and/or haptic); a command to stop operation of the drive component 112; and/or the like.

In some embodiments, a sensor and/or pump-related functional output may be analyzed to determine a viscosity of the fluid contained in the pump's reservoir and/or pathway. For example, the pressure required to force fluid out of the reservoir 106 for delivery to the patient may be indicative of the fluid's viscosity.

In some embodiments, the plunger assembly 108 may comprise a rotatable element (not shown) for implementing a rotational viscometer. Alternative techniques for measuring viscosity of fluid in the pump device 100 include, for example, vibrational techniques for measuring the damping of an oscillating electromechanical resonator immersed in the fluid. The fluid's temperature and/or other fluid characteristics may be taken into account for determining the fluid's viscosity.

In another example, the processor 3108 may determine that a sensor and/or a pump-related functional output meets the conditions of a "leakage criterion," so that the processor may provide a corresponding output.

Optionally, such leakage criterion may relate to a measured flow rate that raises, during a certain time-period, above a high flow-rate threshold value. Optionally, such leakage criterion may relate to a pressure drop, for a certain time period, below a low-pressure threshold value. For example, if an output corresponds to a pressure of 1 bar or less during a certain time-period, the leakage criterion condition may be met. An output that is provided in case the conditions of a leakage condition is met, may include, for example, an alert (e.g., visual, audible, and/or haptic); a command to stop operation of the drive component 112; and/or the like.

According to some embodiments, measurements of a plurality of fluid sensors may be compared with each other, for example, to determine if a characteristic of the fluid medicament undergoes changes and, if so, to what extent, from the moment the fluid medicament leaves the reservoir 106 until it arrives at the cannula 216 for delivery into the patient. The measurements may be employed, for example, to determine a change in an analyte concentration in the fluid medicament, flow rate and/or pressure within the cannula 216, and/or the like.

A measured and/or determined characteristic of the fluid medicament may be input to control unit 116 for controlling pumping operation. For example, operation of the drive component 112 may be based on such input.

Figure 38:
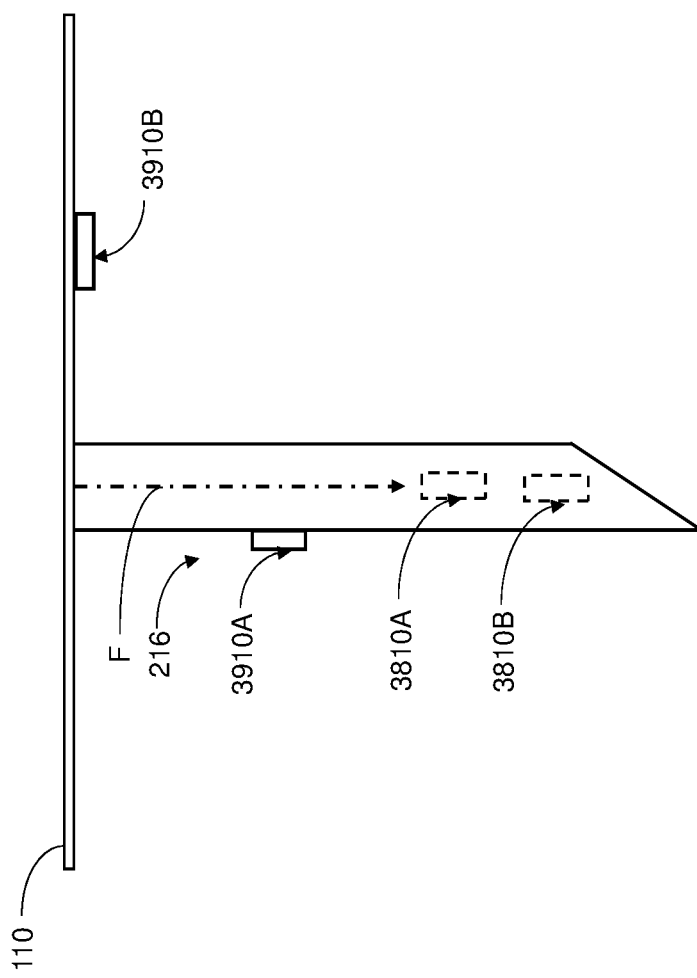
FIG. 38 schematically shows sensors that are arranged at or near the outlet of a cannula for measuring a characteristic of fluid contained in cannula, according to some embodiments.

With reference to FIG. 38, the device 100 may include one or more additional fluid sensors (e.g., fluid sensors 3810A and 3910B) that are arranged at or near the outlet of the cannula 216 for measuring a characteristic of fluid contained in the cannula 216. The additional fluid sensors 3810A and 3810B may for example be employed to determine the flow rate at which the fluid medicament is delivered to the patient.

Although sensors 3810A and 3810B are shown as being arranged in successive order with respect to a flow direction, which is schematically designated by arrow F, this should by no means be construed in a limiting manner. For instance, the sensors 3810A and 3810B may be positioned within the cannula 216 to face each other. Additional or alternative configurations may be applicable as well.

In some embodiments, data provided by the fluid sensor(s) may be descriptive of the drug volume that was delivered to the patient within a certain time period, expected remainder time for delivering a certain amount of fluid medicament to the patient (e.g., required amount, and/or remainder amount in the reservoir), and/or the like.

Figure 39:
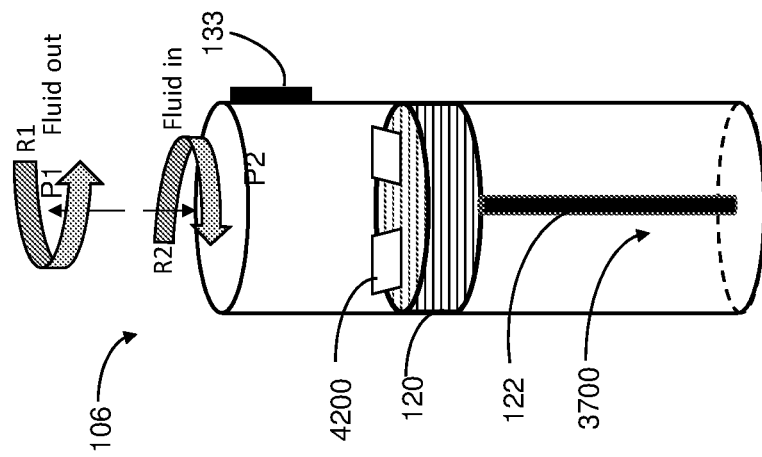
FIG. 39 schematically shows various stirring elements that are coupled with a reservoir, according to some embodiments.

According to some embodiments, the device 100 may comprise stirring elements arranged and operable to stir, actively and/or passively, the fluid medicament while stored and/or being urged to flow through a fluid path of the device 100. Stirring elements may for example comprise fins (not shown) that protrude inwardly into a cavity formed by the fluid path to change a local fluid direction of the fluid medicament. Optionally, the fins are alternatingly arranged opposite each other along the longitudinal axis of the fluid path's cavity. Optionally, the fins are arranged in a screw-like progression along the fluid path. As described above, stirring elements may be actuated if a measured characteristic indicates that the fluid's level of transparency is at or below a low-threshold level. The stirring element can have a physical element inside the reservoir or alternatively comprise a mechanism that operates on the reservoir 106 from the outside thereof, for example by using vibration and/or acoustic waves. As is shown, for example, in FIG. 39, a stirring element may comprise a vibration-inducing element 133 that is coupled with the reservoir 106.

In some embodiments, plunger assembly 108 and the drive components may be configured such that the plunger head 120 rotates during the axial translation thereof in the reservoir 106. Rotation of the plunger head 120 may be utilized to stir fluid contained in the reservoir 106. For example, the stirring element may be implemented by fins 4200 that are arranged on the distal surface portion of the plunger head 120 to extend into the part of the reservoir 106 that can contain fluid for delivery to a patient, and the fins 4200 can be arranged to stir the fluid during axial displacement of the plunger head 120. As is for example shown in FIG. 39, the plunger head 120 and the fins 4200 arranged thereon may rotate in a direction R1 during axial displacement of the plunger head 120 in a distal direction P1, and rotate in a direction R2 during axial displacement of the plunger head 120 in a proximal direction P2. The fins 4200 may optionally be integrally formed with the plunger head 120. Optionally, the fins 4200 may be coupled to the plunger head 120.

According to some embodiments, one or more physiological sensors may be operably coupled with and/or employed by the device 100 for measuring one or more physiological characteristics of the patient using the pump device 100, prior, during and/or after delivery of the fluid medicament. With reference to FIG. 38, pump device 100 may include one or more physiological sensors 3910A and 3910B. A first physiological sensor 3910A may be, for example, coupled to the cannula 216 for percutaneously sensing a subcutaneous environment of a patient, and a second physiological sensor 3910B may be, for example, coupled to the underside of patch 110. The first physiological sensor 3910A may be configured to subcutaneously measure a physiological characteristic of the patient, and the second physiological sensor 3910B may be configured to non-invasively engage a skin surface portion of the patient for measuring a physiological characteristic related to the patient. In some embodiments, a physiological sensor may be embodied by a non-inertial sensor and/or by an inertial sensor (not shown). Inertial sensors can include accelerometers and/or gyroscopes for measuring parameters related to, e.g., tremor, stiffness of a patient's gait, and/or the like. Such non-inertial sensors may thus be coupled to the patient's limb and/or torso, for measuring the patient's tremor, stiffness and/or gait. Output of the non-inertial and/or inertial sensors may be used for controlling the pump operation.

In some embodiments, imaging sensors may be employed in conjunction with the pump device 100 for imaging the patient's facial expressions, and/or other motions. Imaging sensor outputs may be used for controlling the pump operation.

In some embodiments, the pump device 100 may employ sensors (not shown) which are configured to determine a type of fluid that is contained in the reservoir 106 and/or delivered through the pump device's fluid pathway. For example, based on one or more markers contained in the fluid medicament, an output of such sensors may be used for determining whether the fluid medicament comprises carbidopa, levodopa, and/or dopamine.

Figure 40:
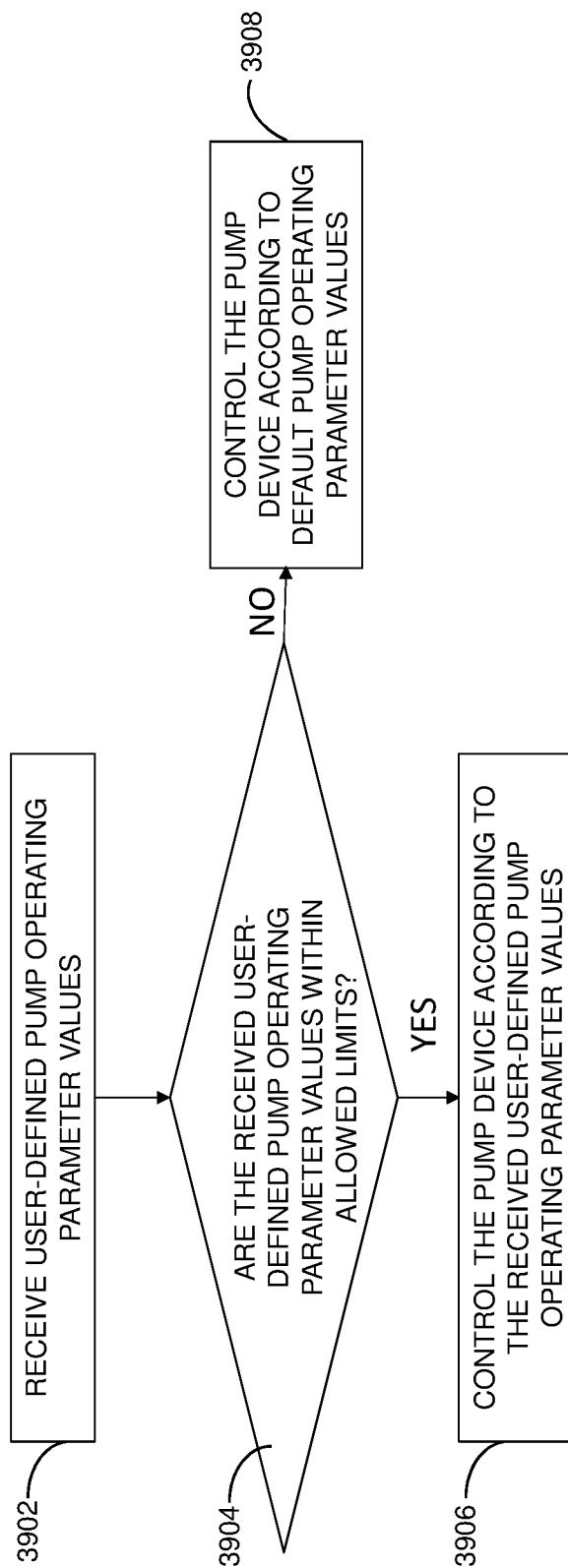
FIG. 40 is a flow chart of an example method for setting operating parameter values of the pump device.

Referring now to FIG. 40, a method for setting operating parameter values of the pump device may include, as indicated by block 3902, receiving, e.g., at the filling station, user-defined pump operating parameter values. In some embodiments, user-defined pump operating parameter values may be given preference over default pump operating parameter values.

The user-defined pump operating parameter values may be provided, for example, by a user via a touch screen of the filling station 154. As indicated by block 3904, the method may further include determining whether the received user-defined pump operating values are within allowed operating parameter limits. If the received user-defined pump operating parameter values are within the allowed operating parameter limits, the method may include controlling operation of the pump device 100 according to the received user-defined pump operating parameter values (block 3906). For example, the user-defined pump operating parameter values may be sent (e.g., wirelessly) from the filling station 154 to the pump device 100.

If the received user-defined pump operating parameter values are not within the allowed limits (block 3904), the method may include operating the pump device 100 according to default pump operating values (block 3908). In that case, the method may include, for example, sending default pump operating parameter values (e.g., from the filling station 154) to the pump device 100, and controlling the pump device 100 accordingly.

Optionally, the default pump operating parameter values and/or the pump operating parameter limits may be stored in the pump device 100 and/or in the filling station 154. Optionally, the default pump operating parameter values may be sent from the pump device 100, along with the pump operating parameter limits, to the filling station 154. Optionally, the default pump operating parameter values may be stored (or pre-stored) in the filling station 154 along with the pump operating parameter limits.

Optionally, the (for example received or for example pre-stored) default pump operating parameter values can be output (e.g., displayed) by the filling station 154 to the user. Optionally, if the provided user-defined pump operating parameter values are not within the allowed operating limits, the default pump operating parameter values may be sent to the pump device 100 to perform control thereof accordingly. Optionally, if the provided user-defined pump operating parameter values are not within the allowed operating limits, a command may be sent to the pump device 100 to initiate control thereof according to the default pump operating parameter values stored in the pump device 100.

The term "controller" as used herein, may also refer to a processor. A controller may, for example, include a circuit programmed to cause the device to implement the methods, processes and/or operations as disclosed herein. For example, a controller may be implemented as a hardware circuit comprising, e.g., custom VLSI circuits or gate arrays, application-specific integrated circuit (ASIC), off-the-shelf semiconductors such as logic chips, transistors, and/or other discrete components. A controller may also be implemented in programmable hardware devices such as field programmable gate arrays, programmable array logic, programmable logic devices and/or the like.

Program instructions for implementing the methods and/or processes disclosed herein may be implemented as a computer program product that may be tangibly embodied in an information carrier including, for example, in a non-transitory tangible computer-readable and/or non-transitory tangible machine-readable storage device. The computer program product may directly loadable into an internal memory of a digital computer, comprising software code portions for performing the methods and/or processes as disclosed herein.

Additionally or alternatively, the methods and/or processes disclosed herein may be implemented as a computer program that may be intangibly embodied by a computer readable signal medium. A computer readable signal medium may include a propagating data signal (e.g., a communication signal) with computer readable program code embodied therein, for example, in baseband or as part of a carrier wave. Such a propagating signal may take any of a variety of forms, including, but not limited to, electromagnetic, optical, or any suitable combination thereof. A computer readable signal medium may be any computer readable medium that is not a non-transitory computer or machine-readable storage device and that can communicate, propagate, or transport a program for use by or in connection with apparatuses, systems, platforms, methods, operations and/or processes discussed herein.

The terms "non-transitory computer-readable storage device" and "non-transitory machine-readable storage device" encompasses distribution media, intermediate storage media, execution memory of a computer, and any other medium or device capable of storing for later reading by a computer program implementing embodiments of a method disclosed herein, and these terms do not encompass a propagating data signal.

The computer readable and executable instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

In the description, unless otherwise stated, adjectives such as "substantially" and "about" that modify a condition or relationship characteristic of a feature or features of an embodiment of the invention, are to be understood to mean that the condition or characteristic is defined to within tolerances that are acceptable for operation of the embodiment for an application for which it is intended. For example, the terms "about," "substantially," and/or "close" with respect to a magnitude or a numerical value may imply to be within an inclusive range of −10% to +10% of the respective magnitude or value.

"Coupled with" means indirectly or directly "coupled with".

It is noted that the terms "operable to" and "operative to" can encompass the meaning of the term "adapted or configured to". In other words, a machine "operable to" perform a task can, in some embodiments, embrace a mere capability and, in some other embodiments, a machine that is actually made to perform the function.

As used herein, the phrase "A,B,C, or any suitable combination of the aforesaid" should be interpreted as meaning all of the following: (i) A or B or C or any combination of A, B, and C, (ii) at least one of A, B, and C, and (iii) A, and/or B and/or C. This concept is illustrated for three elements (i.e., A,B,C), but extends to fewer and greater numbers of elements (e.g., A, B, C, D, etc.).

The terms and expressions employed herein are used as terms and expressions of description and not of limitation and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. The structural features and functions of the some embodiments may be arranged in various combinations and permutations, and all are considered to be within the scope of the disclosed invention. Unless otherwise necessitated, recited steps in the various methods may be performed in any order and certain steps may be performed substantially simultaneously. Accordingly, the described embodiments are to be considered in all respects as only illustrative and not restrictive. Furthermore, the configurations described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A device for delivering a fluid medicament into or through the skin of a user, the device comprising:
   a reusable part comprising:
      a drive component; and
      a control unit for controlling the drive component; and
   a disposable part engageable with the reusable part, the disposable part comprising:
      a first reservoir for containing the fluid medicament, wherein the first reservoir comprises a first bushing, the first bushing fixedly mounted in the first reservoir;
      a first plunger head moveable by a first lead screw in the first reservoir; and
      a first nut concentrically secured by and rotatable in the first bushing, the first nut threadedly engaged with a thread of the first lead screw, wherein the first nut is configured to be detachably coupled with and rotatable by the drive component upon engaging the reusable part with the disposable part and while the reusable part is engaged with the disposable part, and wherein the first nut is configured, upon rotation of the first nut in the first bushing, to linearly displace the first lead screw in a direction dependent on a rotation direction of the first nut.

2. The device of claim 1, wherein the first nut includes a first portion that is insertable into and axially lockable by the first bushing and a second portion having an outer profile adapted to detachably engage with a mating profile of a load gear operable by the drive component.

3. The device of claim 1, wherein the disposable part further comprises an exterior surface adherable to the skin of the user.

4. The device of claim 1, wherein the disposable part further comprises a cannula fluidically coupled to the first reservoir, wherein the cannula is operable to deliver the fluid medicament from the first reservoir to the subcutaneous tissue of the user.

5. The device of claim 1, wherein the reusable part and the disposable part are attachable by using a magnetic force or a snap connection, or a combination thereof.

6. The device of claim 1, wherein, the reusable part and the disposable part are co-planar during attachment and when they are attached.

7. The device of claim 1, wherein the reusable part further comprises a first void for receiving the first lead screw when the first lead screw is retracted in or from the first reservoir.

8. The device of claim 1, wherein the disposable part further comprises:
   a second reservoir for containing additional fluid medicament, wherein the second reservoir comprises a second bushing, the second bushing fixedly mounted in the second reservoir;
   a second plunger head for driving the additional fluid medicament out of the second reservoir, the second plunger head moveable in the second reservoir by a second lead screw; and
   a second nut concentrically secured by and rotatable in the second bushing, the second nut threadedly engaged with a thread of the second lead screw, wherein when the reusable part and the disposable part are attached, the second nut is detachably coupled with and rotatable by the drive component in a direction controllable by the control unit, and wherein the second nut is configured, upon rotation of the second nut in the second bushing, to linearly displace the second lead screw in a direction dependent on a rotation direction of the second nut.

9. The device of claim 8, wherein the drive component is configured to selectively drive the first plunger head and the second plunger head simultaneously or separately.

10. The device of claim 8, wherein the reusable part comprises a first void for receiving the first lead screw when the first lead screw is retracted from the first reservoir, and a second void for receiving the second lead screw when the second lead screw is retracted from the second reservoir.

11. The device of claim 8, wherein the reusable part further comprises a control button to select a mode of operation of the device and wherein the mode of operation is selected from the group of modes consisting of:
- a priming mode, in which the control unit controls the drive component to fill up an infusion set with medicament;
- a medicament delivery mode, in which the control unit controls the drive component to deliver medicament to the user according to a desired rate or schedule;
- a filling mode in which the control unit controls the drive component to perform at least one of the following actions: (i) retract the first plunger head to fill up the first reservoir, (ii) retract the second plunger head to fill up the second reservoir, and (iii) retract both the first plunger head and the second plunger head to fill up both the first reservoir and the second reservoir; and
- a pause mode.

12. The device of claim 8, wherein a fluid sensor is disposed along at least one of the first reservoir and the second reservoir.

13. The device of claim 8, further comprising:
- a cannula fluidically coupled to at least one of the first reservoir and the second reservoir, wherein the cannula is operable to deliver fluid medicament to the subcutaneous tissue of the user from at least one of the first reservoir and the second reservoir; and
- a sensor for sensing at least one functional parameter of the device or the fluid, wherein the sensor comprises at least one of a flow rate sensor, a pressure sensor, a DC current sensor, and a temperature sensor to measure a temperature of the fluid medicament in the cannula or the first reservoir or the second reservoir, or combinations thereof.

14. The device of claim 8, wherein the fluid medicament in the first reservoir and/or in the second reservoir comprises levodopa or carbidopa, or a combination of levodopa and carbidopa.

15. The device of claim 8, wherein the reusable part is engageable with the disposable part in a first orientation and in a second orientation rotated 180 degrees relative to the first orientation, wherein in each orientation each of the first nut and the second nut is engaged with a load gear of the drive component.

16. The device of claim 8, wherein the reusable part and the disposable part are engageable only in a particular orientation of the reusable part with respect to the disposable part in which each of the first nut and the second nut is engageable only with a specific load gear of the drive component.

17. The device of claim 8, wherein the reusable part and the disposable part are attachable by using a magnetic force, a snap connection, or a combination thereof.

18. The device of claim 1, wherein the fluid medicament contained in the first reservoir comprises levodopa or carbidopa, or a combination of levodopa and carbidopa.

19. The device of claim 1, wherein the reusable part further comprises a control button to select a mode of operation of the device, wherein the mode of operation is selected from the group of operation modes consisting of:
- a priming mode, in which the control unit controls the drive component to fill up an infusion set with medicament;
- a medicament delivery mode, in which the control unit controls the drive component to deliver medicament from the first reservoir to the user according to a desired rate or schedule;
- a filling mode in which the control unit controls the drive component to retract the first plunger head to fill up the first reservoir; and
- a pause mode.

20. A disposable part for containing fluid medicament for delivery into or through the skin of a user by a fluid medicament delivery device comprising a reusable part, the disposable part comprising:
- a first reservoir for containing the fluid medicament, said first reservoir engageable with the reusable part;
- a first plunger head moveable by a first lead screw in the first reservoir;
- a first bushing fixedly mounted in the first reservoir; and
- a first nut concentrically secured by and rotatable in the first bushing, the first nut threadedly engaged with the first lead screw, wherein the first nut is configured to be operably coupled with and rotatable by a drive component of the reusable part upon engaging the reusable part and the disposable part and while the reusable part is engaged with the disposable part, and wherein the first nut is configured to linearly displace the first lead screw in the first reservoir in a direction dependent on a rotation direction of the first nut in the first bushing.

21. The disposable part of claim 20, wherein the first nut includes a portion insertable into and axially lockable by and in the first bushing, and a portion having an outer profile that is adapted to detachably engage with a mating profile of a load gear operable by a drive component.

22. The disposable part of claim 20, wherein the fluid medicament comprises levodopa or carbidopa, or a combination of levodopa and carbidopa.

23. The disposable part of claim 20, further comprising:
- a second reservoir for containing an additional fluid medicament;
- a second plunger head moveable by a second lead screw in the second reservoir;
- a second bushing fixedly mounted in the second reservoir; and
- a second nut concentrically secured by and rotatable in the second bushing, the second nut threadedly engaged with the second lead screw to linearly displace the second lead screw in the second reservoir in a direction dependent on a rotation direction of the second nut in the second bushing.

24. The disposable part of claim 23, wherein each of the first nut and the second nut includes a first portion insertable into and axially lockable by and in a respective one of the first bushing and the second bushing and a second portion having an outer profile that is adapted to detachably engage with a mating profile of a load gear operable by the drive component.

25. A reservoir for containing fluid medicament for delivery into or through the skin of a user by a fluid medicament delivery device comprising a reusable part, the reservoir engageable with the reusable part and comprising:
- a plunger head moveable by a lead screw in the reservoir;
- a bushing fixedly mounted in the reservoir; and
- a nut concentrically secured by and rotatable in the bushing, the nut threadedly engaged with the lead screw, wherein, the nut is configured to be operably coupled with and rotatable by a drive component of the reusable part upon engaging the reservoir and the reusable part and while the reusable part is engaged with the reservoir, and wherein the nut is configured to linearly displace the lead screw in the reservoir in a direction dependent on a rotation direction of the nut in the bushing.

26. The reservoir of claim 25, wherein the nut includes a first portion insertable into and axially lockable by and in the bushing and a second portion having an outer profile adapted to detachably engage with a mating profile of a load gear operable by the drive component.

* * * * *